(12) United States Patent
Tachdjian et al.

(10) Patent No.: US 8,420,145 B2
(45) Date of Patent: Apr. 16, 2013

(54) ISOSORBIDE DERIVATIVES AND THEIR USE AS FLAVOR MODIFIERS, TASTANTS, AND TASTE ENHANCERS

(75) Inventors: Catherine Tachdjian, San Diego, CA (US); Donald S. Karanewsky, Escondido, CA (US); Sara L. Adamski-Werner, San Diego, CA (US); Jeffrey M. Yamamoto, San Diego, CA (US); Guy Servant, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 822 days.

(21) Appl. No.: 12/396,917

(22) Filed: Mar. 3, 2009

(65) Prior Publication Data

US 2009/0220662 A1    Sep. 3, 2009

Related U.S. Application Data

(60) Provisional application No. 61/033,140, filed on Mar. 3, 2008, provisional application No. 61/139,421, filed on Dec. 19, 2008.

(51) Int. Cl.
| | | |
|---|---|---|
| *A23L 1/22* | (2006.01) | |
| *A23L 2/56* | (2006.01) | |
| *C07D 401/02* | (2006.01) | |
| *C07D 277/20* | (2006.01) | |
| *C07D 249/04* | (2006.01) | |
| *C07D 405/02* | (2006.01) | |
| *C07D 231/10* | (2006.01) | |
| *C07D 213/02* | (2006.01) | |
| *C07D 333/10* | (2006.01) | |
| *C07D 307/04* | (2006.01) | |

(52) U.S. Cl.
USPC ........ 426/536; 546/268.4; 548/200; 548/248; 548/256; 548/526; 549/60; 549/464

(58) Field of Classification Search ............... 426/536; 546/268.4; 548/200, 248, 256, 526; 549/60, 549/464
See application file for complete search history.

(56) References Cited

U.S. PATENT DOCUMENTS 5,674,522 A * 10/1997 Shah et al. .................. 424/439
2009/0018300 A1    1/2009 Bloom et al.

FOREIGN PATENT DOCUMENTS

| DE | 2262319 A1 | 6/1973 |
|---|---|---|
| GB | 1420974 | 1/1976 |
| JP | 53-15127 A | 2/1978 |
| JP | 2008-13506 A | 7/2006 |
| WO | WO 95/03304 A1 | 2/1995 |
| WO | WO 2004/006846 A2 | 1/2004 |
| WO | WO 2007/121883 A2 | 11/2007 |
| WO | WO 2008/007114 A1 | 1/2008 |

OTHER PUBLICATIONS

Hyun, "International Search Report," 3 pages, PCT appl. No. PCT/US2009/035837, Korean Intellectual Property Office (mailed Oct. 6, 2009).

Hyun, "Written Opinion of the International Searching Authority," 4 pages, PCT appl. No. PCT/US2009/035837, Korean Intellectual Property Office (mailed Oct. 6, 2009).

Nören-Müller et al., "Discovery of protein phosphatase inhibitor classes by biology-oriented synthesis," Proc. Natl. Acad. Sci. USA 103(28):10606-10611 (2006) with supplemental materials.

Muri et al., "Pseudo-peptides derived from isomanide as potential inhibitors of serine proteases," Amino Acids 28:413-419 (2005).

Kang and Ryu, "Intramolecular Cyclization of $C_2$ Symmetric and meso-Iodo Amino Alcohols: A Synthetic Approach to Azasugars," Tetrahedron Letters 38(4):607-610 (1997).

Cortes, "Supplementary European Search Report," 11 pages, EP patent appl. No. 09717709.1 (Jun. 27, 2011).

Chao et al., "Concise and Stereospecific Synthesis of Novel Bicyclic Dideoxynucleosides as Potential Antiviral Agents," Tetrahedron 54:3113-3124 (1998).

Le Guyader et al., "New Radical Allylation Reaction of Iodides," J. Am. Chem. Soc. 119:7410-7411 (1997).

Bachmann et al., "Synthesis of Novel polyurethanes and polyureas by polyaddition reactions of dianhydrohexitol configurated diisocyanates," 6 pages, STN File CAPLUS accession No. 2002:11688 (2001).

* cited by examiner

*Primary Examiner* — Samantha Shterengarts
(74) *Attorney, Agent, or Firm* — Cooley LLP

(57) ABSTRACT

The present invention provides isosorbide derivatives having the formula shown below and certain subgenera or species thereof, as flavor or taste modifiers, particularly, savory ("umami") taste modifiers, savory flavoring agents and savory flavor enhancers in foods, beverages, and other comestible compositions,

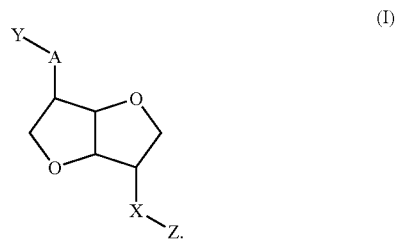

(I)

14 Claims, 2 Drawing Sheets

ISOSORBIDE DERIVATIVES AND THEIR USE AS FLAVOR MODIFIERS, TASTANTS, AND TASTE ENHANCERS

CROSS-REFERENCE TO RELATED APPLICATIONS

The present application claims priority to U.S. Provisional Application No. 61/033,140, filed Mar. 3, 2008 and entitled "ISOSORBIDE DERIVATIVES AND THEIR USE AS FLAVOR MODIFIERS, TASTANTS, AND TASTE ENHANCERS", and U.S. Provisional Application No. 61/139,421, filed Dec. 19, 2008 and entitled "ISOSORBIDE DERIVATIVES AND THEIR USE AS FLAVOR MODIFIERS, TASTANTS, AND TASTE ENHANCERS", the content of which are incorporated by reference in their entirety for all purposes.

FIELD OF THE INVENTION

The present invention relates to isosorbide derivatives and their use as flavor or taste modifiers, such as a flavoring or flavoring agents and flavor or taste enhancers, more particularly, savory ("umami") taste modifiers, savory flavoring agents and savory flavor enhancers, for foods, beverages, and other comestible or non-comestible compositions.

BACKGROUND OF THE INVENTION

For centuries, various natural and unnatural compositions and/or compounds have been added to foods, beverages, and/or comestible compositions to improve their taste. Although it has long been known that there are only a few basic types of "tastes" (sweet, sour, bitter, salty, and "umami"/savory), the biological and biochemical basis of taste perception was poorly understood, and most taste improving or taste modifying agents have been discovered largely by simple trial and error processes.

One of the five known basic tastes is the "savory" or "umami" flavor of monosodium glutamate ("MSG"), which is now commonly added to many food and beverage compositions to desirably improve their "savory" flavor. MSG is known to produce adverse reactions in some people, but very little progress has been made in identifying artificial substitutes for MSG. It is known that a few naturally occurring materials can increase or enhance the effectiveness of MSG as a savory flavoring agent, so that less MSG is needed for a given flavoring application. For example the naturally occurring nucleotide compounds inosine monophosphate (IMP) or guanosine monophosphate (GMP) are known to have a synergistic and/or multiplier effect on the savory taste of MSG. Nevertheless, IMP and GMP are both difficult and expensive to either synthesize or isolate and purify from natural sources and hence have limited practical application to many commercial needs in food compositions. Less expensive compounds that would provide and/or replace the flavor of MSG itself, or multiply the effectiveness of any MSG that is present, e.g. to replace the need for IMP or GMP additives, could be of very high value. This is especially true if the compounds could be used at low concentrations, so as to minimize costs and possible health risks.

In recent years substantial progress has been made in biotechnology and particularly in understanding the underlying biological and biochemical phenomena of taste perception. For example, taste receptor proteins involved in taste perception have been recently identified in mammals. In particular, two different families of G protein coupled receptors believed to be involved in taste perception, T2Rs and T1Rs, have been identified. (See, e.g., Nelson, et al., Cell (2001) 106(3):381-390; Adler, et al., Cell (2000) 100(6):693-702; Chandrashekar, et al., Cell (2000) 100:703-711; Matsunami, et al., Nature (2000) 404:601-604; Li, et al., Proc. Natl. Acad. Sci. USA (2002) 99:4962-4966; Montmayeur, et al., Nature Neuroscience (2001) 4(S):492-498: U.S. Pat. No. 6,462,148; PCT publications WO 02/06254, WO 00/63166 art, WO 02/064631, and WO 03/001876, and U.S. Patent publication US 2003-0232407 A1). The entire disclosures of the articles, patent applications, and issued patents cited immediately above are hereby incorporated herein by reference, for all purposes, including a) their disclosures of the identities and structures of T2Rs and T1Rs mammalian taste receptor proteins; b) methods for artificially expressing those receptors in cell lines; c) using the resulting cell lines for screening compounds as potential "savory" flavoring agents; and d) assays and/or high throughput screens that measure T1R1/T1R3 or T1R2/T1R3 receptor activity by fluorometric imaging in the presence of the target compounds.

Whereas the T2R family includes over 25 genes that are involved in bitter taste perception, the T1R family includes only three members, T1R1, T1R2 and T1R3. (See Li, et al., Proc. Natl. Acad. Sci. USA (2002) 99:49624966.) Recently it was disclosed in WO 02/064631 and/or WO 03/001876 that certain T1R members, when co-expressed in suitable mammalian cell lines, assemble to form functional taste receptors. Particularly it was found that co-expression of T1R1 and T1R3 in a suitable host cell results in a functional T1R1/T1R3 savory ("umami") taste receptor that responds to savory taste stimuli, including monosodium glutamate. (See Li, et al. (Id.).

Recently, certain U.S. and international patent applications have been filed by some of the current Applicants that disclosed the use of certain compounds as umami and/or sweet tastants, and/or synergistic enhancers of the "Umami" taste of MSG, and/or the sweet taste of a variety of natural and artificial sweeteners. See, for example, U.S. Provisional Patent Application Ser. No. 60/494,071 filed Aug. 6, 2003, U.S. Provisional Patent Application Ser. No. 60/552,064 filed Mar. 9, 2004, U.S. Utility patent application Ser. No. 10/913,303, filed Aug. 6, 2004 and published as U.S. Patent Publication Serial No. US-2005-0084506-A1 on Apr. 21, 2005; and PCT Patent Application Serial No. PCT/US04/25419 filed Aug. 6, 2004 and published as PCT Publication WO 2005/041684 on May 12, 2005, and PCT Publication WO 2005/015158 published on Feb. 17, 2005. The entire disclosures of the patent applications cited immediately above are hereby incorporated herein by this reference, for all purposes, including their disclosures of the identities and structures of compounds that can serve as potential "savory" or sweet flavoring agents or enhancers. Nevertheless, there is a continuing need for new and improved taste enhancing compounds.

SUMMARY OF THE INVENTION

In one aspect, the present invention provides a compound having structural formula (I)

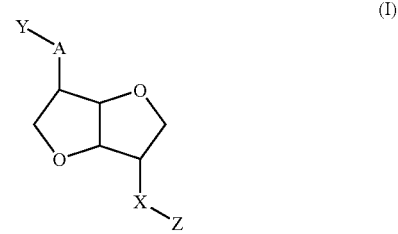

or the salt, solvate, N-oxide, ester, and/or prodrug thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$, —S(O)$_2$R$^1$, —OC(O)R$^1$, —N(R$^1$)C(O)R$^2$, —NR$^1$R$^2$, —C(O)NR$^1$R$^2$, —C(O)OR$^1$, —S(O)$_2$NR$^1$R$^2$, —COR$^1$, —N(R$^1$)S(O)$_2$R$^2$, —SR$^1$, —C(R$^1$R$^2$R$^6$), —C(S)—R$^1$, —C(=NR$^2$)—R$^1$, —N(R$^1$)—C(=N—OR$^2$)R$^6$, —N(R$^1$)C(S)NR$^2$R$^6$, —C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$, —C(=NR$^1$)O—NR$^2$R$^6$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^1$)(R$^2$), or —P(O)R$^1$R$^2$;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —N(R$^3$)—C(=N—OR$^4$)—, —C(=N—OR$^3$)—, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —N(R$^3$)—C(O)—C(O)—NR$^4$—, —C(O)—C(O)—NR$^4$—, —P(O)(OR$^3$)—, or —P(O)R$^3$—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl;

R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; and with the following provisos: (a) when A is triazole or tetrazole; then —X-Z is not —O-alkyl, —O-acyl, or sulfonamido; (b) when A is tetrazole, and Z is cyclohexyl; then X is not —NH—C(O)—, —NH—C(O)—NH—; and (c) when A is a covalent bond, then Y is not hydrogen.

In another aspect, the present invention provides a composition comprising the compound of formula (I):

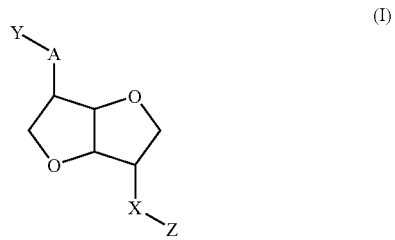

(I)

or the salt, solvate, N-oxide, ester, and/or prodrug thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$, —S(O)$_2$R$^1$, —OC(O)R$^1$, —N(R$^1$)C(O)R$^2$, —NR$^1$R$^2$, —C(O)NR$^1$R$^2$, —C(O)OR$^1$, —S(O)NR$^1$R$^2$, —COR$^1$, —N(R$^1$)S(O)$_2$R$^2$, —SR$^1$, —C(R$^1$R$^2$R$^6$), —C(S)—R$^1$, —C(=NR$^2$)—R$^1$, —N(R$^1$)—C(=N—OR$^2$)R$^6$, —N(R$^1$)C(S)NR$^2$R$^6$, —C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$, —C(=NR$^1$)O—NR$^2$R$^6$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^1$)(R$^2$), or —P(O)R$^1$R$^2$;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —N(R$^3$)—C(=N—OR$^4$)—, —C(=N—OR$^3$)—, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —N(R$^3$)—C(O)—C(O)—NR$^4$—, —C(O)—C(O)—NR$^4$—, —P(O)(OR$^3$)—, or —P(O)R$^3$—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl;

R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

In another aspect, the present invention provides a method for modulating the savory taste of a composition comprising combining the composition with at least one compound of formula (I):

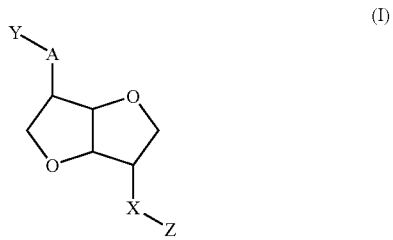

(I)

or the salt, solvate, N-oxide, ester, and/or prodrug thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$, —S(O)$_2$R$^1$, —OC(O)R$^1$, —N(R$^1$)C(O)R$^2$, —NR$^1$R$^2$, —C(O)NR$^1$R$^2$, —C(O)OR$^1$, —S(O)$_2$NR$^1$R$^2$, —COR$^1$, —N(R$^1$)S(O)$_2$R$^2$, —SR$^1$, —C(R$^1$R$^2$R$^6$), —C(S)—R$^1$, —C(=NR$^2$)—R$^1$, —N(R$^1$)—C(=N—OR$^2$)R$^6$, —N(R$^1$)C(S)NR$^2$R$^6$, —C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$, —C(=NR$^1$)O—NR$^2$R$^6$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^1$)(R$^2$), or —P(O)R$^1$R$^2$;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —N(R$^3$)—C(=N—OR$^4$)—, —C(=N—OR$^3$)—, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —N(R$^3$)—C(O)—C(O)—NR$^4$—, —C(O)—C(O)—NR$^4$—, —P(O)(OR$^3$)—, or —P(O)R$^3$—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl;

R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

DETAILED DESCRIPTION OF THE INVENTION

Figure 1:
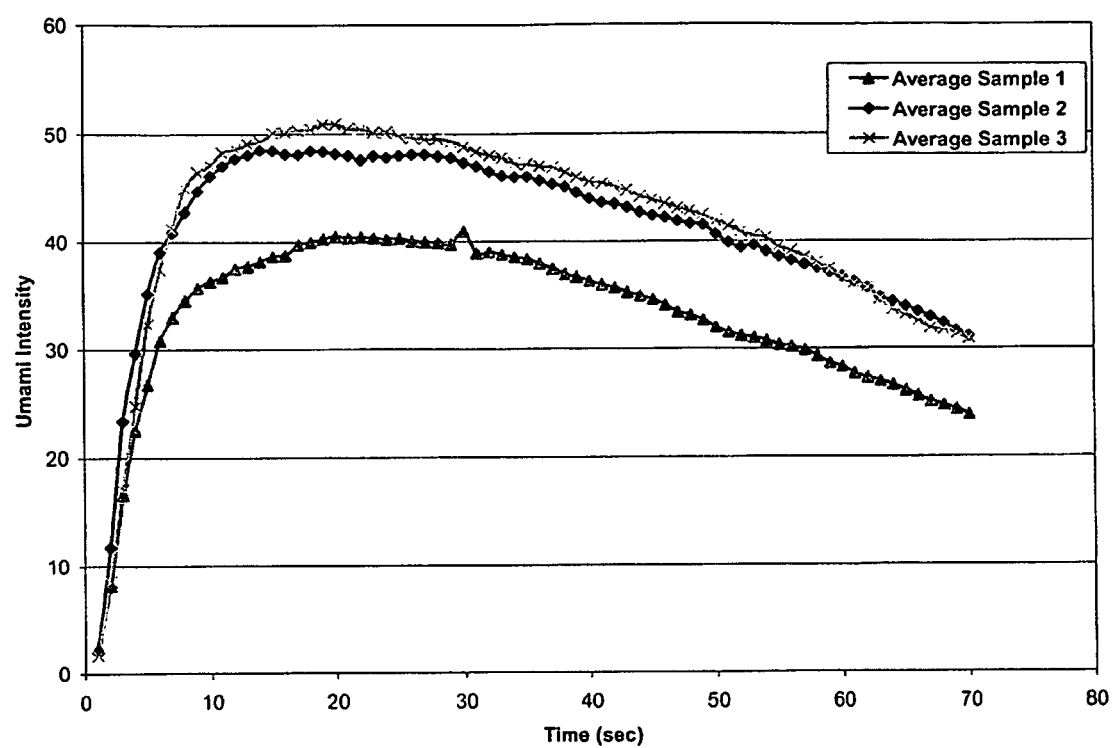
FIG. 1 is a graph showing the panel average umami intensity ratings over 2 sessions for 70 second rating period, n=33 (17 Panelists×1rep×day1 and 16 panelists×1rep×day2).

The present invention can be understood more readily by reference to the following detailed description of various embodiments of the invention and the Examples included therein and to the chemical drawings and Tables and their previous and following description. Before the present compounds, compositions, and/or methods are disclosed and described, it is to be understood that unless otherwise specifically indicated by the claims, the invention is not limited to specific foods or food preparation methods, specific comestible carriers or formulations, or to particular modes of formulating the compounds of the invention into comestible products or compositions intended for oral administration, because as one of ordinary skill in relevant arts is well aware, such things can of course, vary. It is also to be understood that the terminology used herein is for the purpose of describing particular embodiments only and is not intended to be limiting.

Definitions

A "comestibly acceptable carrier or excipient" is a solid or liquid medium and/or composition that is used to prepare a desired dispersed dosage form of the inventive compound, in order to administer the inventive compound in a dispersed/diluted form, so that the biological effectiveness of the inventive compound is maximized. Comestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A "flavor" herein refers to the perception of taste and/or smell in a subject, which include sweet, sour, salty, bitter, umami, and others. The subject may be a human or an animal.

A "flavoring agent" herein refers to a compound or a biologically acceptable salt thereof that induces a flavor or taste in an animal or a human.

A "flavor modifier" herein refers to a compound or biologically acceptable salt thereof that modulates, including enhancing or potentiating, and inducing, the tastes and/or smell of a natural or synthetic flavoring agent in an animal or a human.

A "flavor enhancer" herein refers to a compound or biologically acceptable salt thereof that enhances and/or multiplies the tastes or smell of a natural or synthetic flavoring agent, or a comestible composition comprising the flavor enhancer.

"Savory flavor" herein refers to the savory "umami" taste typically induced by MSG (mono sodium glutamate) in an animal or a human.

"Savory flavoring agent," "savory compound" or "savory receptor activating compound" herein refers to a compound or biologically acceptable salt thereof that elicits a detectable savory flavor in a subject, e.g., MSG (mono sodium glutamate) or a compound that activates a T1R1/T1R3 receptor in vitro. The subject may be a human or an animal. Compounds of the present invention are savory flavoring agents/compounds.

A "savory flavor modifier" herein refers to a compound or biologically acceptable salt thereof that modulates, including enhancing or potentiating, inducing, and blocking, the savory taste of a natural or synthetic savory flavoring agents, e.g., monosodium glutamate (MSG) in an animal or a human.

A "savory flavor enhancer" herein refers to a compound or biologically acceptable salt thereof that enhances or potentiates the savory taste of a natural or synthetic savory flavoring agents, e.g., monosodium glutamate (MSG) in an animal or a human.

An "umami receptor activating compound" herein refers to a compound that activates an umami receptor, such as a T1R1/T1R3 receptor.

An "umami receptor modulating compound" herein refers to a compound that modulates (activates, enhances or blocks) an umami receptor.

An "umami receptor enhancing compound" herein refers to a compound that enhances or potentiates the effect of a natural or synthetic umami receptor activating compound, e.g., monosodium glutamate (MSG).

A "savory flavor modulating amount" herein refers to an amount of a compound of Formula (I) that is sufficient to alter (either increase or decrease) savory taste in a comestible or medicinal product or composition, or a precursor thereof, sufficiently to be perceived by a human subject. In many embodiments of the invention, at least about 0.001 ppm of the heterocyclic compound would need to be present in order for most human subjects to perceive a modulation of the savory flavor of a comestible composition comprising the heterocyclic compound. A broad range of concentration that would typically be employed in order to economically provide a desirable degree of savory flavor modulation can be from about 0.001 ppm to 100 ppm, or a narrow range from about 0.1 ppm to about 10 ppm. Alternative ranges of savory flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "savory flavor enhancing amount" herein refers to an amount of a compound that is sufficient to enhance the taste of a natural or synthetic flavoring agents, e.g., monosodium glutamate (MSG) in a comestible or medicinal product or composition, as perceived by an animal or a human. A broad range of a savory flavor enhancing amount can be from about 0.001 ppm to 100 ppm, or a narrow range from about 0.1 ppm to about 10 ppm. Alternative ranges of savory flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

An "umami receptor modulating amount" herein refers to an amount of a compound that is sufficient to modulate (activate, enhance or block) an umami taste receptor protein. In many embodiments of the invention, an umami receptor modulating amount is at least about 1 pM, or at least about 1 nM, or at least about 10 nM, or at least about 100 nM (i.e. about 0.1 µM). A "T1R1/T1R3 receptor modulating or activating amount" is an amount of compound that is sufficient to modulate or activate a T1R1/T1R3 receptor. These amounts are preferably the same as the umami receptor modulating amounts.

An "umami receptor" is a taste receptor that can be modulated by a savory compound. Preferably an umami receptor is a G protein coupled receptor, and more preferably the umami receptor is a T1R1/T1R3 receptor.

Compounds of the invention modulate an umami receptor and preferably are agonists of the T1R1/T1R3 receptor. An agonist of this receptor has the effect of activating a G protein signaling cascade. In many cases, this agonist effect of the compound on the receptor also produces a perceived savory flavor in a taste test. It is desirable, therefore, that such inventive compounds serve as a replacement or enhancer for MSG, which is not well tolerated by some in, for example, comestible products.

In addition, this agonist effect also is responsible for the synergistic savory taste effect, which occurs when a compound of the invention is combined with another savory flavoring agent such as MSG. The nucleotides, IMP or GMP, are conventionally added to MSG, to intensify the savory flavor of MSG, so that relatively less MSG is needed to provide the same savory flavor in comparison to MSG alone. Therefore, it is desirable that combining compounds of the invention with another savory flavoring agent such as MSG advantageously eliminates the need to add expensive nucleotides, such as IMP, as a flavor enhancer, while concomitantly reducing or eliminating the amount of a savory compound such as MSG needed to provide the same savory flavor in comparison to the savory compound or MSG alone.

A "synergistic effect" relates to the enhanced savory flavor of a combination of savory compounds or receptor activating compounds, in comparison to the sum of the taste effects or flavor associated effects associated with each individual compound. In the case of savory enhancer compounds, a synergistic effect on the effectiveness of MSG may be indicated for a compound of Formula (I) having an EC50 ratio (defined herein below) of 2.0 or more, or preferably 5.0 or more, or 10.0 or more, or 15.0 or more.

When the compounds described here include one or more chiral centers, the stereochemistry of such chiral centers can independently be in the R or S configuration, or a mixture of the two. The chiral centers can be further designated as R or S or R,S or d,D, l,L or d,l, D,L. Correspondingly, the compounds of the invention, if they can be present in optically active form, can be present in the form of a racemic mixture of enantiomers, or in the form of either of the separate enantiomers in substantially isolated and purified form, or as a mixture comprising any relative proportions of the enantiomers. Where so indicated in the claims herein, if a single enantiomer of the potentially optically active heterocyclic compounds disclosed is desired, for either health or efficacy reasons, preferably it is present in an enantiomeric excess of at least about 80%, or at least about 90%, or at least about 95%, or at least about 98%, or at least about 99%, or at least about 99.5%.

As used herein, "hydrocarbon residue" or "hydrocarbon radical" refers to a chemical sub-group or radical within a larger chemical compound which contains only carbon and hydrogen atoms. The hydrocarbon residue may be aliphatic or aromatic, straight-chain, cyclic, branched, saturated or unsaturated. In many embodiments the hydrocarbon residues are of limited dimensional size and molecular weight, and may comprise 1 to 18 carbon atoms, 1 to 16 carbon atoms, 1 to 12 carbon atoms, 1 to 10 carbon atoms, 1 to 8 carbon atoms, 1 to 6 carbon atoms, or 1 to 4 carbon atoms.

The hydrocarbon residue, when described as "substituted," contains or is substituted with one or more independently selected heteroatoms such as O, S, N, P, or the halogens (fluorine, chlorine, bromine, and iodine), or one or more substituent groups containing heteroatoms (OH, $NH_2$, $NO_2$, $SO_3H$, and the like) over and above the carbon and hydrogen atoms of the substituent residue. Substituted hydrocarbon residues may also contain carbonyl groups, amino groups, hydroxyl groups and the like, or contain heteroatoms inserted into the "backbone" of the hydrocarbon residue.

As used herein, "inorganic" group or residue refers to a neutral, cationic, or anionic radical substituents on the organic molecules disclosed or claimed herein that have from one to 16 atoms that do not include carbon, but do contain other heteroatoms from the periodic table that preferably include one or more atoms independently selected from the group consisting of H, O, N, S, one or more halogens, or alkali metal or alkaline earth metal ions. Examples of inorganic radicals include, but are not limited to, H, Na+, Ca++ and K+, halogens which include fluorine, chlorine, bromine, and iodine, OH, SH, $SO_3H$, $SO_3^-$, $PO_3H$, $PO_3^-$, NO, $NO^2$ or $NH_2$, and the like.

As used herein, the term "alkyl," "alkenyl" and "alkynyl" include straight- and branched-chain and cyclic monovalent substituents that respectively are saturated, unsaturated with at least one double bond, and unsaturated with at least one triple bond.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the alkyl groups are "C1 to C6 alkyl" such as methyl, ethyl, propyl, isopropyl, n-butyl, iso-butyl, sec-butyl, tert-butyl, amyl, tert-amyl, hexyl and the like. Many embodiments of the invention comprise "Cl to C4 alkyl" groups (alternatively termed "lower alkyl" groups) that include, but are not limited to, methyl, ethyl, propyl, iso-propyl n-butyl, iso-butyl, sec-butyl, and t-butyl groups. Some of the preferred alkyl groups of the invention have three or more carbon atoms preferably 3 to 16 carbon atoms, 4 to 14 carbon atoms, or 6 to 12 carbon atoms.

The term "alkenyl" is structurally analogous to an alkyl group or residue that comprises at least one carbon-carbon double bond. In some embodiments, alkenyl groups are "C2 to C7 alkenyls" which are exemplified by vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains. In other embodiments, alkenyls are limited to two to four carbon atoms.

The term "alkynyl" is analogous to an alkyl group or radical that comprises at least one carbon-carbon triple bond. Preferred alkynyl groups are "C2 to C7 alkynyl" such as ethynyl, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl as well as di- and tri-ynes of straight and branched chains including ene-ynes.

The terms "substituted alkyl," "substituted alkenyl," "substituted alkynyl," and "substituted alkylene" denote that the alkyl, alkenyl, or alkynyl groups or radicals as described herein, wherein one or more hydrogen atoms has been conceptually substituted by one or more, and preferably one or two independently selected organic or inorganic substituent groups or radicals, that can include a halogen, hydroxy, amino, SH, a C1 to C7 alkoxy, or alkoxy-alkyl, oxo, C3 to C7 cycloalkyl, naphthyl, amino, (monosubstituted)amino, (disubstituted)amino, guanidino, heterocycle, substituted heterocycle, imidazolyl, indolyl, pyrrolidinyl, C1 to C7 acyl, C1 to C7 acyloxy, nitro, carboxy, carbamoyl, carboxamide, N—(C1 to C6 alkyl)carboxamide, N,N-di(C1 to C6 alkyl) carboxamide, cyano, methylsulfonylamino, thiol, C1 to C4 alkylthio or C1 to C4 alkylsulfonyl groups. The substituted alkyl groups may be substituted once or more, and preferably once or twice, with the same or with different substituents. In many embodiments of the invention, a preferred group of substituent groups for a substantial alkyls include hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups. In many embodiments of the invention that comprise the above lists of substituent groups, an even more preferred group of substituent groups include hydroxy, SEt, $SCH_3$, methyl, ethyl, isopropyl, trifluromethyl, methoxy, ethoxy, and trifluoromethoxy groups.

Examples of the above substituted alkyl groups include the 2-oxo-prop-1-yl, 3-oxo-but-1-yl, cyanomethyl, nitromethyl, chloromethyl, trifluoromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, I-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted double bond can be included.

Examples of substituted alkynyl groups include phenylacetylen-1-yl, 1-phenyl-2-propyn-1-yl and the like.

"Heteroalkyl" refers to alkyl group in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$_2$—, =N—N=, —N=N—, —N=N—NR$_2$, —PR—, —P(O)$_2$—, —POR—, —O—P(O)$_2$—, —SO—, —SO$_2$—, —SnR$_2$— and the like, where R is each independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Haloalkyl" is substituted alkyl group or residue wherein one or more hydrogens of the corresponding alkyl group have been replaced with a halogen atom (fluorine, chlorine, bromine, and iodine). Preferred haloalkyls can have one to four carbon atoms. Examples of preferred haloalkyl groups include trifluoromethyl and pentafluoroethyl groups.

Haloalkoxy groups are alkoxy groups or residues wherein one or more hydrogens from the R group of the alkoxy group are a halogen atom (fluorine, chlorine, bromine, and iodine). Preferred haloalkoxy groups can have one to four carbon atoms. Examples of preferred haloalkoxy groups include trifluoromethyoxy and pentafluoroethoxy groups.

The term "oxo" denotes a carbon atom bonded to two additional carbon atoms substituted with an oxygen atom doubly bonded to the carbon atom, thereby forming a ketone radical or residue.

"Alkoxy" or "alkoxyl" refers to an —OR radical or group, wherein R is an alkyl radical. In some embodiments the alkoxy groups can be C1 to C8, and in other embodiments can be C1 to C4 alkoxy groups wherein R is a lower alkyl, such as a methoxy, ethoxy, n-propoxy, isopropoxy, n-butoxy, t-butoxy and like alkoxy groups. The term "substituted alkoxy" means that the R group is a substituted alkyl group or residue.

Examples of substituted alkoxy groups include trifluoromethoxy, hydroxymethyl, hydroxyethyl, hydroxypropyl, and alkoxyalkyl groups such as methoxymethyl, methoxyethyl, polyoxoethylene, polyoxopropylene, and similar groups.

"Alkylamine" refers to —NHR or —NR$^2$, wherein each R is independently an alkyl radical. In some embodiments the alkylamine groups can be C1 to C8, and in other embodiments can be C1 to C4 alkylamine groups wherein R is a lower alkyl, such as a methylamine, ethylamine, propylamine, N,N-methylethylamine, N,N-dimethylamine, N,N-diethylamine, N,N-diisopropylamine and like alkylamine groups.

"Alkoxyalkyl" refers to an —R—O—R' group or radical, wherein R and R' are alkyl groups. In some embodiments the alkoxyalkyl groups can be C1 to C8, and in other embodiments can be C1 to C4. In many embodiments, both R and R' are a lower alkyl, such as a methoxy, ethoxy, n-propoxy, isopropoxy, n-butoxy, t-butoxy and like alkoxy groups. Examples of alkoxyalkyl groups include, methoxymethyl, ethoxyethyl, methoxypropyl, and methoxybutyl and similar groups.

"Acyloxy" refers to an RCO$_2$— ester group where R is an alkyl, cycloalkyl, aryl, heteroaryl, substituted alkyl, substituted cycloalkyl, substituted aryl, or substituted hetearyl group or radical wherein the R radical comprises one to seven or one to four carbon atoms. In many embodiments, R is an alkyl radical, and such acyloxy radicals are exemplified by formyloxy, acetoxy, propionyloxy, butyryloxy, pivaloyloxy, pentanoyloxy, hexanoyloxy, heptanoyloxy and the like. In other embodiments the R groups are C1-C4 alkyls.

As used herein, "acyl" encompasses the definitions of alkyl, alkenyl, alkynyl and the related hetero-forms which are coupled to an additional organic residue through a carbonyl group to form a ketone radical or group. Preferred acyl groups are "C1 to C7 acyl" such as formyl, acetyl, propionyl, butyryl, pentanoyl, pivaloyl, hexanoyl, heptanoyl, benzoyl and the like. More preferred acyl groups are acetyl and benzoyl.

The term "substituted acyl" denotes an acyl group wherein the R group substituted by one or more, and preferably one or two, halogen, hydroxy, oxo, alkyl, cycloalkyl, naphthyl, amino, (monosubstituted)amino, (disubstituted)amino, guanidino, heterocyclic ring, substituted heterocyclic ring, imidazolyl, indolyl, pyrrolidinyl, C1 to C7 alkoxy, alkoxyalkyl, C1 to C7 acyl, C1 to C7 acyloxy, nitro, C1 to C6 alkyl ester, carboxy, alkoxycarbonyl, carbamoyl, carboxamide, N—(C1 to C6 alkyl)carboxamide, N,N-di(C1 to C6 alkyl) carboxamide, cyano, methylsulfonylamino, thiol, C1 to C4 alkylthio or C1 to C4 alkylsulfonyl groups. The substituted acyl groups may be substituted once or more, and preferably once or twice, with the same or with different substituents.

Examples of C1 to C7 substituted acyl groups include 4-phenylbutyroyl, 3-phenylbutyroyl, 3-phenylpropanoyl, 2-cyclohexanylacetyl, cyclohexanecarbonyl, 2-furanoyl and 3 dimethylaminobenzoyl.

"Carbocyclyl", as used herein, denotes a saturated, unsaturated, or partially saturated hydrocarbon radical having some or all carbon atoms linked in one or more ring structures. Carbocyclyl includes cycloalkyl, cycloalkylene, cycloalkenyl, cycloalkenylene, and the like, such as, for example, cyclohexylmethylene.

Cycloalkyl residues or groups are structurally related to cyclic monocyclic or bicyclic hydrocarbon compounds wherein one or more hydrogen atoms has been replaced with an organic or inorganic substituent group. The cycloalkyls of the current inventions comprise at least 3 up to 12, or more preferably 3 to 8 ring carbon atoms, or more preferably 4 to 6 ring carbon atoms. Examples of such cycloalkyl residues include cyclopropyl, cyclobutyl, cyclopentyl, cyclohexyl, cycloheptyl, cyclooctyl rings, and saturated bicyclic or fused polycyclic cycloalkanes such as decalin groups, polycyclic norbornyl or adamantly groups, and the like.

Preferred cycloalkyl groups include "C3 to C7 cycloalkyl" such as cyclopropyl, cyclobutyl, cyclopentyl, cyclohexyl or cycloheptyl rings. Similarly, the term "C5 to C7 cycloalkyl" includes cyclopentyl, cyclohexyl or cycloheptyl rings.

"Substituted cycloalkyl" denote a cycloalkyl rings as defined above, substituted by 1 to four, or preferably one or two substituents independently selected from a halogen, hydroxy, C1 to C4 alkylthio, C1 to C4 alkylsulfoxide, C1 to C4 alkylsulfonyl, C1 to C4 substituted alkylthio, C1 to C4 substituted alkylsulfoxide, C1 to C4 substituted alkylsulfonyl, C1 to C4 alkyl, C1 to C4 alkoxy, C1 to C6 substituted alkyl, C1 to C4 alkoxy-alkyl, oxo (monosubstituted)amino, (disubstituted)amino, trifluoromethyl, carboxy, phenyl, substituted phenyl, phenylthio, phenylsulfoxide, phenylsulfonyl, amino. In many embodiments of substituted cycloalkyl groups, the substituted cycloalkyl group will have 1, 2, 3, or 4 substituent groups independently selected from hydroxy, fluoro, chloro, NH$_2$, NHCH$_3$, N(CH$_3$)$_2$, CO$_2$CH$_3$, SEt, SCH$_3$, methyl, ethyl, isopropyl, vinyl, trifluoromethyl, methoxy, ethoxy, isopropoxy, and trifluoromethoxy groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "cycloalkenyl" indicates preferably a 1,2, or 3-cyclopentenyl ring, a 1,2,3 or 4-cyclohexenyl ring or a 1,2,3,4 or 5-cycloheptenyl ring, while the term "substituted cycloalkenyl" denotes the above cycloalkenyl rings substituted with a substituent, preferably by a C1 to C6 alkyl, halogen, hydroxy, C1 to C7 alkoxy, alkoxy-alkyl, trifluoromethyl, carboxy, alkoxycarbonyl oxo, (monosubstituted) amino, (disubstituted)amino, phenyl, substituted phenyl, amino, or protected amino.

The term "cycloalkenylene" is a cycloalkenyl ring, as defined above, where the cycloalkenyl radical is bonded at two positions connecting together two separate additional groups. Similarly, the term "substituted cycloalkenylene" means a cycloalkenylene further substituted preferably by halogen, hydroxy, C1 to C4 alkylthio, C1 to C4 alkylsulfoxide, C1 to C4 alkylsulfonyl, C1 to C4 substituted alkylthio, C1 to C4 substituted alkylsulfoxide, C1 to C4 substituted alkylsulfonyl, C1 to C6 alkyl, C1 to C7 alkoxy, C1 to C6 substituted alkyl, C1 to C7 alkoxy-alkyl, oxo, (monosubstituted) amino, (disubstituted)amino, trifluoromethyl, carboxy, alkoxycarbonyl, phenyl, substituted phenyl, phenylthio, phenylsulfoxide, phenylsulfonyl, amino, or substituted amino group.

The term "heterocyclyl" or "heterocyclic ring" denotes optionally substituted 3 to 8-membered rings having one or more carbon atoms connected in a ring that also comprise 1 to 5 ring heteroatoms, such as oxygen, sulfur and/or nitrogen inserted into the ring. These heterocyclic rings can be saturated, unsaturated or partially unsaturated, but are preferably saturated. Preferred unsaturated heterocyclic rings include furanyl, thiofuranyl, pyrrolyl, pyridyl, pyrimidyl, pyrazinyl, benzoxazole, benzthiazole, quinolinlyl, and like heteroaromatic rings. Preferred saturated heterocyclic rings include piperidyl, aziridinyl, piperidinyl, piperazinyl, tetrahydrofurano, pyrrolyl, and tetrahydrothiophenyl rings.

The term "substituted heterocycle" or "substituted heterocyclic ring" means the above-described heterocyclic ring is substituted with, for example, one or more, and preferably one or two, substituents which are the same or different which substituents preferably can be halogen, hydroxy, thio, alkylthio, cyano, nitro, C1 to C4 alkyl, C1 to C4 alkoxy, C1 to C4 substituted alkoxy, alkoxy-alkyl, C1 to C4 acyl, C1 to C4 acyloxy, carboxy, alkoxycarbonyl, carboxymethyl, hydroxymethyl, alkoxy-alkyl amino, monosubstituted) amino, (disubstituted)amino carboxamide, N—(C1 to C6 alkyl)carboxamide, N,N-di(C1 to C6 alkyl)carboxamide, trifluoromethyl, N—((C1 to C6 alkyl)sulfonyl)amino, N-(phenylsulfonyl)amino groups, or substituted with a fused ring, such as benzo-ring. In many embodiments of substituted heterocyclic groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

An "aryl" group refers to a monocyclic, linked bicyclic or fused bicyclic radical or group comprising at least one six membered aromatic "benzene" ring. Aryl groups preferably comprise between 6 and 12 ring carbon atoms, and are exemplified by phenyl, biphenyl, naphthyl, indanyl, and tetrahydronapthyl groups. Aryl groups can be optionally substituted with various organic and/or inorganic substituent groups, wherein the substituted aryl group in combination with all its substituents comprise between 6 and 18, or preferably 6 and 16 total carbon atoms. Preferred optional substituent groups include 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The term "heteroaryl" means a heterocyclic aryl derivative which preferably contains a five-membered or six-membered conjugated and aromatic ring system having from 1 to 4 heteroatoms independently selected from oxygen, sulfur and/or nitrogen, inserted into the unsaturated and conjugated heterocyclic ring. Heteroaryl groups include monocyclic heteroaromatic, linked bicyclic heteroaromatic or fused bicyclic heteroaromatic moieties. Examples of heteroaryls include pyridinyl, pyrimidinyl, and pyrazinyl, pyridazinyl, pyrrolyl, furanyl, thiofuranyl, oxazoloyl, isoxazolyl, phthalimido, thiazolyl, quinolinyl, isoquinolinyl, indolyl, or a furan or thiofuran directly bonded to a phenyl, pyridyl, or pyrrolyl ring and like unsaturated and conjugated heteroaromatic rings. Any monocyclic, linked bicyclic, or fused bicyclic heteroaryl ring system which has the characteristics of aromaticity in terms of electron distribution throughout the ring system is included in this definition. Typically, the heteroaromatic ring systems contain 3-12 ring carbon atoms and 1 to 5 ring heteroatoms independently selected from oxygen, nitrogen, and sulfur atoms.

The term "substituted heteroaryl" means the above-described heteroaryl is substituted with, for example, one or more, and preferably one or two, substituents which are the same or different which substituents preferably can be halogen, hydroxy, protected hydroxy, thio, alkylthio, cyano, nitro, C1 to C6 alkyl, C1 to C7 substituted alkyl, C1 to C7 alkoxy, C1 to C7 substituted alkoxy, alkoxy-alkyl, C1 to C7 acyl, C1 to C7 substituted acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl)carboxamide, N,N-di(C1 to C6 alkyl)carboxamide, trifluoromethyl, N—((C1 to C6 alkyl)sulfonyl)amino or N-(phenylsulfonyl)amino groups. In many embodiments of substituted heteroaryl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety. Preferably, arylalkyl or heteroarylalkyl is an alkyl group substituted at any position by an aryl group, substituted aryl, heteroaryl or substituted heteroaryl. Preferred groups also include benzyl, 2-phenylethyl, 3-phenylpropyl, 4-phenyl-n-butyl, 3-phenyl-n-amyl, 3-phenyl-2-butyl, 2-pyridinylmethyl, 2-(2-pyridinyl)ethyl, and the like.

The term "substituted arylalkyl" denotes an arylalkyl group substituted on the alkyl portion with one or more, and preferably one or two, groups preferably chosen from halogen, hydroxy, oxo, amino, (monosubstituted)amino, (disubstituted)amino, guanidino, heterocyclic ring, substituted heterocyclic ring, C1 to C6 alkyl, C1 to C6 substituted alkyl, C1 to C7 alkoxy, C1 to C7 substituted alkoxy, alkoxy-alkyl, C1 to C7 acyl, C1 to C7 substituted acyl, C1 to C7 acyloxy, nitro, carboxy, alkoxycarbonyl, carbamoyl, carboxamide, N—(C1 to C6 alkyl)-carboxamide, N,N—(C1 to C6 dialkyl)carboxamide, cyano, N—(C1 to C6 alkylsulfonyl)amino, thiol, C1 to C4 alkylthio, C1 to C4 alkylsulfonyl groups; and/or the phenyl group may be substituted with one or more, and preferably one or two, substituents preferably chosen from halogen, hydroxy, protected hydroxy, thio, alkylthio, cyano, nitro, C1 to C6 alkyl, C1 to C6 substituted alkyl, C1 to C7 alkoxy, C1 to C7 substituted alkoxy, alkoxy-alkyl, C1 to C7 acyl, C1 to C7 substituted acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl) carboxamide, N,N-di(C1 to C6 alkyl)carboxamide, trifluoromethyl, N—((C1 to C6 alkyl)sulfonyl)amino, N-(phenylsulfonyl)amino, cyclic C2 to C7 alkylene or a phenyl group, substituted or unsubstituted, for a resulting biphenyl group. The substituted alkyl or phenyl groups may be substituted with one or more, and preferably one or two, substituents which can be the same or different.

Examples of the term "substituted arylalkyl" include groups such as 2-phenyl-1-chloroethyl, 2-(4-methoxyphenyl)ethyl, 4-(2,6-dihydroxy phenyl)-n-hexyl, 2-(5-cyano-3-methoxyphenyl)-n-pentyl, 3-(2,6-dimethylphenyl)propyl, 4-chloro-3-aminobenzyl, 6-(4-methoxyphenyl)-3-carboxy-n-hexyl, 5-(4-aminomethylphenyl)-3-(aminomethyl)-n-pentyl, 5-phenyl-3-oxo-n-pent-1-yl and the like.

The term "arylalkylene" specifies an arylalkyl, as defined above, where the arylalkyl radical is bonded at two positions connecting together two separate additional groups. The definition includes groups of the formula: -phenyl-alkyl- and alkyl-phenyl-alkyl-. Substitutions on the phenyl ring can be 1,2, 1,3 or 1,4. The term "substituted arylalkylene" is an arylalkylene as defined above that is further substituted preferably by halogen, hydroxy, protected hydroxy, C1 to C4 alkylthio, C1 to C4 alkylsulfoxide, C1 to C4 alkylsulfonyl, C1 to C4 substituted alkylthio, C1 to C4 substituted alkylsulfoxide, C1 to C4 substituted alkylsulfonyl, C1 to C6 alkyl, C1 to C7 alkoxy, C1 to C6 substituted alkyl, C1 to C7 alkoxy-alkyl, oxo, (monosubstituted)amino, (disubstituted)amino, trifluoromethyl, carboxy, alkoxycarbonyl, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties preferably chosen from the groups consisting of halogen, hydroxy, protected hydroxy, thio, alkylthio, cyano, nitro, C1 to C6 alkyl, C1 to C6 substituted alkyl, C1 to C7 alkoxy, C1 to C7 substituted alkoxy, alkoxy-alkyl, C1 to C7 acyl, C1 to C7 substituted acyl, C1 to C7 acyloxy, carboxy, alkoxycarbonyl, carboxymethyl, hydroxymethyl, amino, (monosubstituted)amino, (disubstituted)amino, carboxamide, N—(C1 to C6 alkyl)carboxamide, N,N-di(C1 to C6 alkyl)carboxamide, trifluoromethyl, N—((C1 to C6 alkyl)sulfonyl)amino, N-(phenylsulfonyl)amino or phenyl, wherein the phenyl is substituted or unsubstituted, such that, for example, a biphenyl results. In many embodiments of substituted phenyl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The terms "halo" and "halogen" refer to fluoro, chloro, bromo or iodo atoms or ions. Preferred halogens are chloro and fluoro. Although many of the compounds of the invention having halogen atoms as substituents are highly effective in binding to the relevant Umami taste receptors, such halogenated organic compounds can in some cases have undesirable toxicological properties when administered to an animal in vivo. Therefore, in the various embodiments of the compounds of Formula (I), if a halogen atom (including a fluoro, chloro, bromo, or iodo atom) is listed as a possible substituent, an alternative and preferred group of substituents expressly contemplated hereby would not include the halogen groups.

The term "(monosubstituted)amino" refers to an amino (NHR) group wherein the R group is chosen from the group consisting of phenyl, C6-C10 substituted phenyl, C1 to C6 alkyl, C1 to C6 substituted alkyl, C1 to C7 acyl, C1 to C7 substituted acyl, C2 to C7 alkenyl, C2 to C7 substituted alkenyl, C2 to C7 alkynyl, C2 to C7 substituted alkynyl, C7 to C12 phenylalkyl, C7 to C1 2 substituted phenylalkyl and heterocyclic ring. The (monosubstituted)amino can additionally have an amino-protecting group as encompassed by the term "protected (monosubstituted)amino."

The term "(disubstituted)amino" refers to an amino group (NR2) with two substituents independently chosen from the group consisting of phenyl, C6-C10 substituted phenyl, C1 to C6 alkyl, C1 to C6 substituted alkyl, C1 to C7 acyl, C2 to C7 alkenyl, C2 to C7 alkynyl, C7 to C1 2 phenylalkyl, and C7 to C 12 substituted phenylalkyl. The two substituents can be the same or different.

The term "alkylthio" refers to —SR groups wherein R is an optionally substituted C1-C7 or C1-C4 organic group, preferably an alkyl, cycloalkyl, aryl, or heterocyclic group, such as methylthio, ethylthio, n-propylthio, isopropylthio, n-butylthio, t-butylthio and like groups.

The term "alkylsulfoxide" indicates —$SO_2R$ groups wherein R is an optionally substituted C1-C7 or C1-C4 organic group, preferably an alkyl, cycloalkyl, aryl, or heterocyclic group, such as methylthio, ethylthio, n-propylthio, isopropylthio, n-butylthio, t-butylthio and like groups, such as methylsulfoxide, ethylsulfoxide, n-propylsulfoxide, isopropylsulfoxide, n-butylsulfoxide, sec-butylsulfoxide and the like.

The term "alkylsulfonyl" indicates —S(O)R groups wherein R is an optionally substituted C1-C7 or C1-C4 organic group, which include for example groups such as methylsulfonyl, ethylsulfonyl, n-propylsulfonyl, isopropylsulfonyl, n-butylsulfonyl, t-butylsulfonyl and the like.

The terms "phenylthio," "phenylsulfoxide," and "phenylsulfonyl" specify a sulfoxide (—S(O)—R), or sulfone (—$SO_2R$) wherein the R group is a phenyl group. The terms "substituted phenylthio," "substituted phenylsulfoxide," and "substituted phenylsulfonyl" means that the phenyl of these groups can be substituted as described above in relation to "substituted phenyl."

The term "alkoxycarbonyl" means an "alkoxy" group attached to a carbonyl group, (i.e. a carboxylic acid ester, —C(O)—OR, wherein R is preferably an alkyl group, preferably a $C_1$-C4 alkyl group. The term "substituted alkoxycarbonyl" denotes a substituted alkoxy bonded to the carbonyl group, which alkoxy may be substituted as described above in relation to substituted alkyl.

The term "phenylene" means a phenyl group where the phenyl radical is bonded at two positions connecting together two separate additional groups. Examples of "phenylene" includes 1,2-phenylene, 1,3-phenylene, and 1,4-phenylene.

The term "substituted alkylene" means an alkyl group where the alkyl radical is bonded at two positions connecting together two separate additional groups and further bearing an additional substituent. Examples of "substituted alkylene" includes aminomethylene, 1-(amino)-1,2-ethyl, 2-(amino)-1, 2-ethyl, 1-(acetamido)-1,2-ethyl, 2-(acetamido)-1,2-ethyl, 2-hydroxy-1,1-ethyl, 1-(amino)-1,3-propyl.

One or more of the compounds of the invention, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as nitrogen containing heterocycles or amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to positively charged counter-ions for the carboxylate anion of a carboxylate salt. Inorganic positively charged counter-ions include but are not limited to the alkali and alkaline earth metals, (such as lithium, sodium, potassium, calcium, magnesium, etc.) and other divalent and trivalent metallic cations such as barium, aluminum and the like, and ammonium $(NH4)^+$ cations. Organic cations include ammonium cations derived from acid treatment or alkylation of primary-, secondary-, or tertiary amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge, et al., J. Pharm. Sci. (1977) 66:1-19, which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R^2$ or $R^3$ is substituted with a (quaternary ammonium)methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

A residue or radical of a chemical species, as used in the specification and concluding claims, refers to a structural fragment, or a moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —$OCH_2CH_2O$— repeat units in the polyester, regardless of whether ethylene glycol is used to prepare the polyester.

The term "organic residue" or "organic radical" defines a carbon containing residue or radical, comprising at least one carbon atom. Organic residues can contain one or more heteroatoms, or be bonded to another molecule through a heteroatom, including oxygen, nitrogen, sulfur, phosphorus, or the like. Examples of organic residues include but are not limited alkyl or substituted alkyls, alkoxyls or substituted alkoxyls, hydroxyalkyls and alkoxyalkyls, cycloalkyl or substituted cycloalkyls, cycloalkenyl or substituted cycloalkenyls, heterocycles and substituted heterocycles, aryls and substituted aryls, heteroaryls and substituted heteroaryls, mono or di-substituted amino, amide groups, CN, $CO_2H$, CHO, $COR^{40}$, $CO_2R'$, SR' wherein R' is an alkyl, and the like. Examples of species of organic groups or residues include but are not limited to $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, trifluoromethoxy, phenyl, phenoxyl, and pyridyl groups or residues, and the like. Organic residues can comprise 1 to 18 carbon atoms, 1 to 15, carbon atoms, 1 to 12 carbon atoms, 1 to 8 carbon atoms, or 1 to 4 carbon atoms.

By the term "effective amount" of a compound as provided herein is meant a sufficient amount of the compound to provide the desired regulation of a desired function; such as protein function, or the induction of a particular type of taste perception. As will be pointed out below, the exact amount required will vary from subject to subject, depending on the species, age, general condition of the subject, specific identity and formulation of the comestible composition, etc. Thus, it is not possible to specify an exact "effective amount." However, an appropriate effective amount can be determined by one of ordinary skill in the art using only routine experimentation.

The term "therapeutically effective amount" means the amount of a compound as provided herein that, when administered to a patient for treating a disease, is sufficient to effect such treatment for the disease. The "therapeutically effective amount" will vary depending on the compound, the disease and its severity and the age, weight, etc., of the patient to be treated. When the present compound is in a pharmaceutical composition, it can be in a therapeutically effective amount, or alternatively, not in a therapeutically effective amount. In other words, when the present compound is in a pharmaceutical composition, it can be either an active ingredient or inactive ingredient.

"Vehicle" refers to a diluent, adjuvant, excipient or carrier with which a compound is administered.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds. Furthermore, "a compound of the present invention", "the present compound", or "the compound of the present invention" refers to any compound and compounds covered by the generic formula (I) and/or any subgenus thereof including racemic mixtures, diastereomers, enantiomers, tautomers, or any other isomers and analogs (such as N-oxide) thereof as well as salts, solvates (such as, e.g., hydrate), esters, and/or prodrugs thereof.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyls where there is substitution.

Compounds of the Present Invention

In one aspect, the present invention provides a compound having structural formula (I)

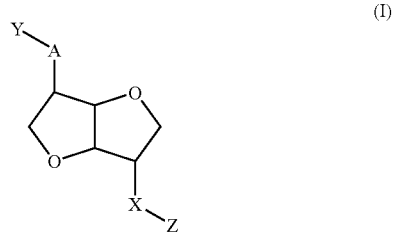

(I)

or the salt, solvate, N-oxide, ester, and/or prodrug thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —$NO_2$, —$OR^1$, —$S(O)R^1$, —S(O)₂R¹, —OC(O)R¹, —N(R¹)C(O)R², —NR¹R², —C(O)NR¹R², —C(O)OR¹, —S(O)₂NR¹R², —COR¹, —N(R¹)S(O)₂R², —SR¹, —C(R¹R²R⁶), —C(S)—R¹, —C(=NR²)—R¹, —N(R¹)—C(=N—OR²)R⁶, —N(R¹)C(S)NR²R⁶, —C(=N—OR¹)R², —C(=NR¹)—NR²R⁶, —N(R¹)C(=NR²)NR⁶R⁷, —N(R¹)C(S)R², —N(R¹)—C(O)—C(O)R², —C(S)—NR¹R², —N(R¹)C(=NR²)OR⁶, —C(=NR¹)O—NR²R⁶, —N(R¹)N(R²)C(O)OR⁶, —N(R¹)C(O)OR², —N(R¹)C(O)NR²R⁶, —N(R¹)—C(O)—C(O)—NR²R⁶, —C(O)—C(O)—NR¹R², —P(O)(OR¹)(OR²), —P(O)(OR¹)(R²), or —P(O)R¹R²;

X is —O—, —S—, —S(O)—, —S(O)₂—, —C(R³R⁴)—, —C(O)—, —C(S)—, —C(=NR³)—, —C(O)O—, —N(R³)—, —OC(O)—, —N(R³)C(O)—, —C(O)N(R³)—, —N(R³)—C(=N—OR⁴)—, —C(=N—OR³)—, —C(=NR³)—NR⁴—, —N(R³)C(S)N(R⁴)—R⁵, —N(R³)C(O)N(R⁴)—R⁵, —N(R³)C(=NR⁴)—, —N(R³)C(S)—, —N(R³)—C(O)—C(O)—, —C(S)—N(R³)—, —N(R³)S(O)₂—, —S(O)₂—N(R³)—, —N(R³)C(=NR⁴)O—, —C(=NR⁴)O—N(R³)—, —N(R³)—C(=NR⁴)—N(R⁵)—, —N(R³)N(R⁴)C(O)O—, —N(R³)C(O)O—, —N(R³)C(O)N(R⁴)—, —N(R³)—C(O)—C(O)—NR⁴—, —C(O)—C(O)—NR⁴—, —P(O)(OR³)—, or —P(O)R³—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl;

R¹, R², R³, R⁴, R⁵, R⁶, and R⁷ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; and with the following provisos: (a) when A is triazole or tetrazole; then —X-Z is not —O-alkyl, —O-acyl, or sulfonamido; (b) when A is tetrazole, and Z is cyclohexyl; then X is not —NH—C(O)—, —NH—C(O)—NH—; and (c) when A is a covalent bond, then Y is not hydrogen.

In one embodiment of the compound of formula (I), Y is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl. In another embodiment of the compound of formula (I), Y is alkyl, substituted alkyl, aryl, substituted aryl, arylalkyl, substituted arylalkyl, carbocyclyl, or substituted carbocyclyl.

In one embodiment of the compound of formula (I), A is monocyclic five- or six-membered heteroaryl. In another embodiment of the compound of formula (I), A has a structural formula selected from the group consisting of:

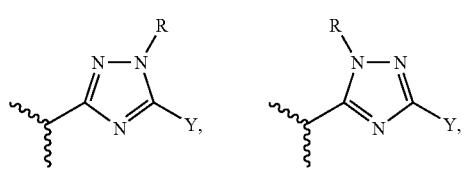

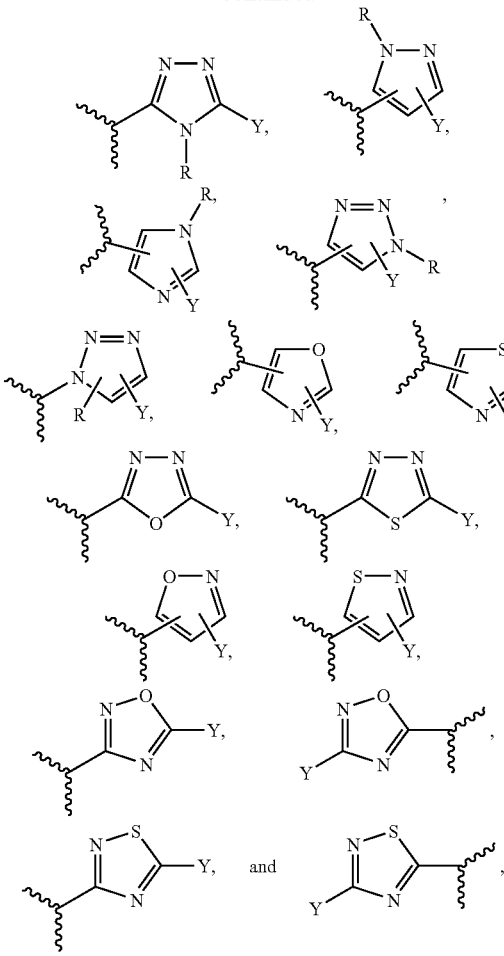

wherein

R is each independently selected from the group consisting of hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, carbocyclyl, or substituted carbocyclyl; and R⁶ and R⁷ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

In one embodiment of the compound of formula (I), A is monocyclic five-membered heteroaryl; Y is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —C(=N—OR$^3$)—, —C(=NR$^3$)—NR$^4$—, —N(R$^3$)C(=NR$^4$)—, —N(R$^3$)C(S)—, —C(S)—N(R$^3$)—, —N(R$^3$)S(O)$_2$—, —S(O)—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —NR$^3$—C(O)—C(O)—NR$^4$—, —C(O)—C(O)—NR$^4$—, —P(O)(OR$^3$)—, or —P(O)(R$^3$)—; Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; and R$^3$, R$^4$, and R$^5$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, carbocyclyl, or substituted carbocyclyl.

In one embodiment, the compound of formula (I) has a structural formula (Ia),

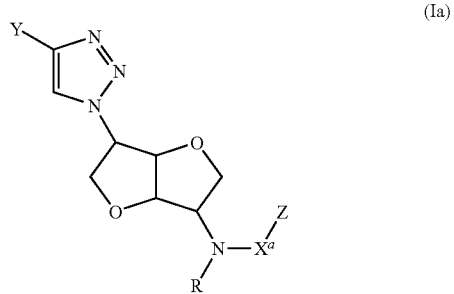

(Ia)

or the salt, solvate, or N-oxide thereof, wherein

X$^a$ is —S(O)—, —S(O)$_2$—, —C(R$^3$R$^4$)—, —C(O)—, —C(O)O—, —C(O)N(R$^3$)—, —C(=N—OR$^3$)—, —C(=NR$^3$)—NR$^4$—, —C(=NR$^3$)—, —C(S)—N(R$^3$)—, —C(S)—, —NR$^3$—C(O)—C(O)—NR$^4$—, —C(O)—C(O)—NR$^4$—, or —S(O)$_2$—N(R$^3$)—;

Y is alkyl, substituted alkyl, aryl, substituted aryl, arylalkyl, substituted arylalkyl, carbocyclyl, or substituted carbocyclyl;

Z is alkyl, substituted alkyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl; and R hydrogen, alkyl, or substituted alkyl.

In one embodiment of the compound of formula (Ia), Z is alkyl, or substituted alkyl.

In one embodiment of the compound of formula (Ia), Z is aryl, or substituted aryl.

In one embodiment of the compound of formula (Ia), Z is heteroaryl, or substituted heteroaryl.

In one embodiment of the compound of formula (Ia), Z is carbocyclyl, or substituted carbocyclyl.

In another embodiment, the present invention provides a compound having a structural formula selected from the group consisting of

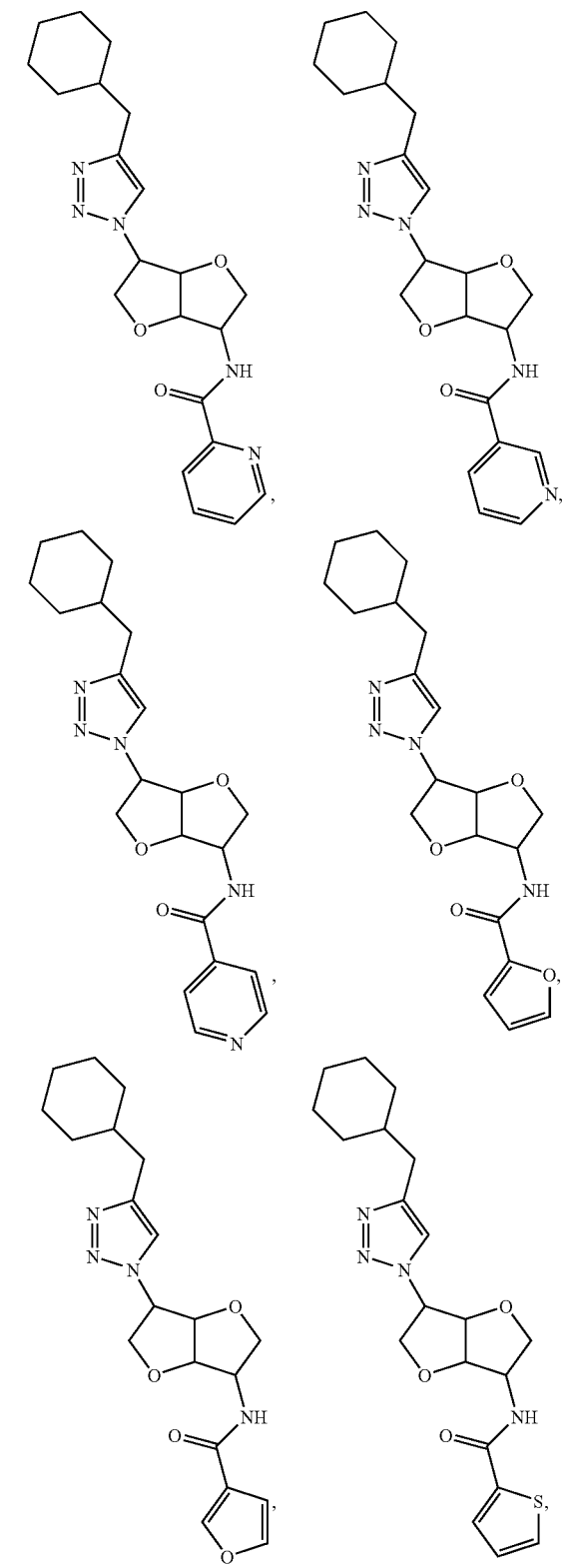

23
-continued
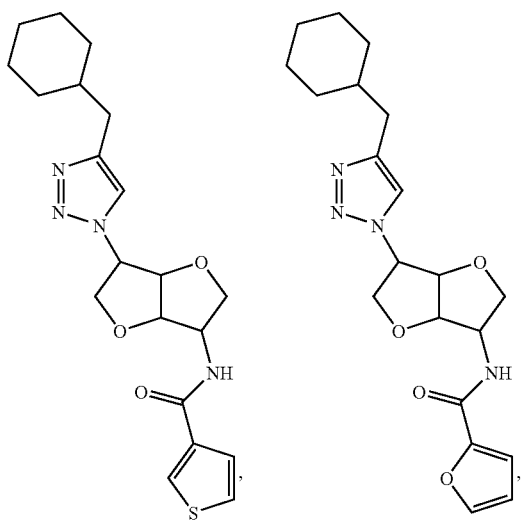
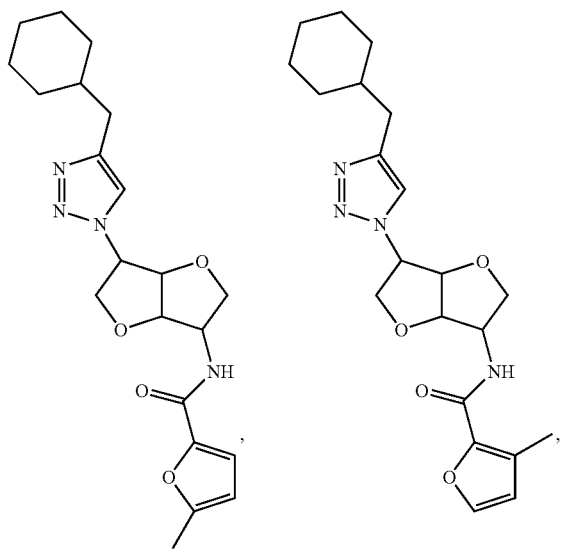
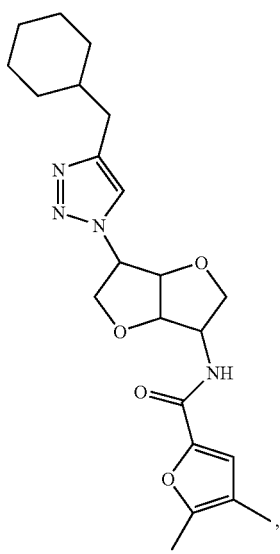
24
-continued
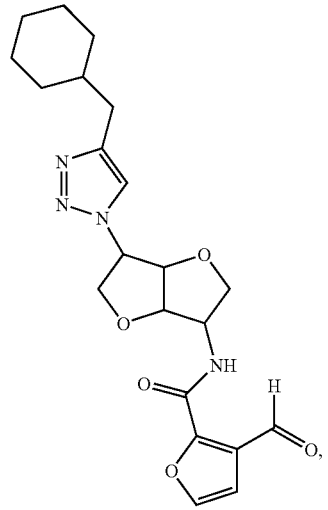
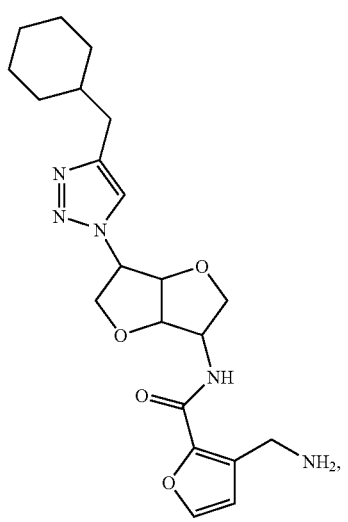
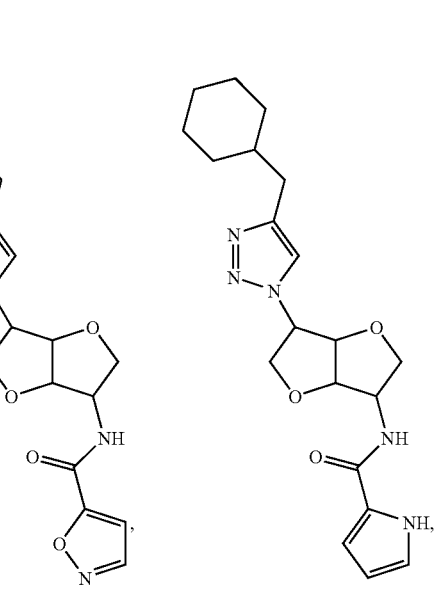

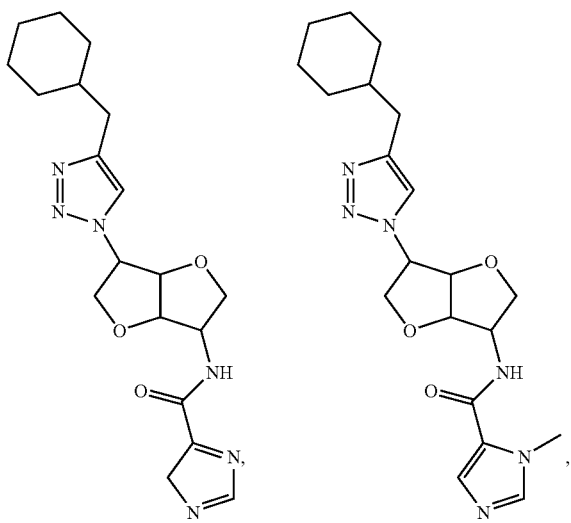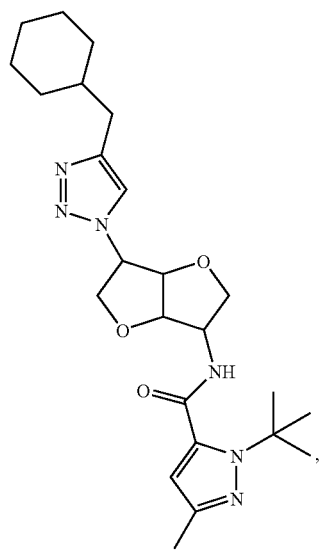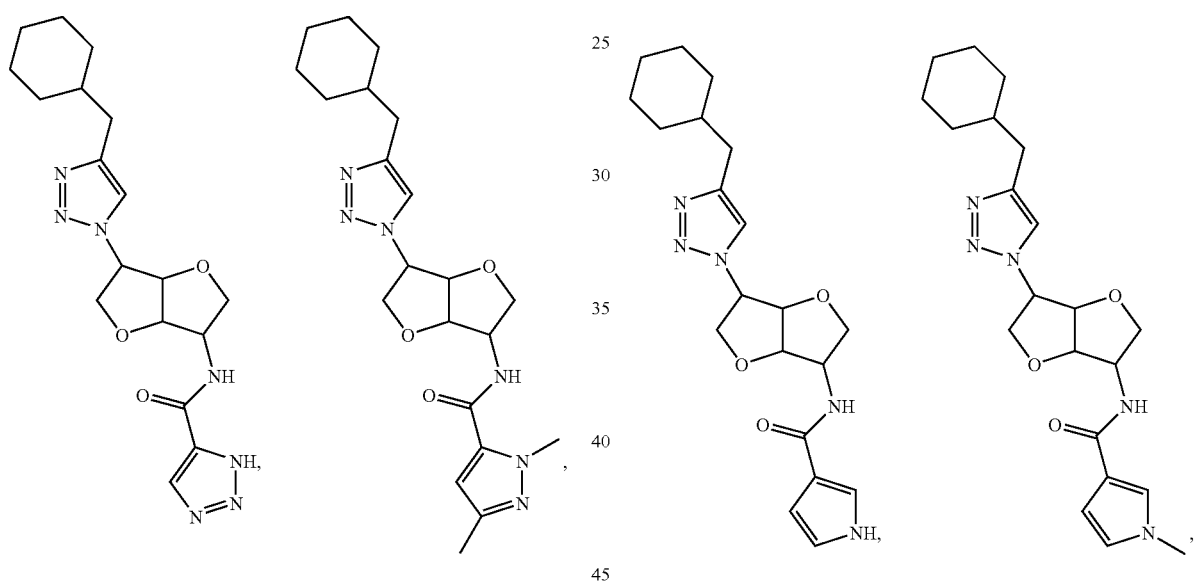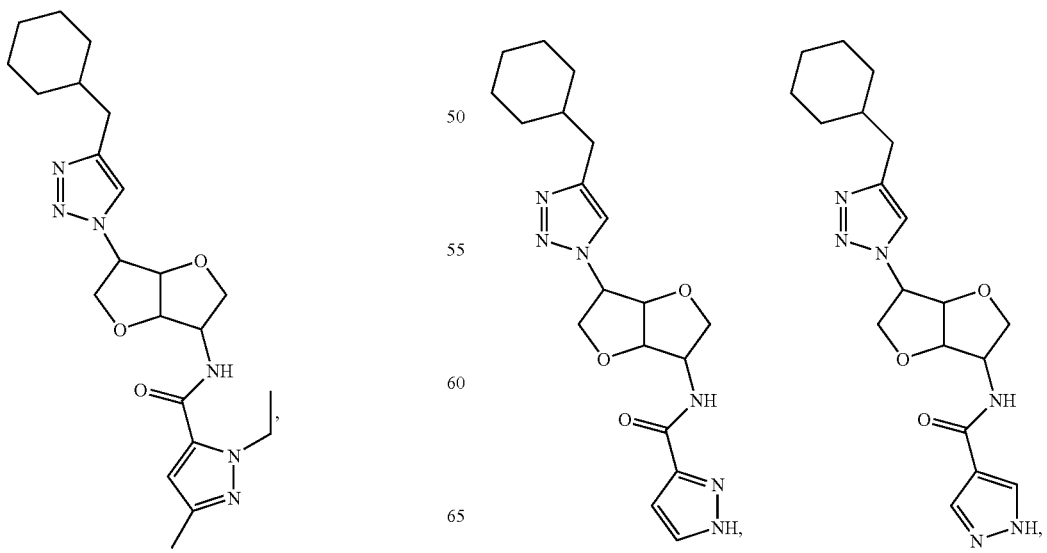

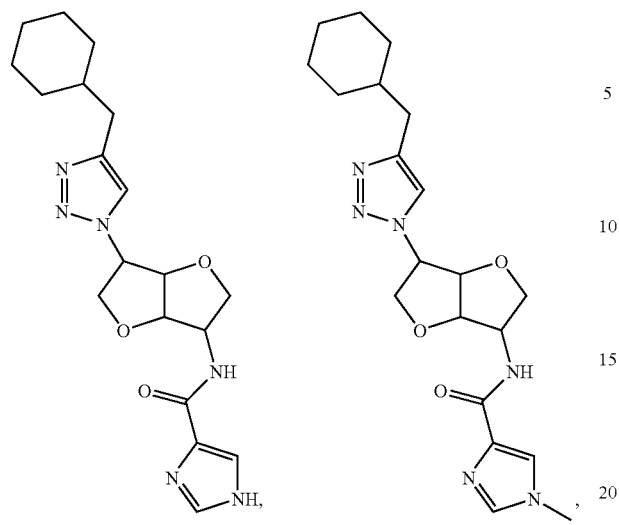
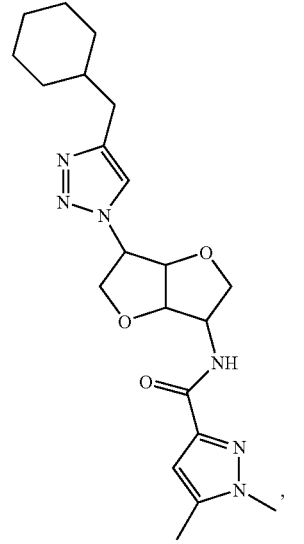
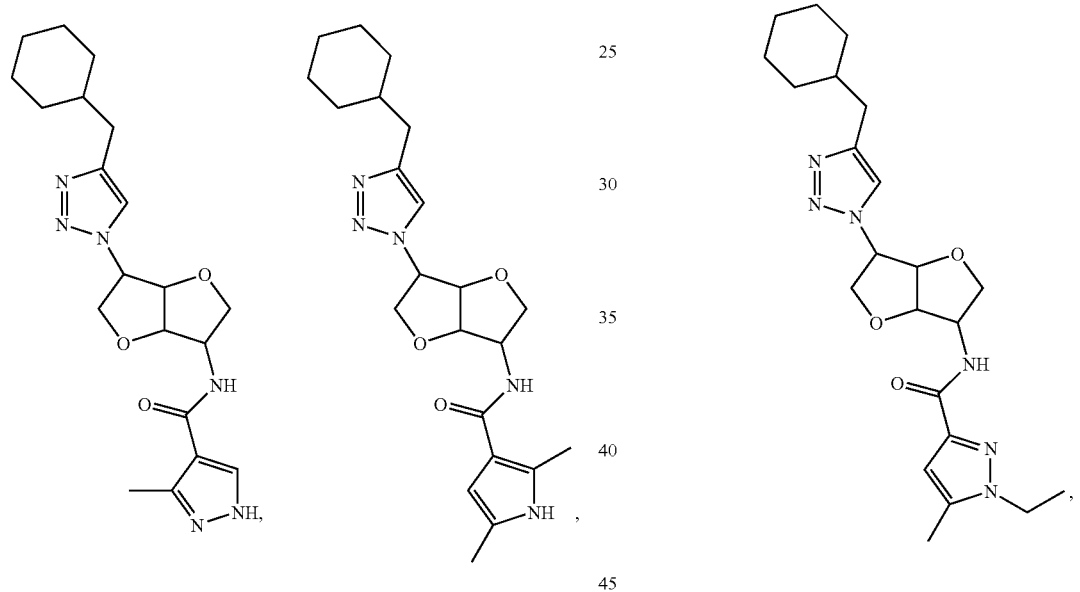
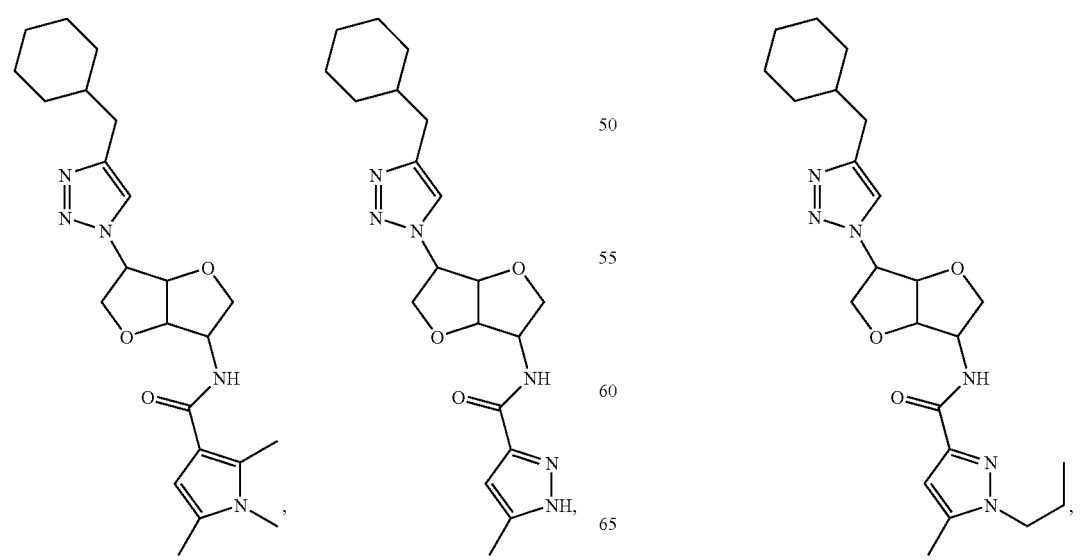

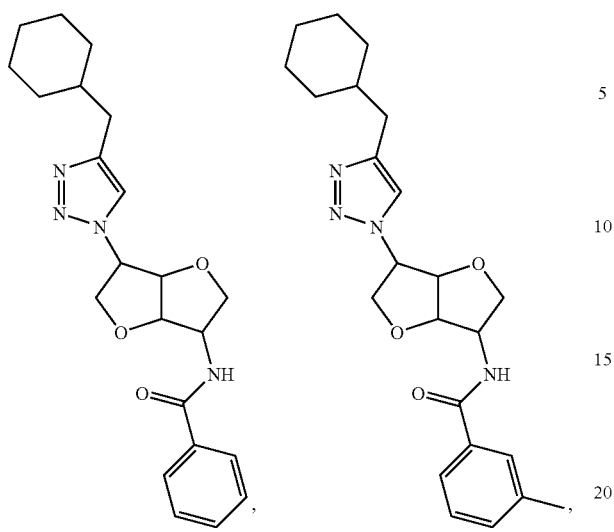
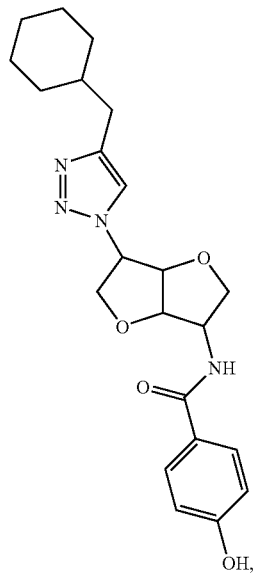
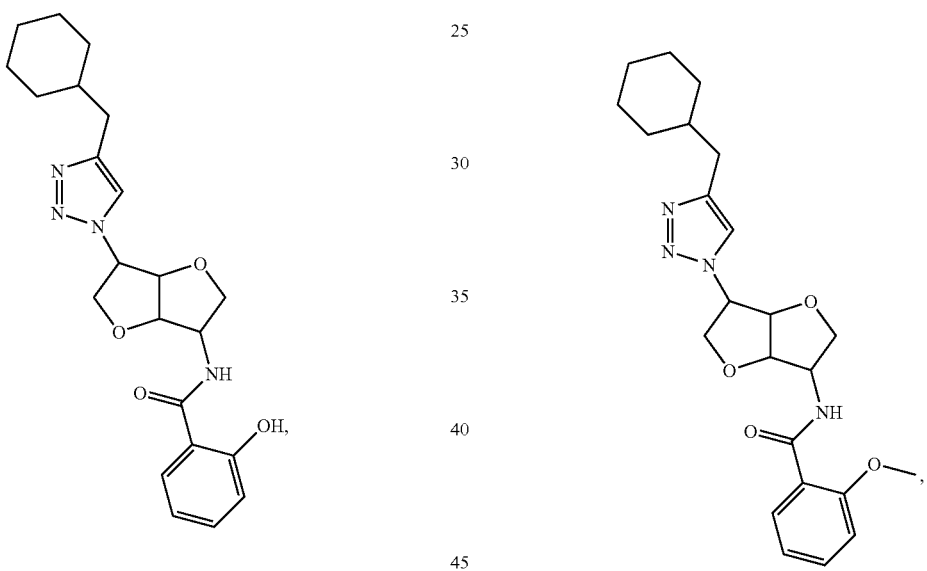
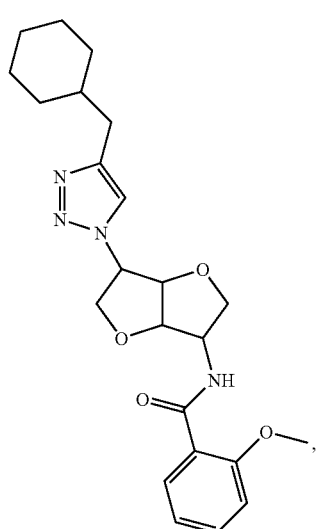
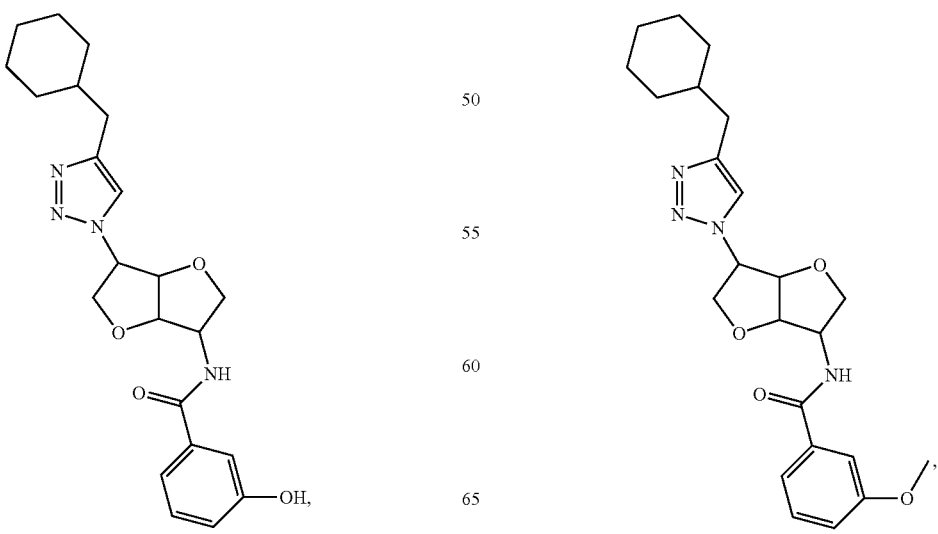
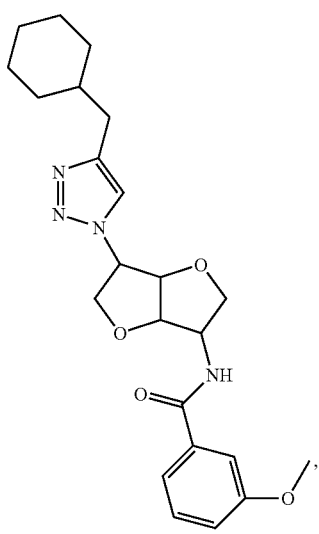

31
-continued
32
-continued
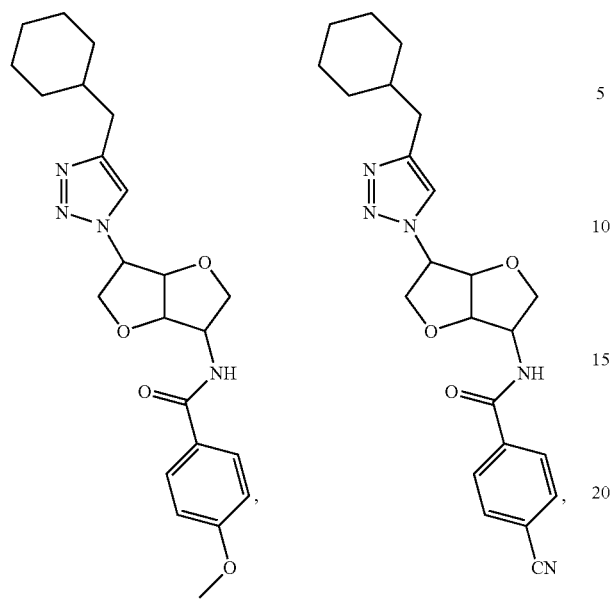
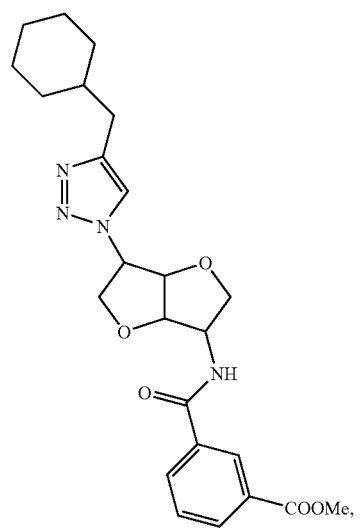
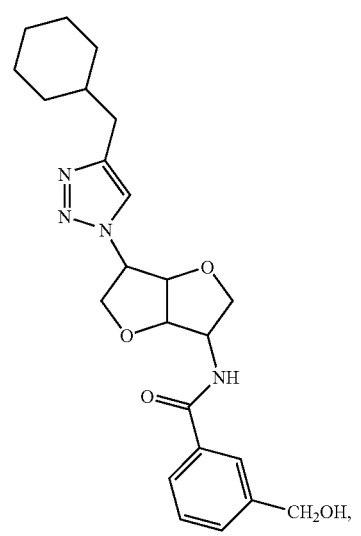
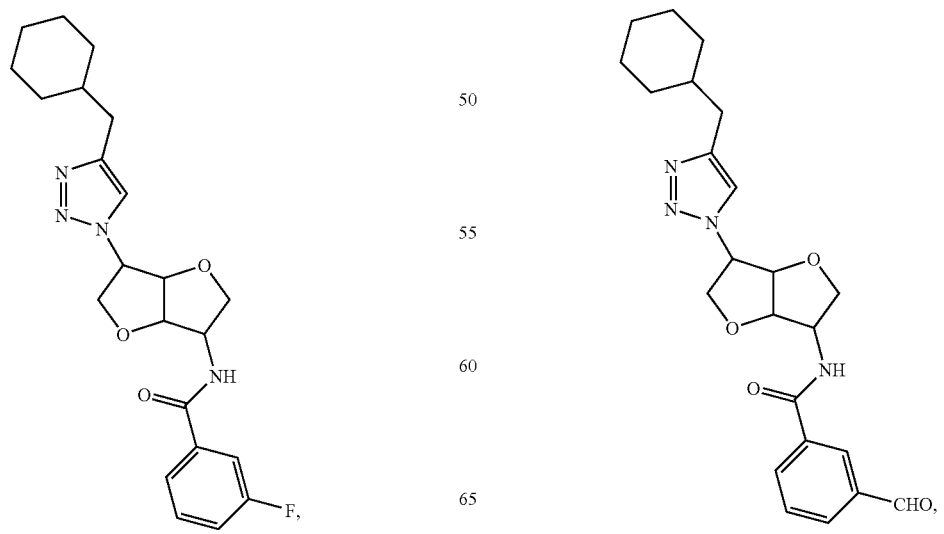

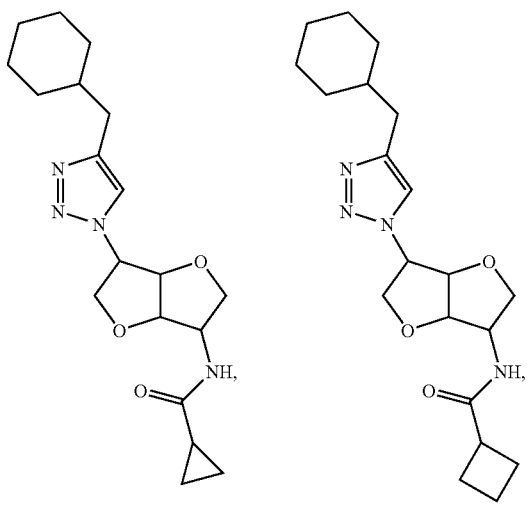
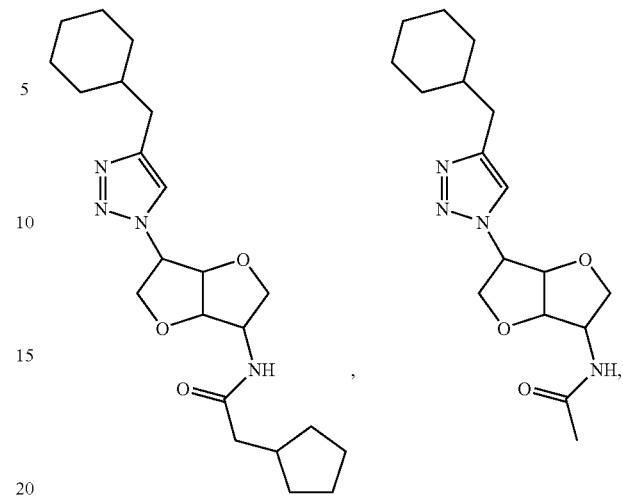
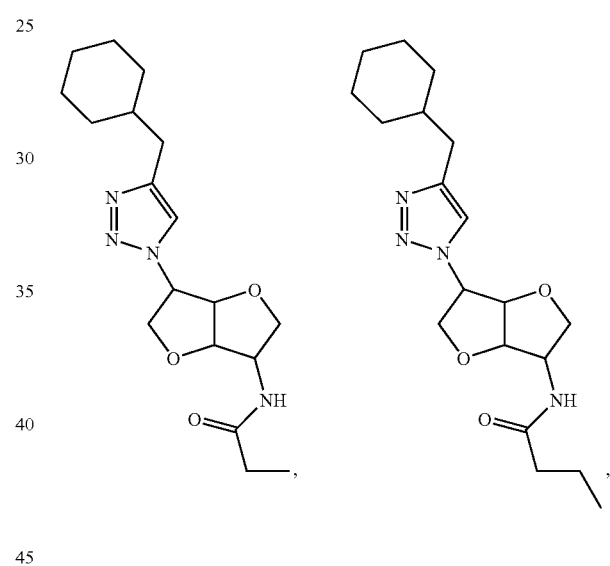
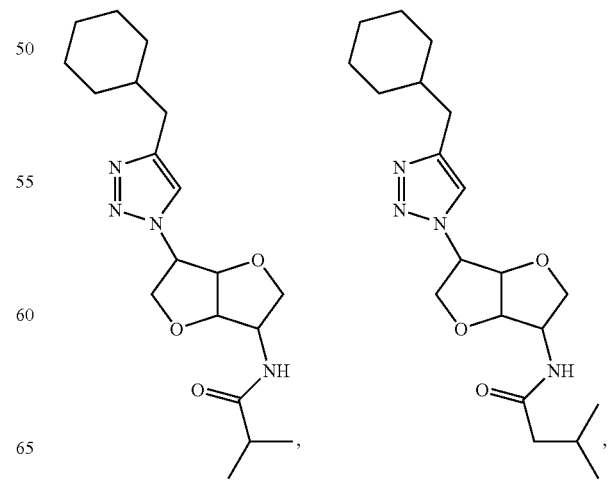

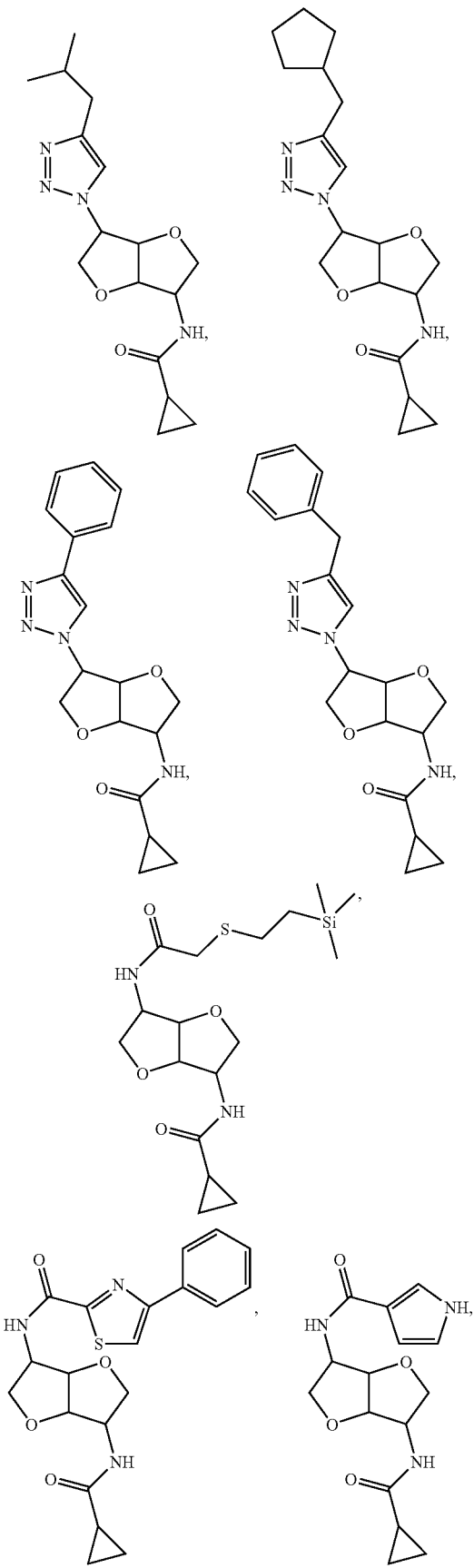
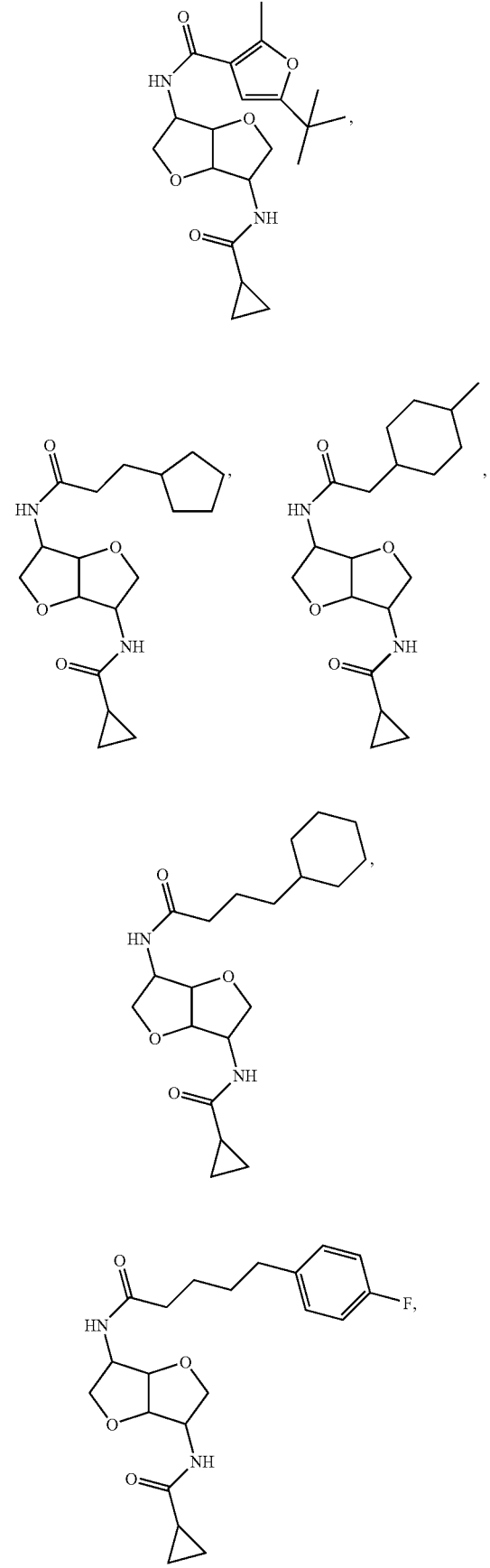

37
-continued
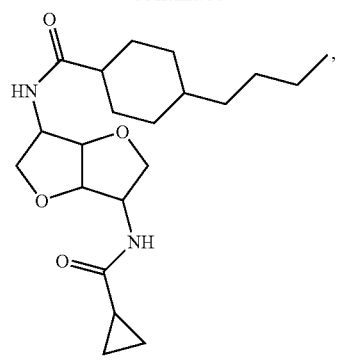
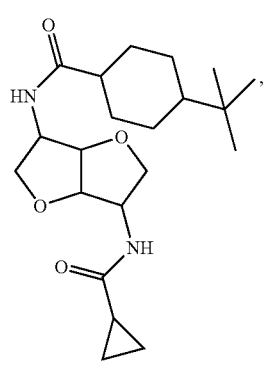
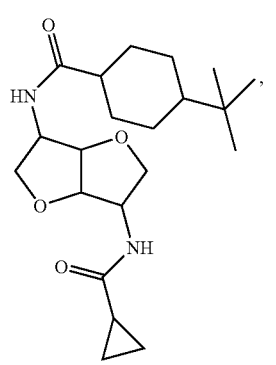
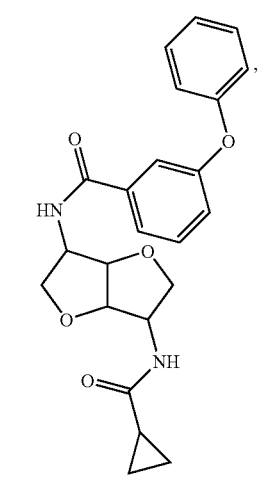
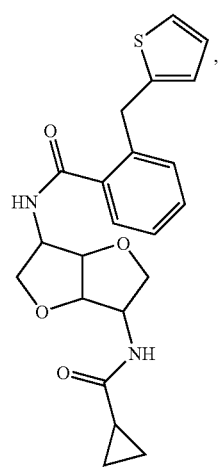
38
-continued
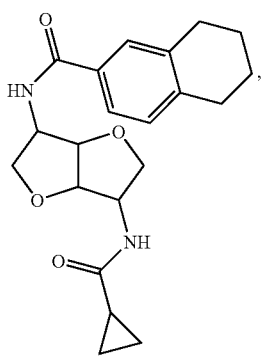
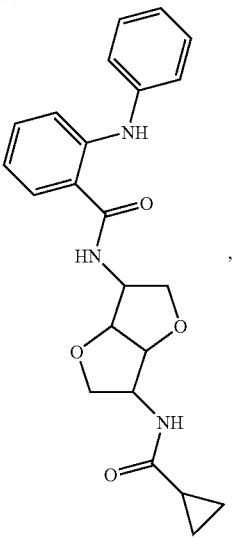
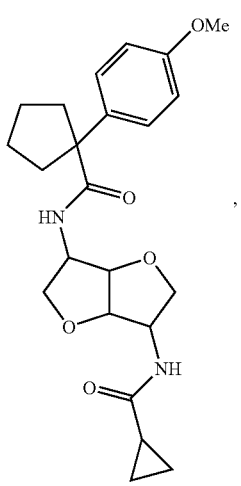
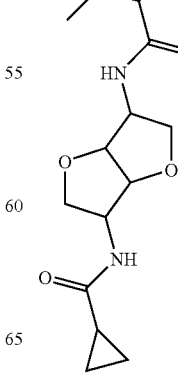
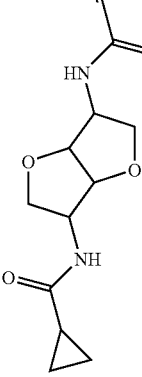
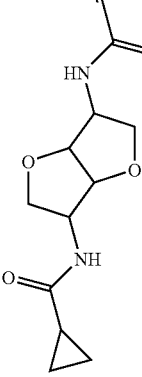
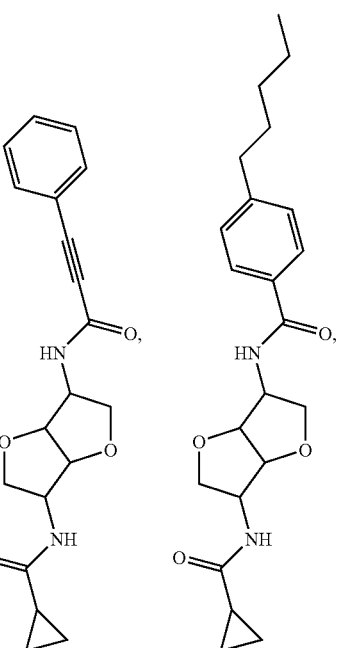

39
-continued
40
-continued
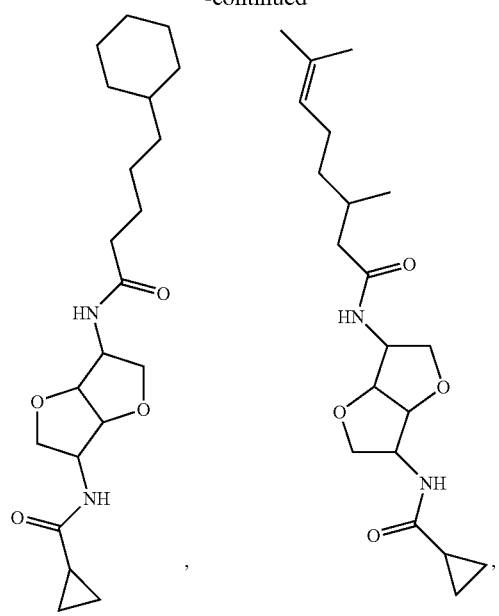
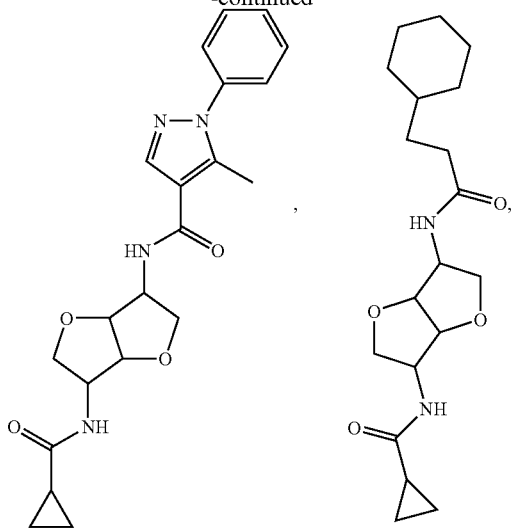
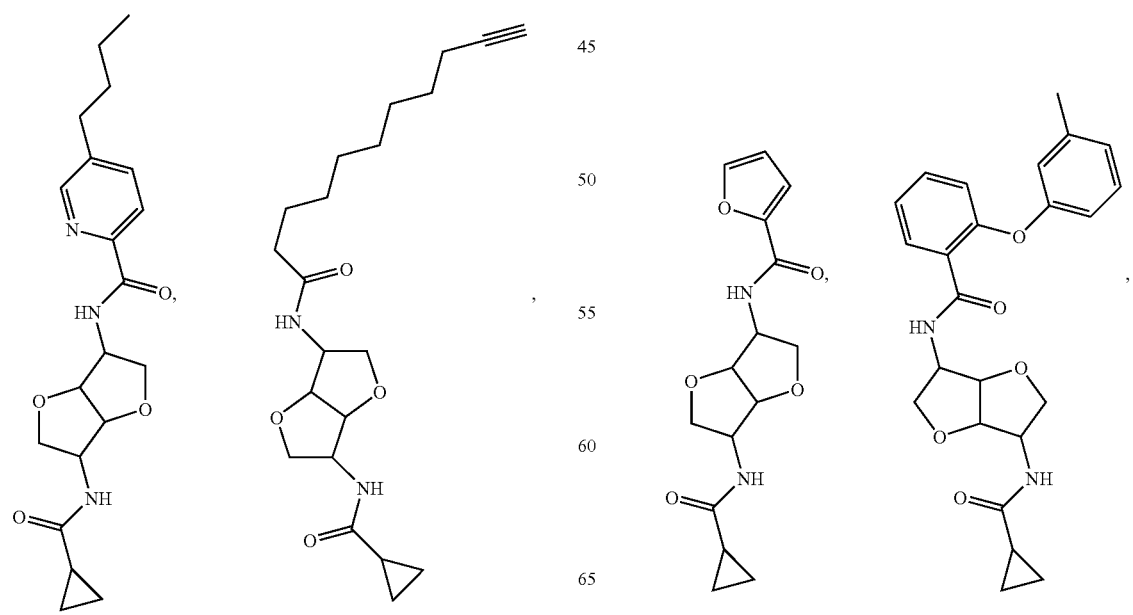

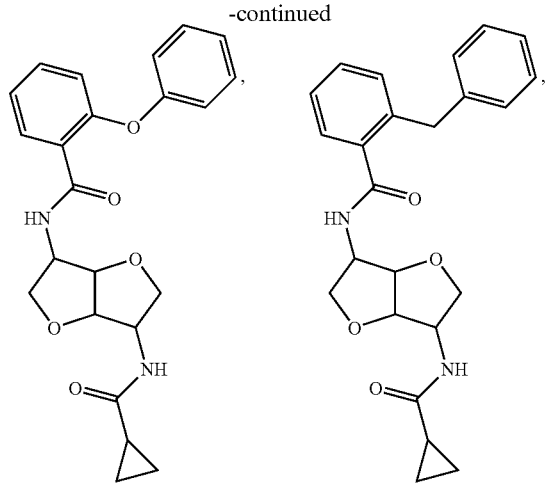
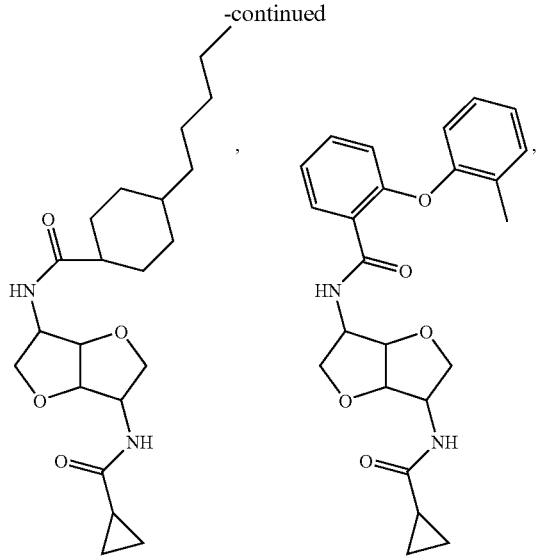
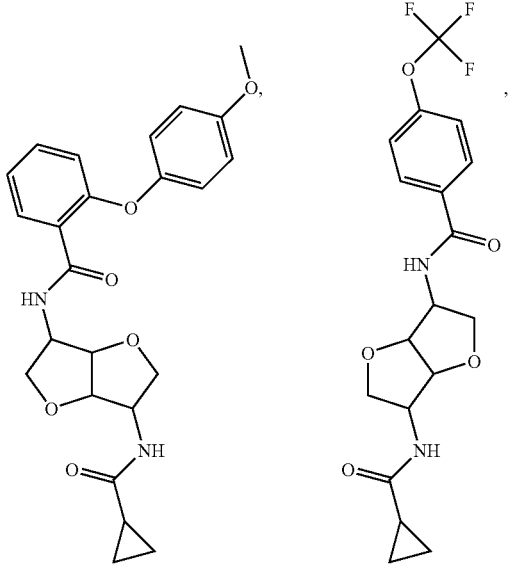
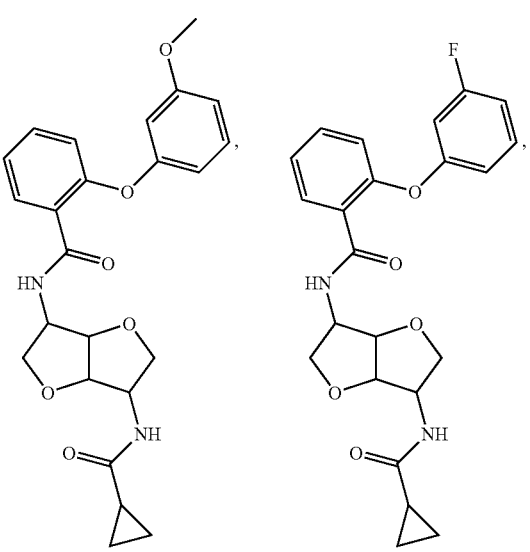

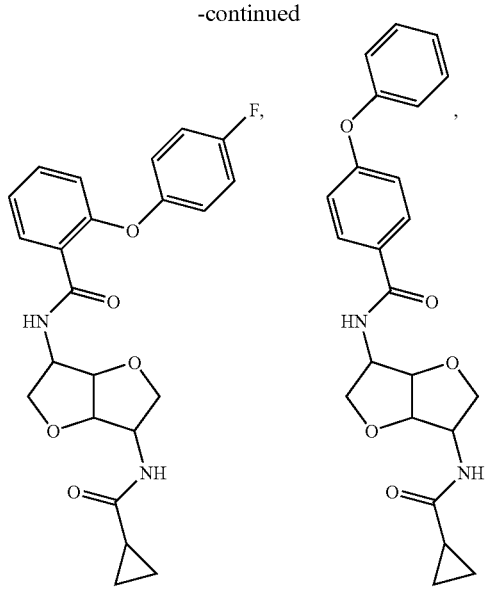
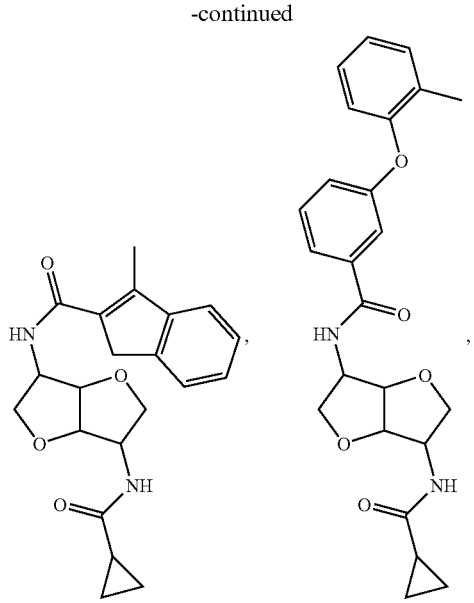
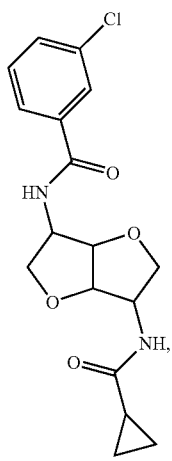
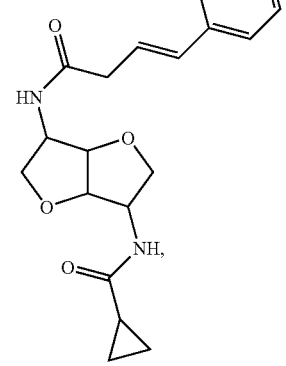
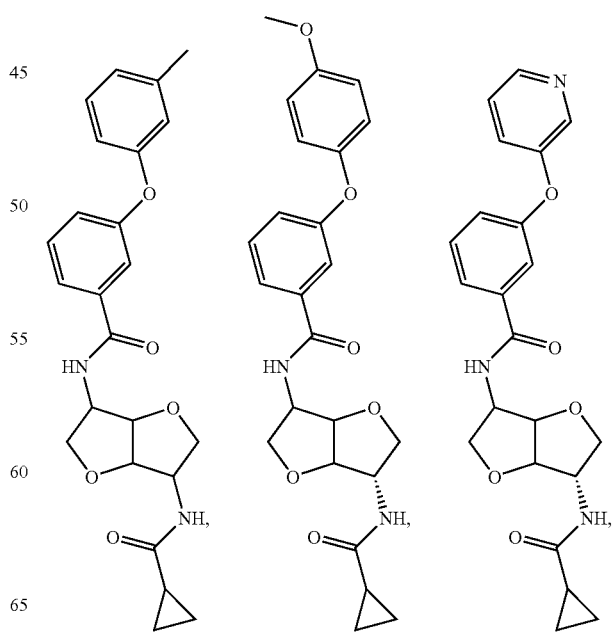

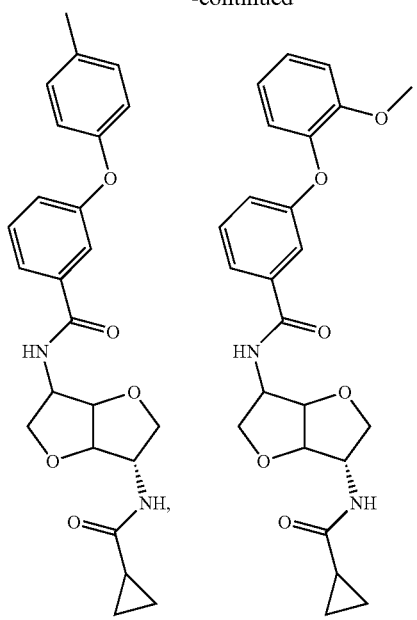
, and
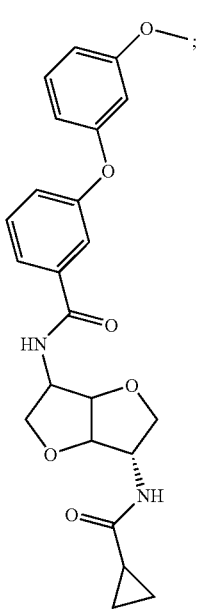
or the salt, solvate, N-oxide, ester, and/or prodrug thereof.
Preferably, the present invention provides a compound having a structural formula selected from the group consisting of
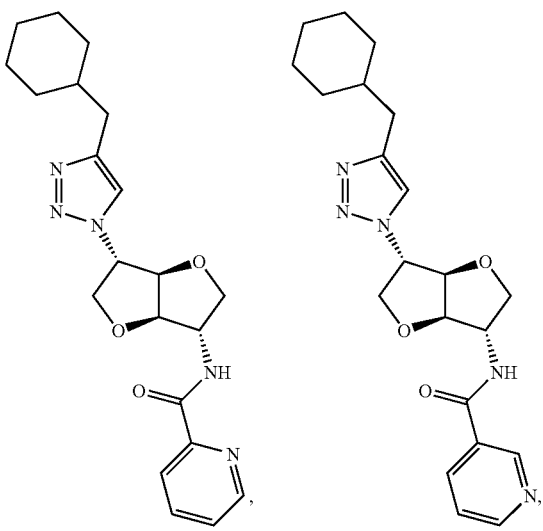
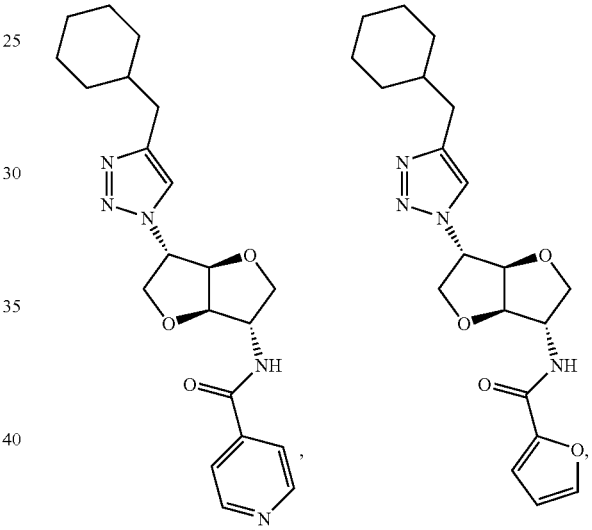
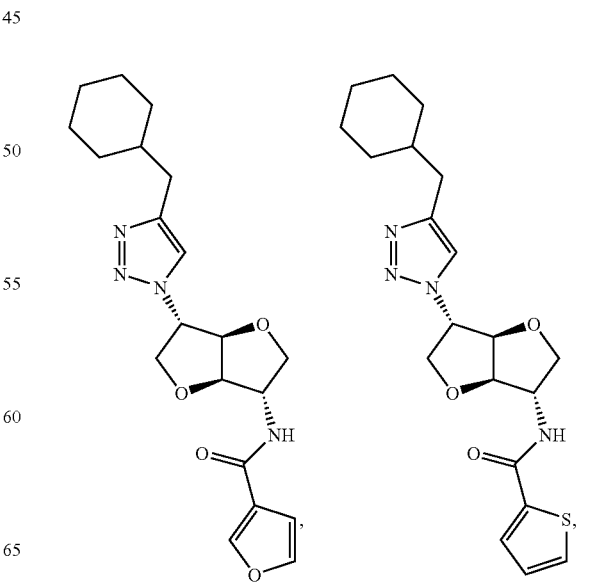

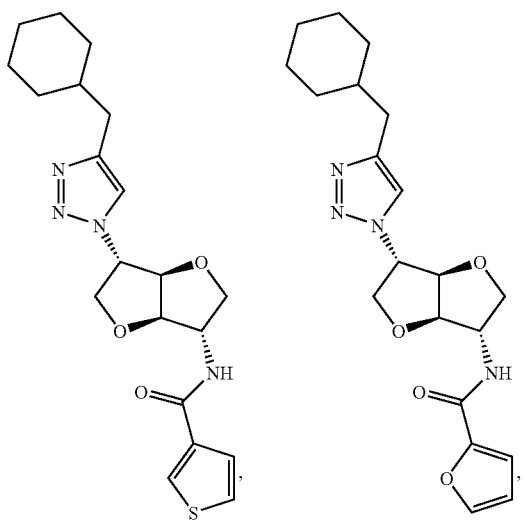
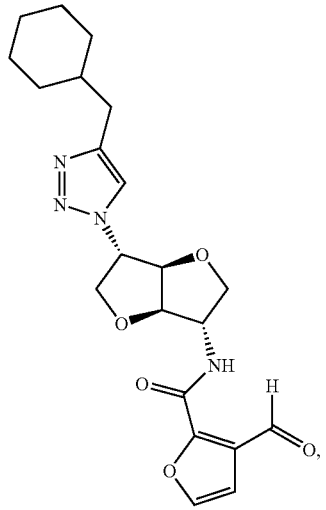
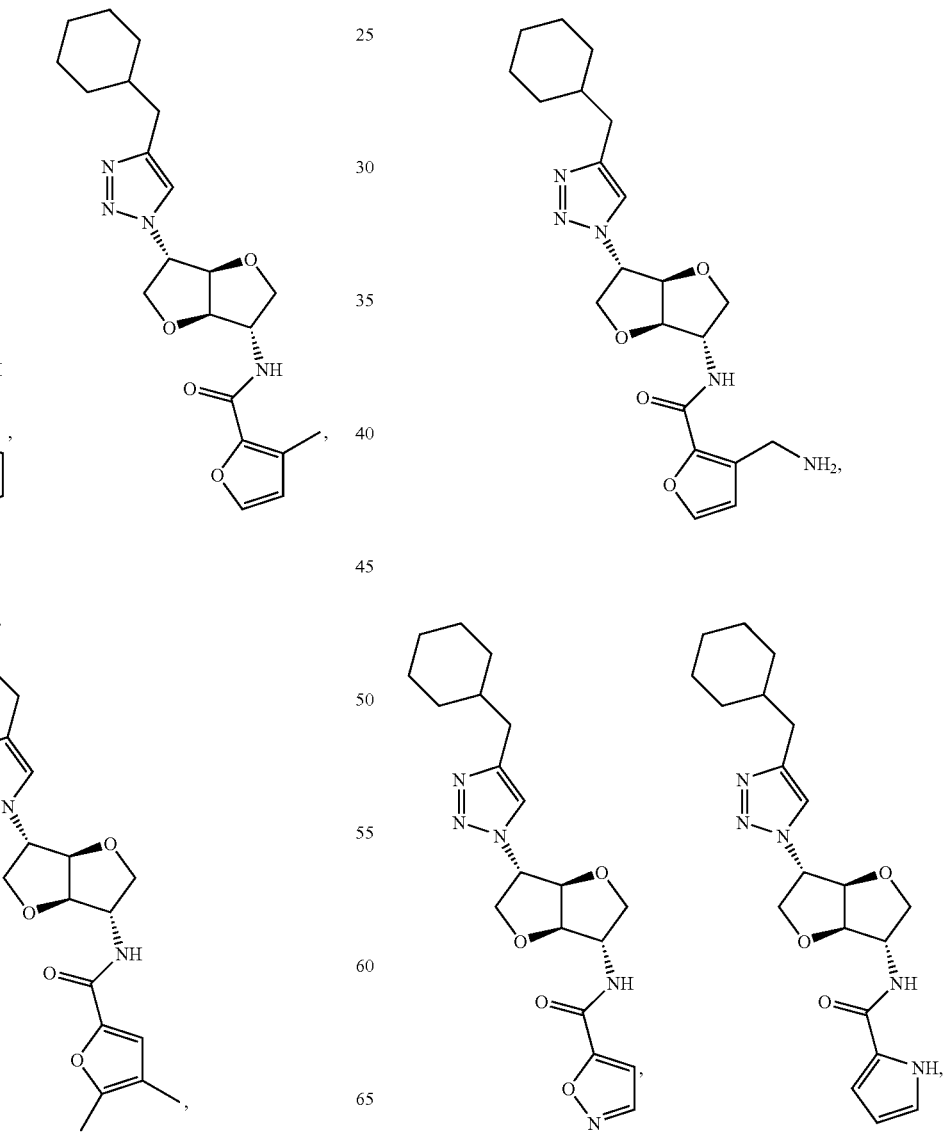

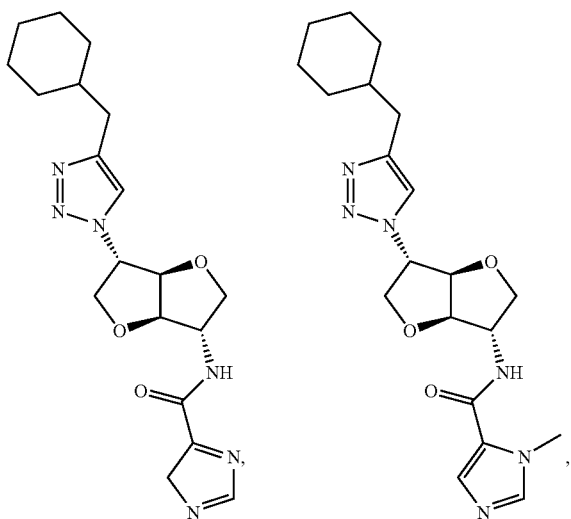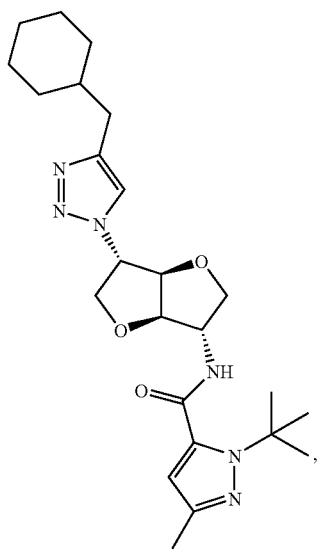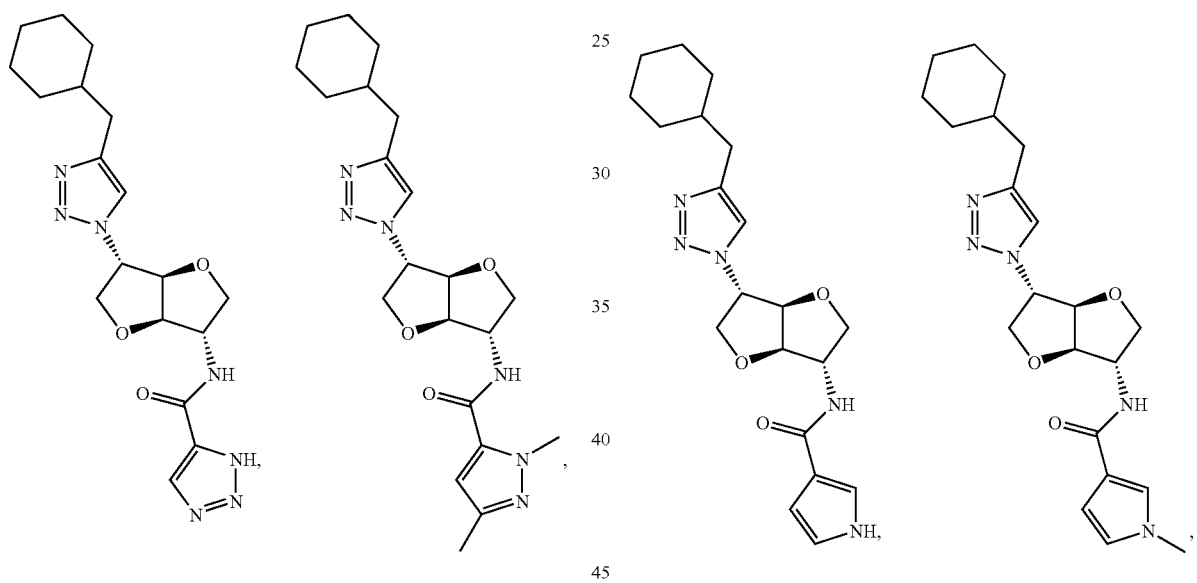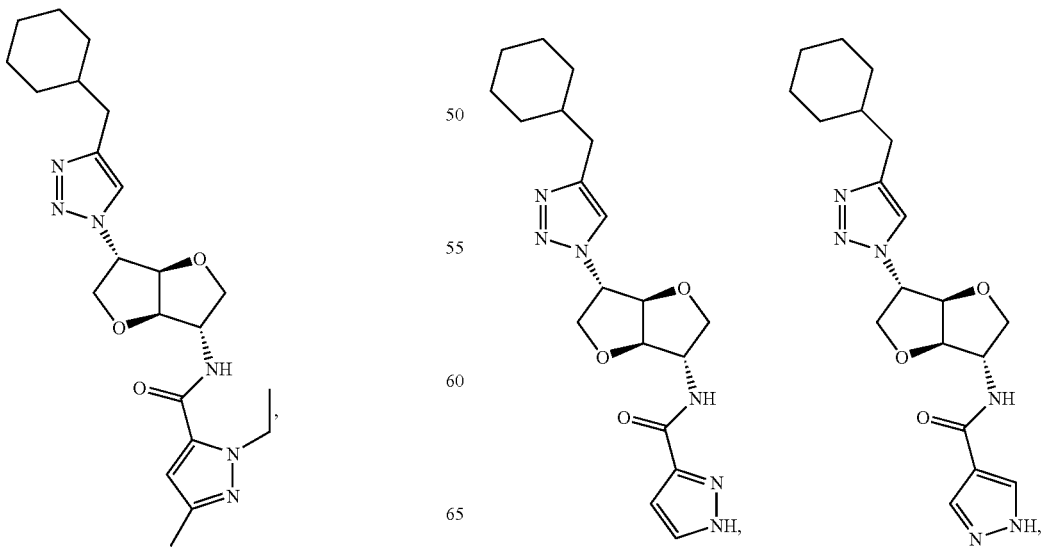

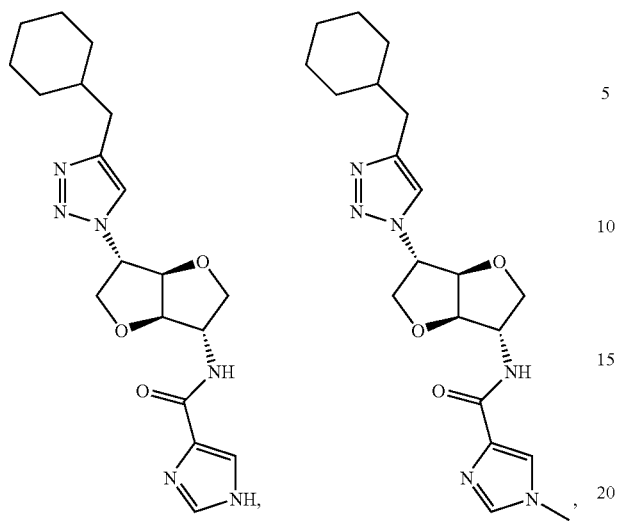
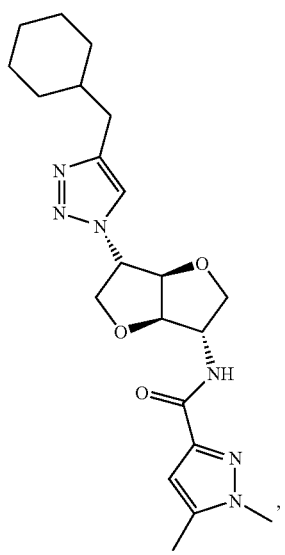
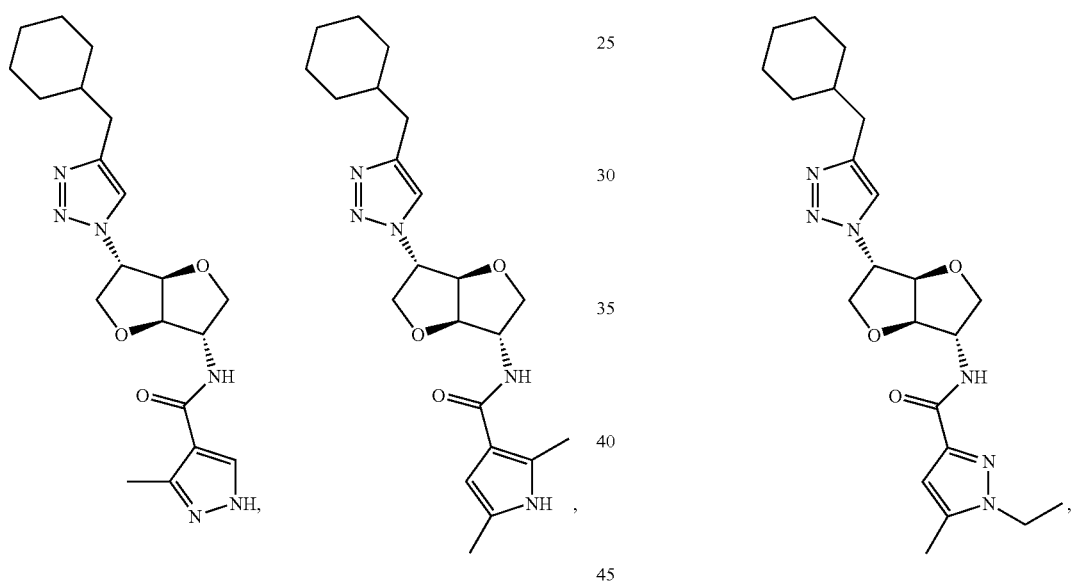
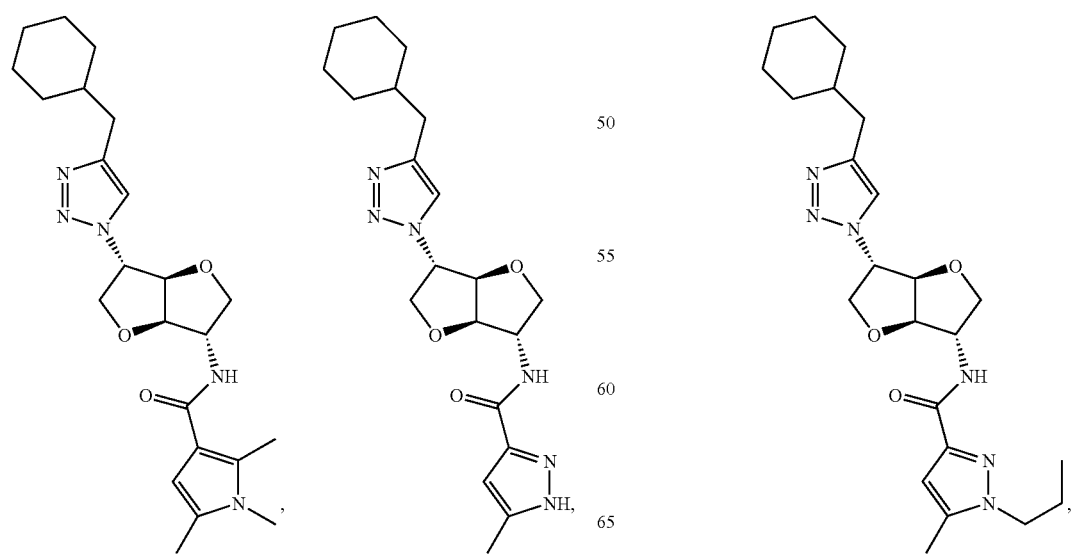

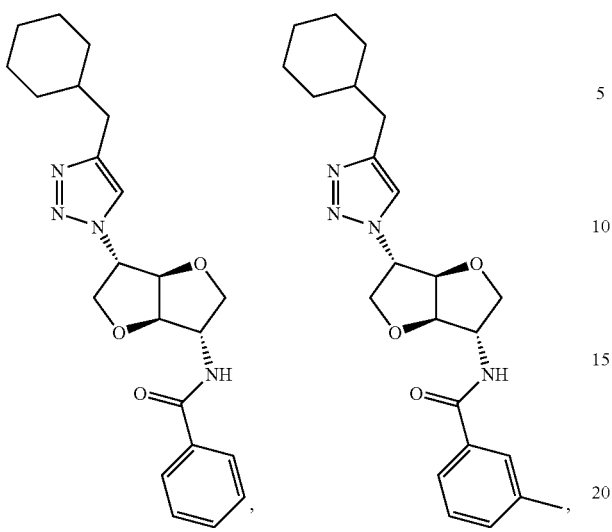
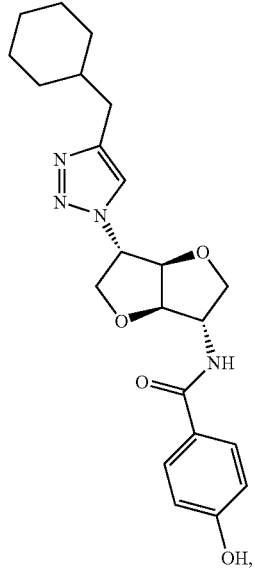
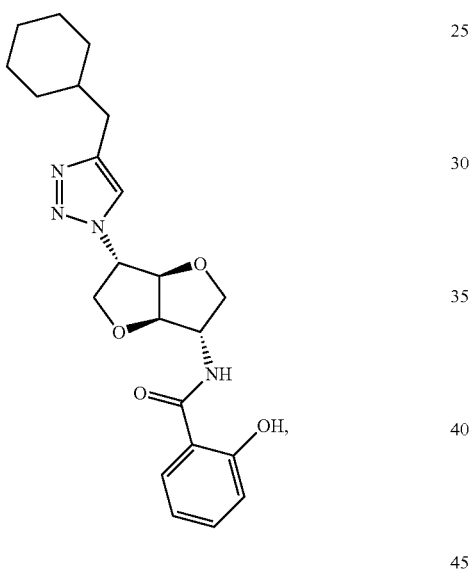
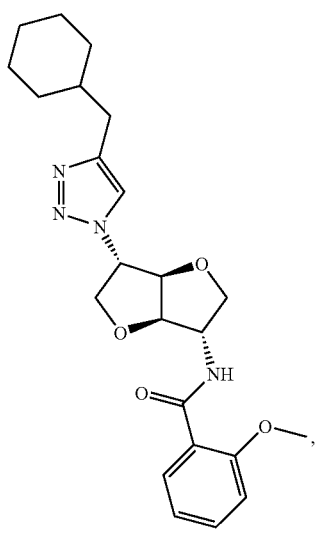
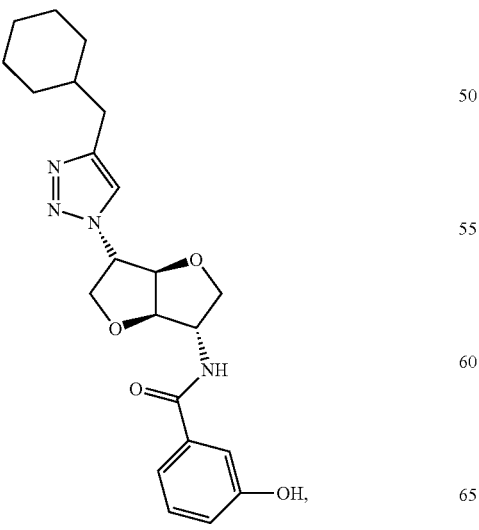
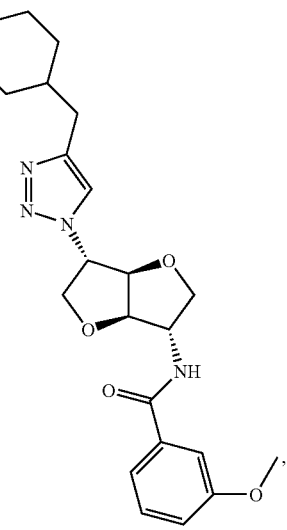

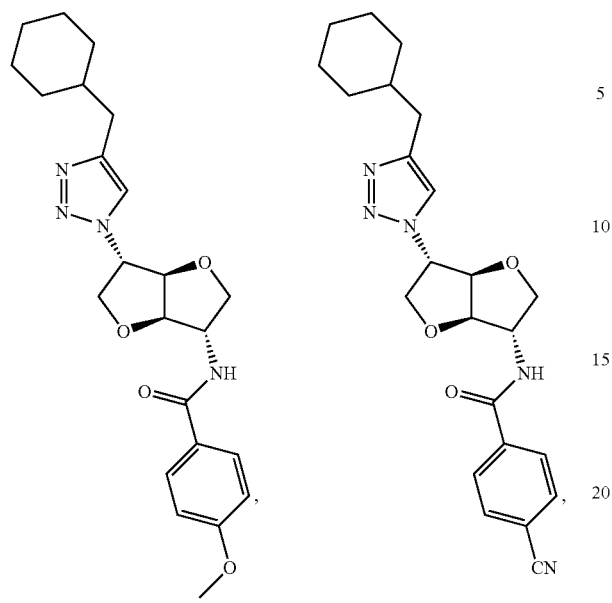
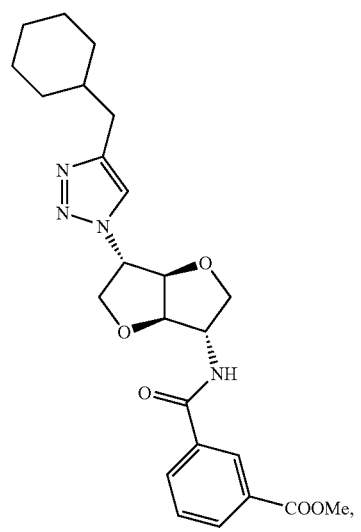
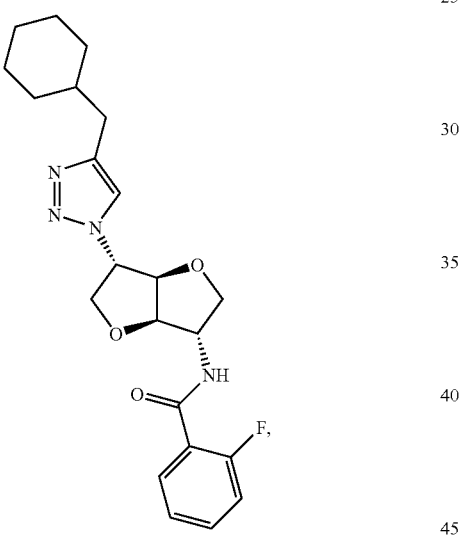
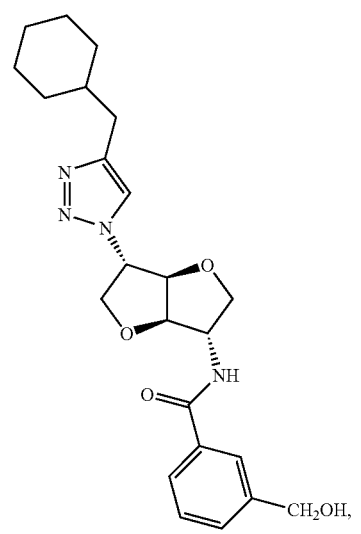
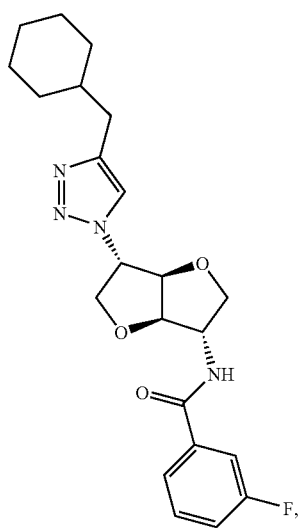

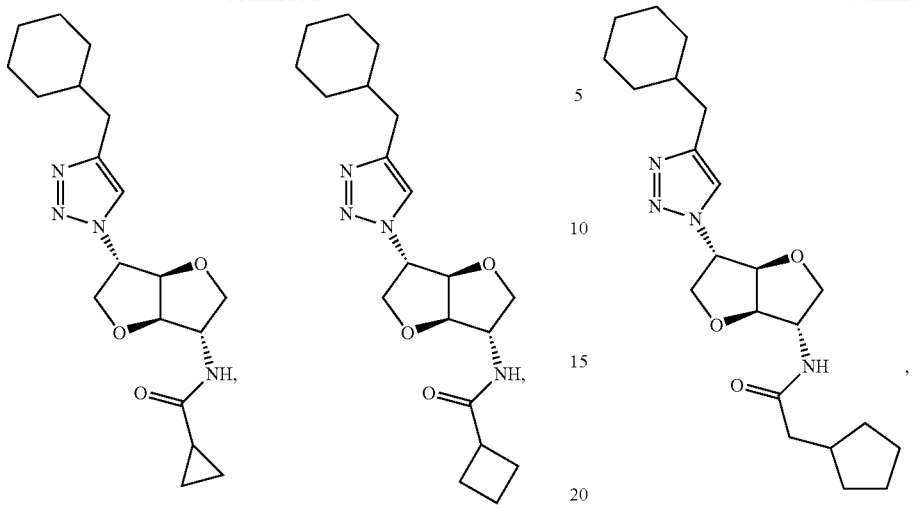
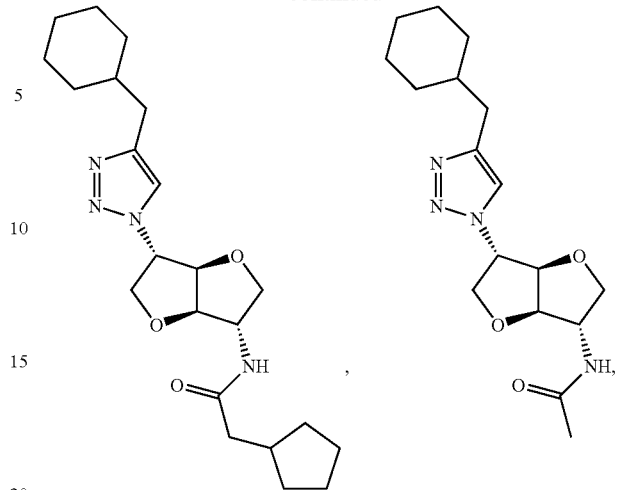
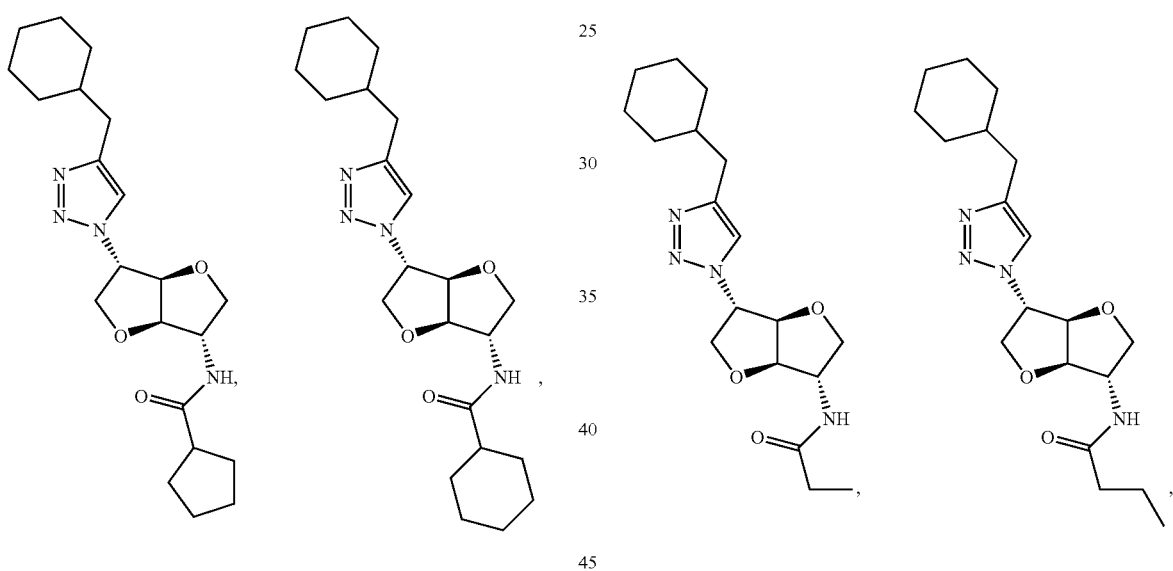
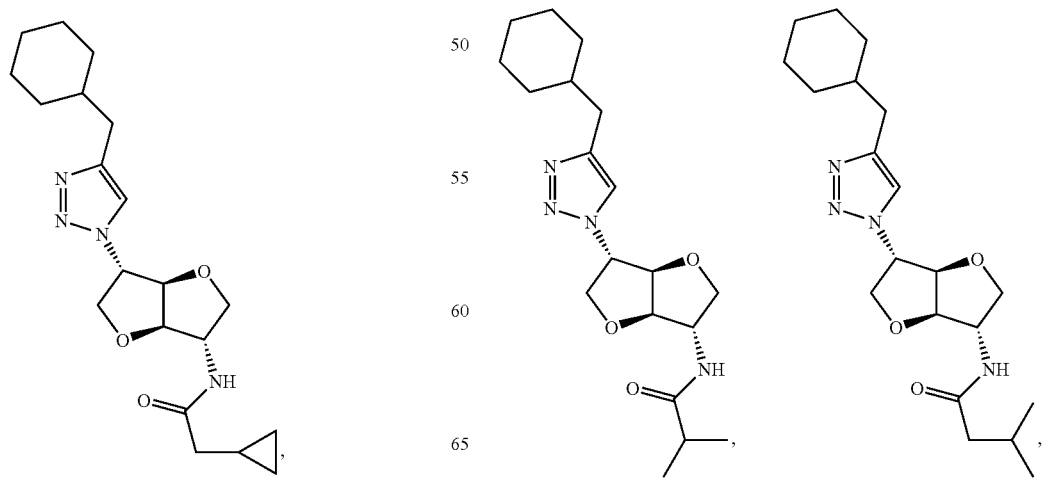

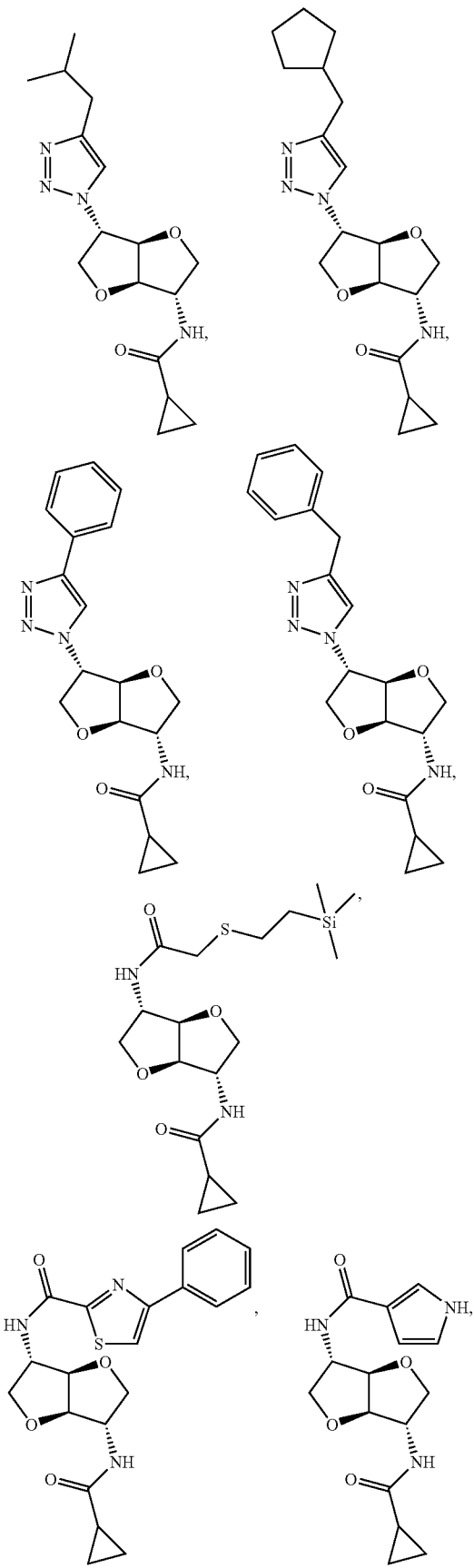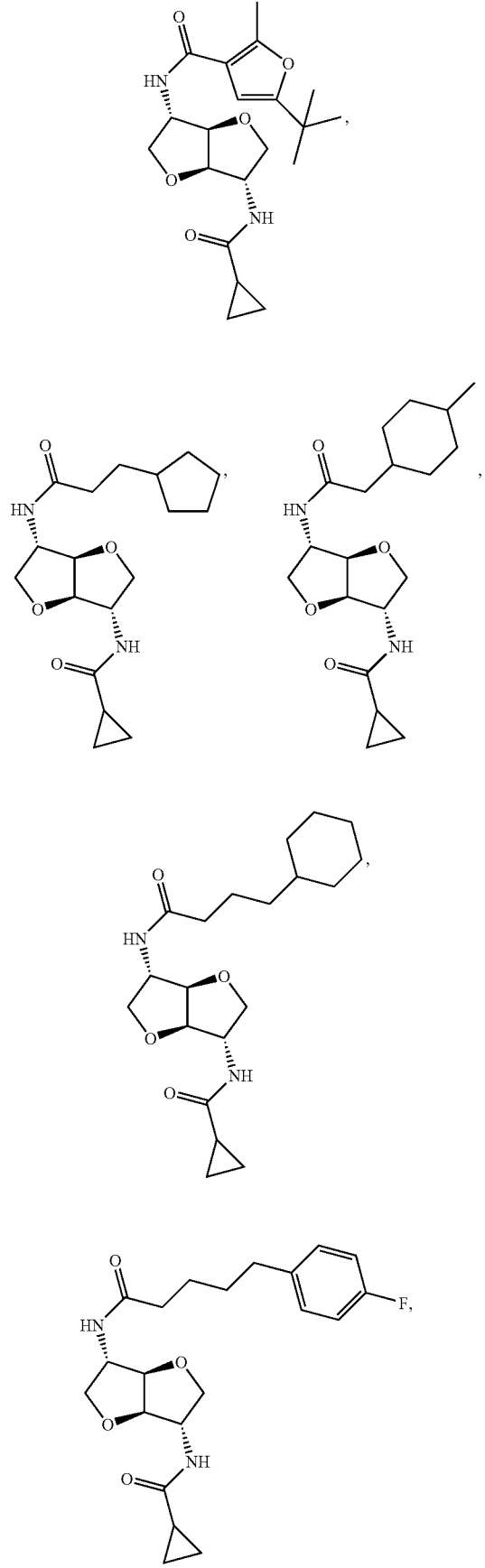

61
-continued
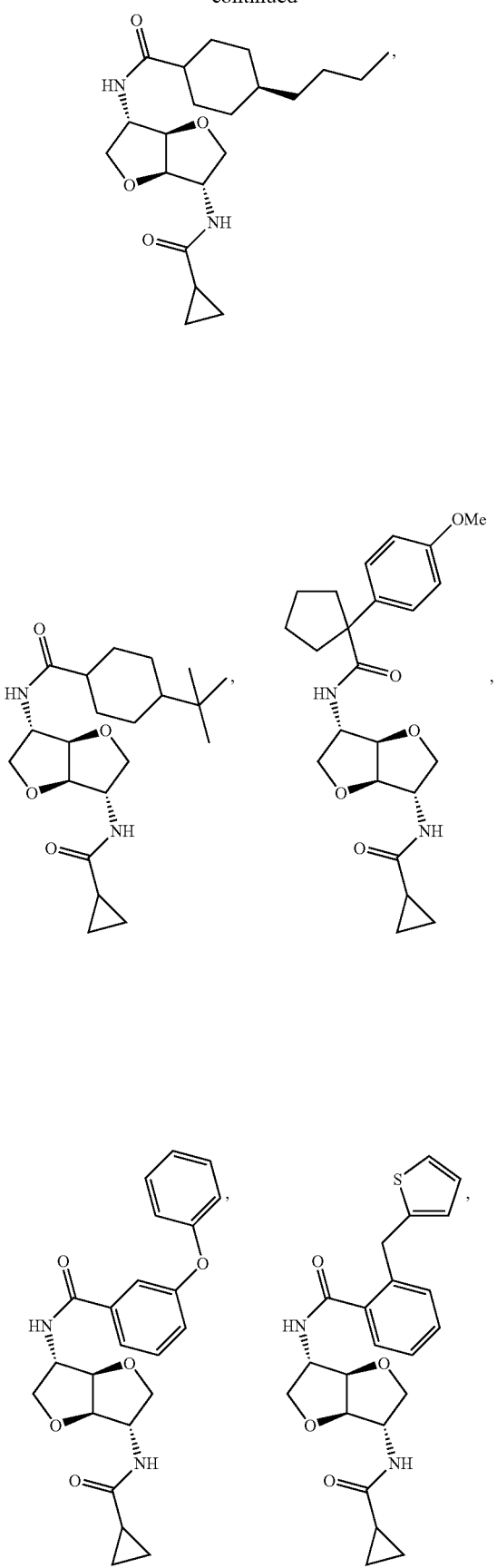
62
-continued
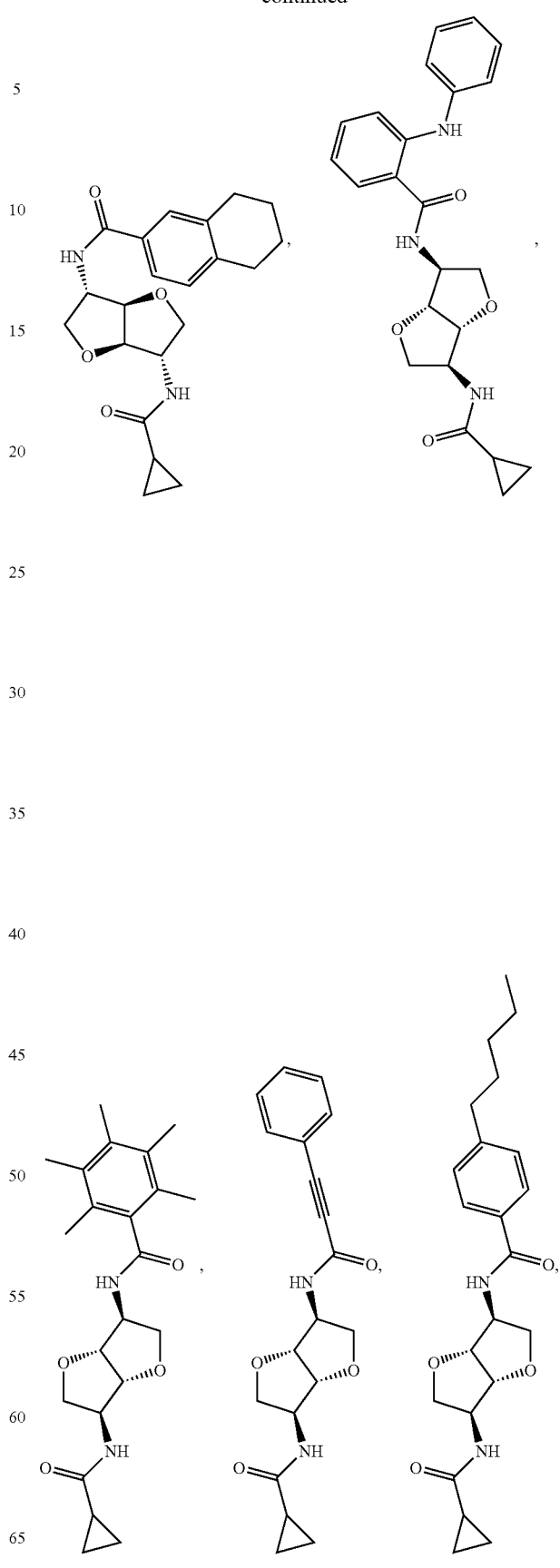

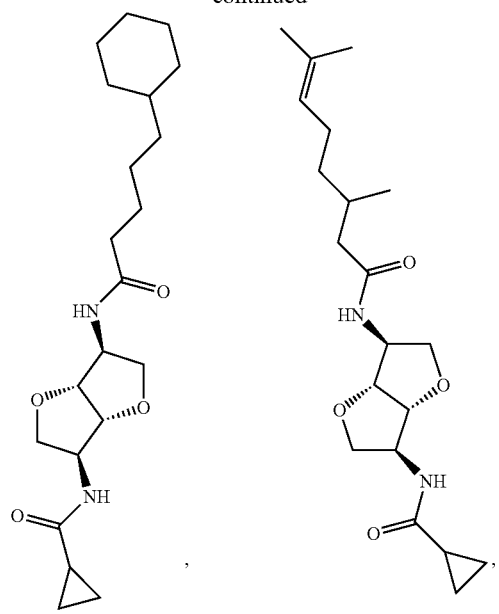
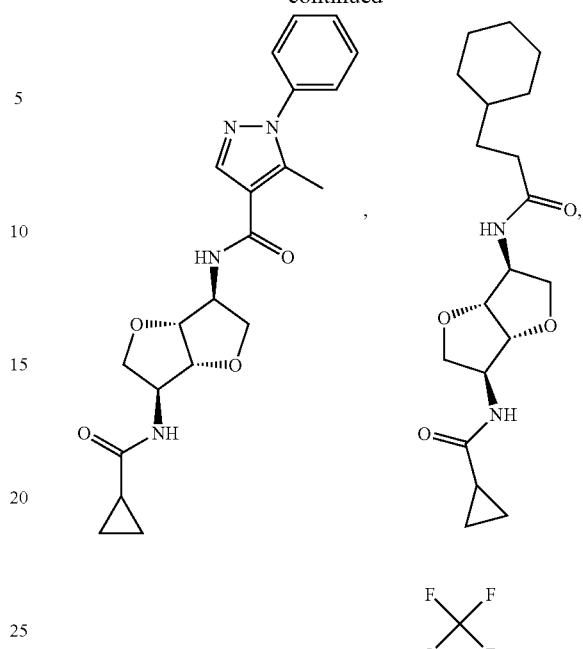

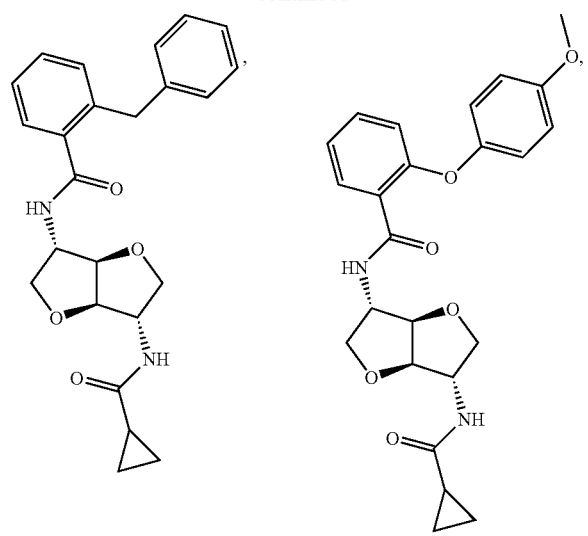
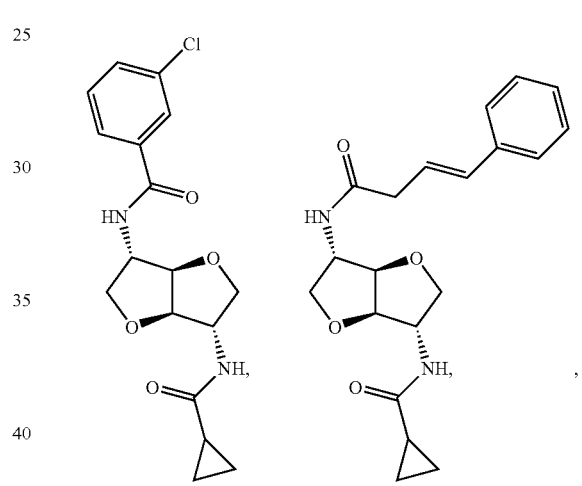
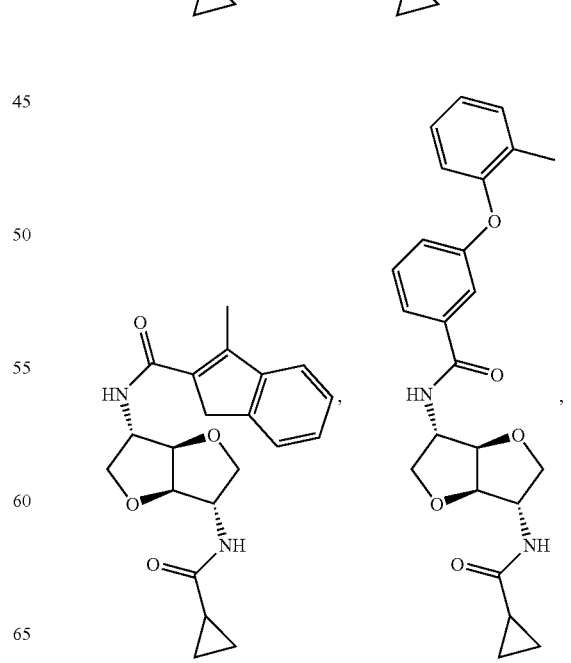

-continued

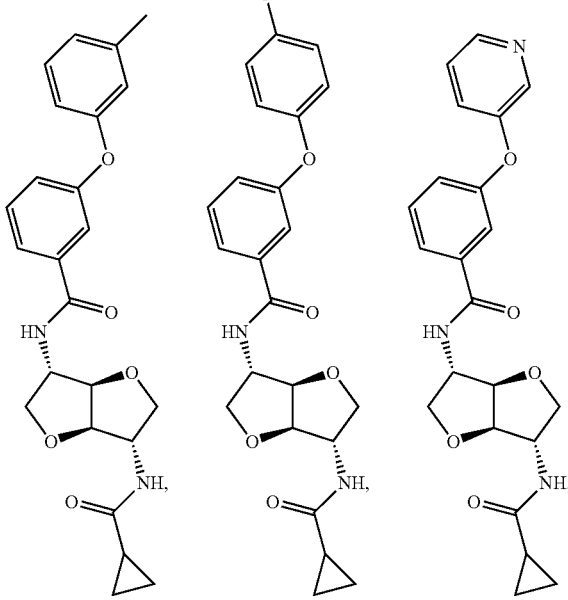

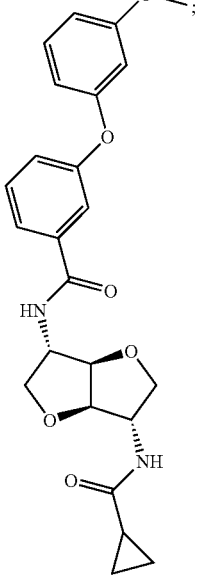

-continued

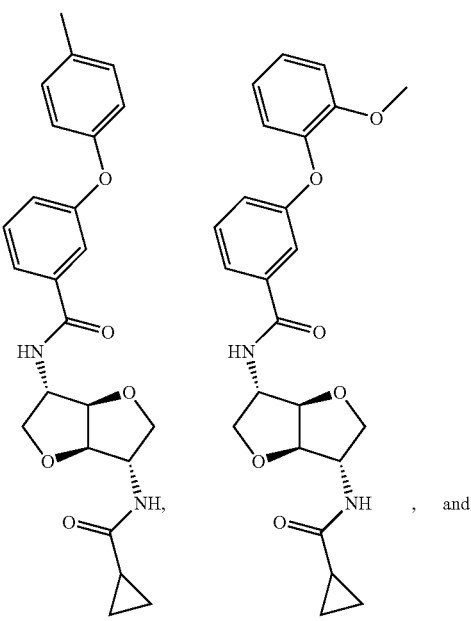

or the salt, solvate, N-oxide, ester, and/or prodrug thereof.

In one embodiment of the compound of formula (I), A is a covalent bond; Y is —OR$^1$, —S(O)R$^1$, —S(O)$_2$R$^1$, —OC(O)R$^1$, —N(R$^1$)C(O)R$^1$, —NR$^1$R$^2$, —C(O)NR$^1$R$^2$, —C(O)OR$^1$, —S(O)$_2$NR$^1$R$^2$, —N(R$^1$)S(O)$_2$R$^1$, —SR$^1$, —C(R$^1$R$^2$R$^6$), —C(S)—R$^1$, —C(=NR$^2$)—R$^1$, —N(R$^1$)—C(=N—OR$^2$)R$^6$, —C(=N—OR$^1$)R$^2$, —C(=NR$^1$)—NR$^2$R$^6$, —N(R$^1$)C(=NR$^2$)R$^6$, —N(R$^1$)C(S)R$^2$, —N(R$^1$)—C(O)—C(O)R$^2$, —N(R$^1$)C(S)N(R$^2$)—R$^6$, —C(S)—NR$^1$R$^2$, —N(R$^1$)C(=NR$^2$)OR$^6$, —C(=NR$^2$)O—NR$^2$R$^6$, —N(R$^1$)—C(=NR$^2$)—N(R$^6$)R$^7$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^2$)(R$^2$), or —P(O)R$^1$R$^2$; and R$^1$, R$^2$, R$^6$ and R$^7$ are each independently alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

In another embodiment of the compound of formula (I), wherein A is a covalent bond; Y is —N(R$^1$)C(O)R$^2$, —NR$^1$R$^2$, —N(R$^1$)S(O)$_2$R$^2$, —N(R$^1$)—C(=N—OR$^2$)R$^6$, —C(=NR$^1$)—NR$^2$R$^6$, —N(R$^1$)C(=NR$^2$)R$^6$, —N(R$^1$)C(S)R$^2$, —N(R$^1$)—C(O)—C(O)R$^2$, —N(R$^1$)C(S)N(R$^2$)—R$^6$, —N(R$^1$)C(=NR$^2$)OR$^6$, —N(R$^1$)—C(=NR$^2$)—NR$^6$R$^7$, —N(R$^1$)N(R$^2$)C(O)OR$^6$, —N(R$^1$)C(O)OR$^2$, —N(R$^1$)C(O)NR$^2$R$^6$, or —N(R$^1$)—C(O)—C(O)—NR$^2$R$^6$; X is —N(R$^3$)C(O)—, —N(R$^3$)—, —N(R$^3$)S(O)$_2$—, —N(R$^3$)—C(=N—OR$^4$)—, —N(R$^3$)C(=NR$^4$)—, —N(R$^1$)—C(=NR$^2$)—N(R$^6$)—, —N(R$^3$)C(S)—, —N(R$^3$)C(S)N(R$^4$)—, —N(R$^3$)C(O)N(R$^4$)—, —N(R$^3$)C(=NR$^4$)O—, —N(R$^3$)—C(=NR$^4$)—N(R$^5$)—, —N(R$^3$)N(R$^4$)C(O)O—, —N(R$^3$)C(O)O—, or —N(R$^3$)C(O)N(R$^4$)—; R$^1$, R$^2$, R$^3$, R$^5$, R$^6$, and R$^7$ are each independently alkyl, substituted alkyl, alkenyl, substituted alkenyl, heteroalkyl, substituted heteroalkyl, aryl, substituted aryl, heteroaryl, substituted heteroaryl, arylalkyl, substituted arylalkyl, heteroarylalkyl, substituted heteroarylalkyl, heterocyclyl, substituted heterocyclyl, carbocyclyl, or substituted carbocyclyl; and Z is alkyl, substituted alkyl, heteroalkyl, substituted heteroalkyl, aryl, substituted aryl, heteroaryl, substituted heteroaryl, arylalkyl, substituted arylalkyl, beteroarylalkyl, substituted heteroarylalkyl, carbocyclyl, or substituted carbocyclyl. Alternately, Y is —N(R¹)C(O)R², —N(R¹)—C(=N—OR²)R⁶, —N(R¹)C(S)R², —N(R)C(S)NR²R⁶, —N(R¹)C(O)NR²R⁶, —N(R¹)C(=NR²)—NR⁶R⁷, or —N(R¹)S(O)₂—R²; and X is —N(R¹)C(O)—, —N(R³)—C(=N—OR⁴)—, —N(R³)C(S)—, —N(R³)C(S)N(R⁴)—, —N(R¹)—C(=NR²)—N(R⁶)—, or —N(R³)S(O)₂—. In yet another embodiment, Z is carbocyclyl or substituted carbocyclyl; alternately Z is alkyl or substituted alkyl.

In one embodiment, the compound of formula (I) has a structural formula (Ib),

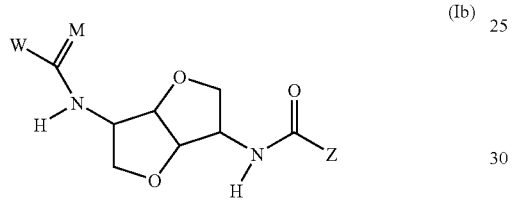
(Ib)

or a salt, solvate, N-oxide, ester, and/or prodrug thereof, wherein M is O or S; and W and Z are each independently alkyl, substituted alkyl, alkenyl, substituted alkenyl, alkynyl, substituted alkylnyl, alkoxy, alkylamine, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl. Alternately, W and Z are each independently selected from alkyl, substituted alkyl, alkenyl, substituted alkenyl, alkylamine, aryl, substituted aryl, heteroaryl, substituted heteroaryl, arylalkyl, substituted arylalkyl, heterocyclyl, substituted heterocyclyl, heteroarylalkyl, substituted heteroarylalkyl, carbocyclyl, or substituted carbocyclyl. In another alternative, Z is carbocyclyl or substituted carbocyclyl. In one embodiment, M is S; in an alternate embodiment, M is O.

In another embodiment, the compound of formula (I) has a structural formula (Ib'),

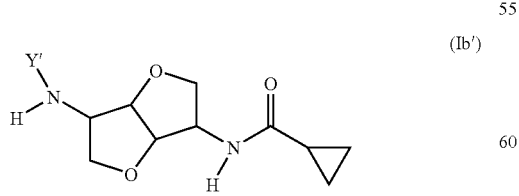
(Ib')

or a salt, solvate, N-oxide, ester, and/or prodrug thereof, wherein Y' is —C(O)R², —C(=N—OR²)R⁶, —C(S)R², —C(S)NR²R⁶, —C(O)NR²R⁶, —C(=NR²)—NR⁶R⁷, or —S(O)₂—R². In one embodiment of formula (Ib), Y' is —C(O)R², —C(S)R², —C(S)NR²R⁶, or —C(O)NR²R⁶. In some specific embodiments of formula (Ib), Y' is

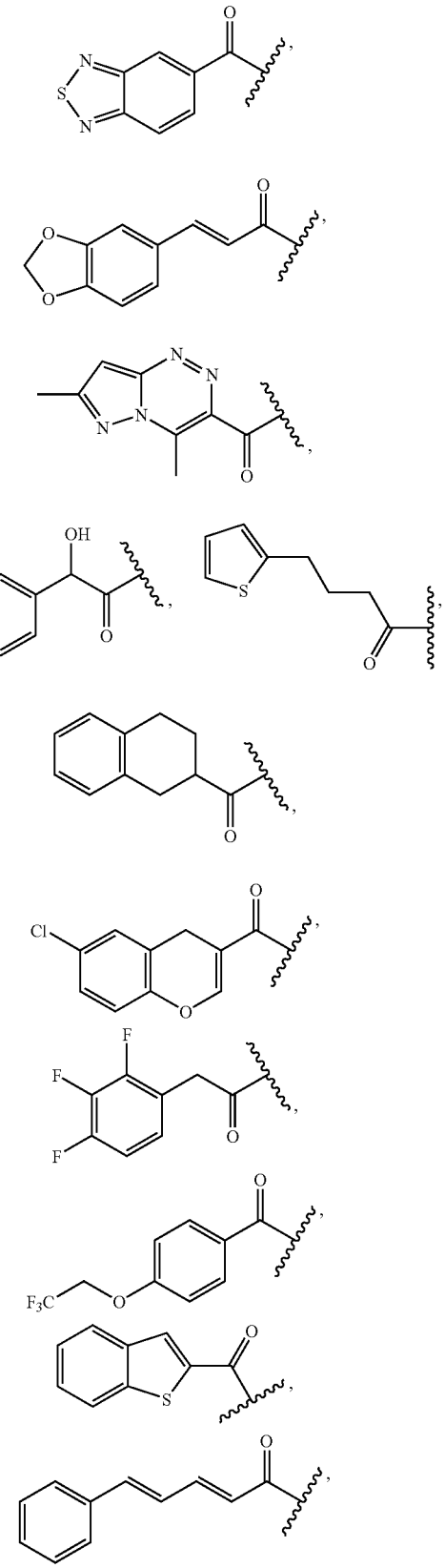

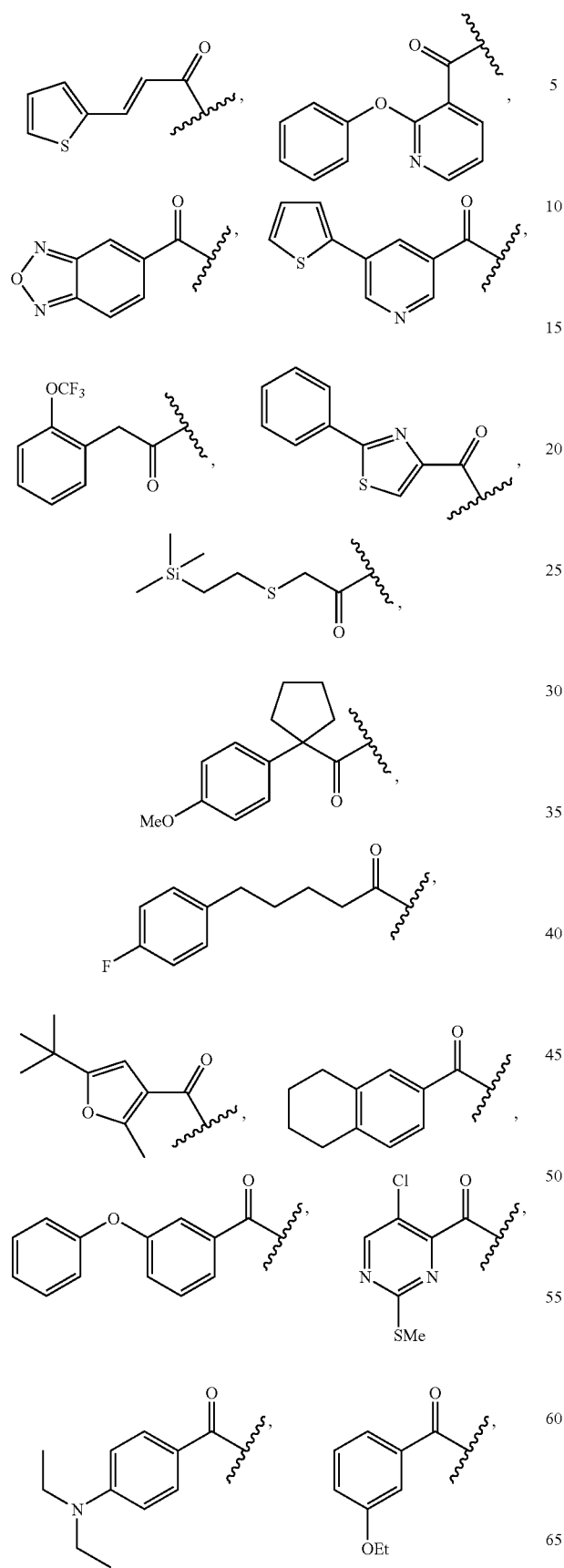
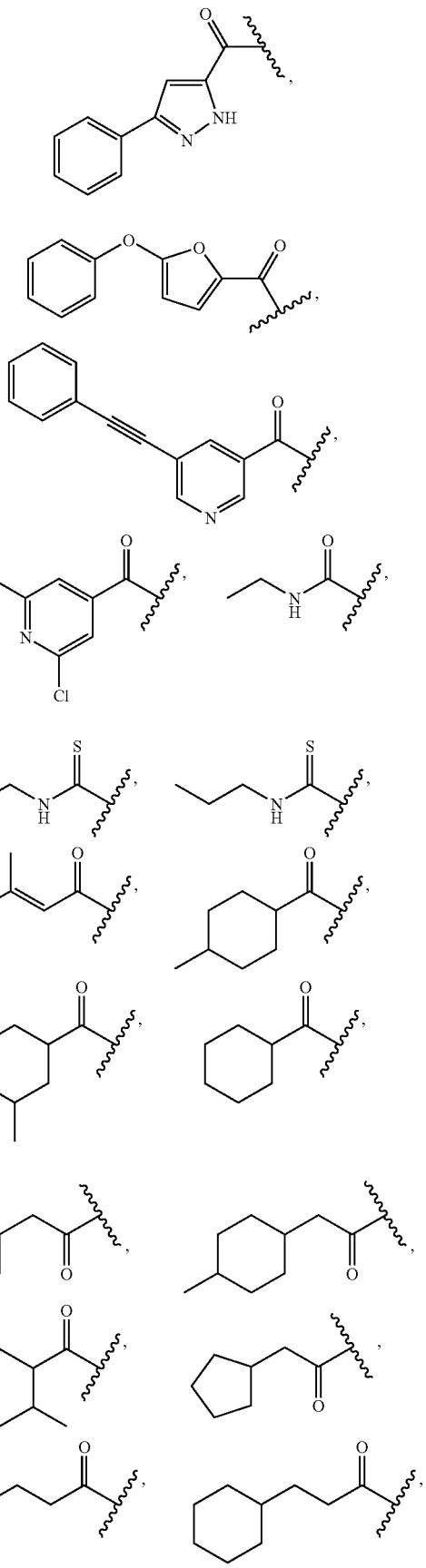

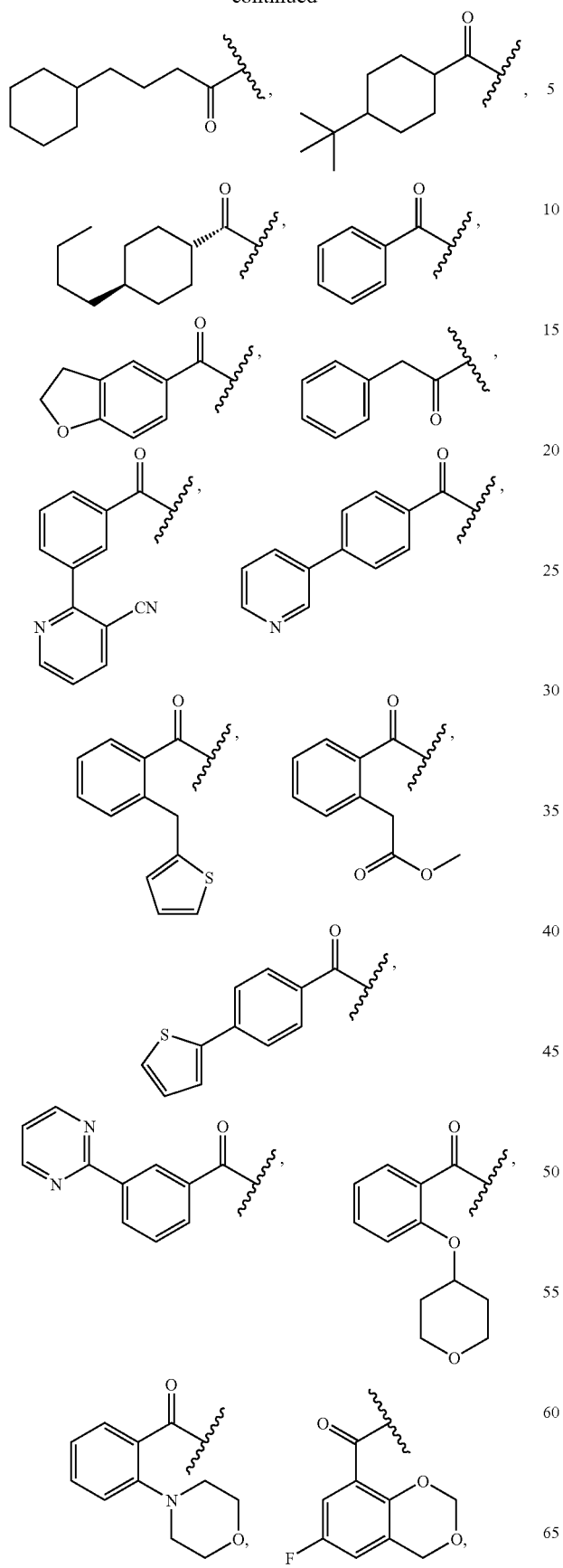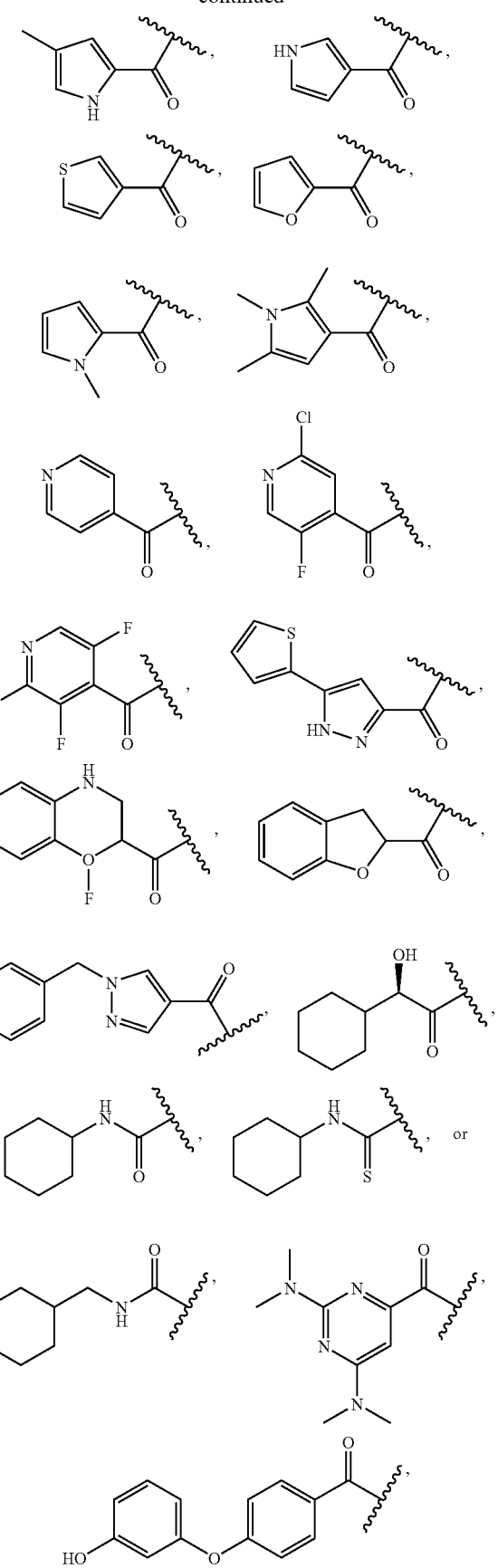

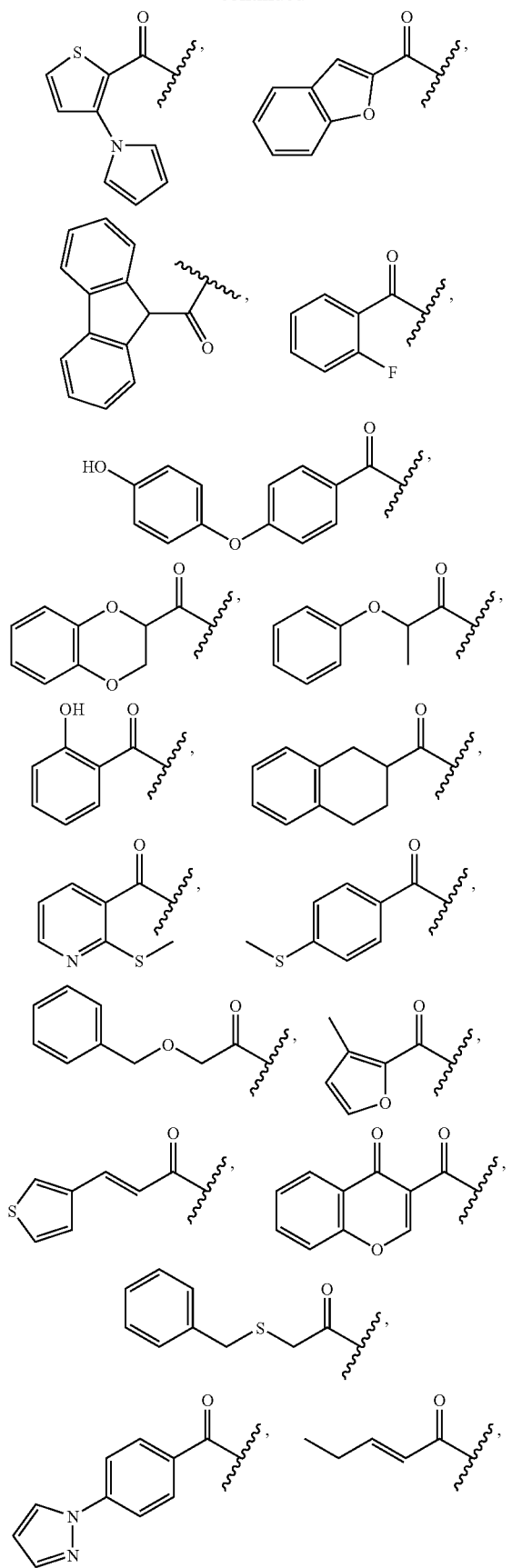
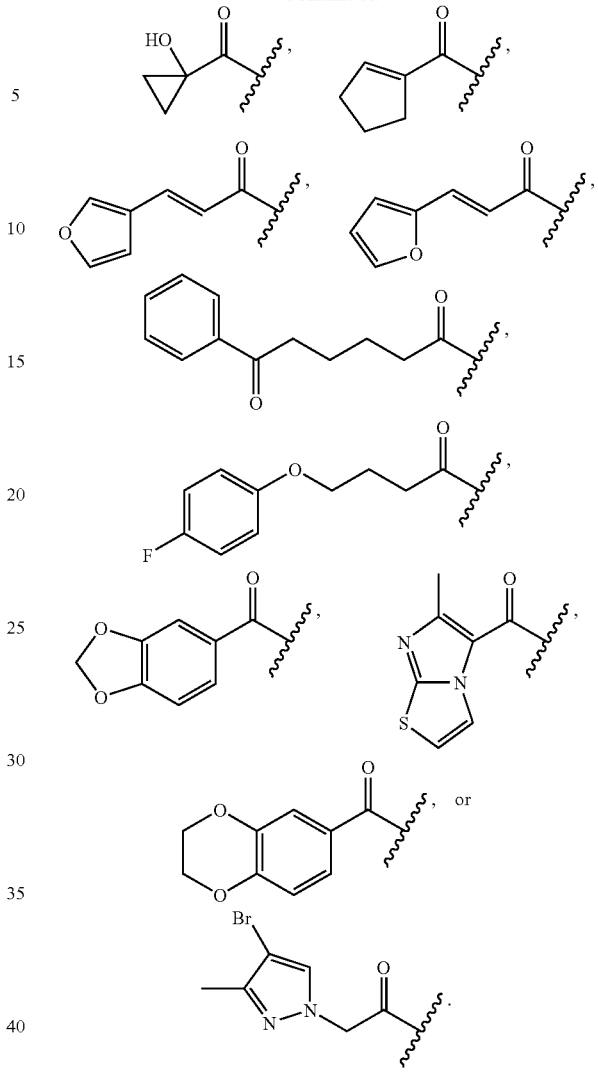

It should be understood that each of the above-listed Y' groups connects to the nitrogen atom on the isosorbide bicyclic ring of formula (Ib') through the carbon atom of the carbonyl group of Y'.

In another aspect, the present invention provides a composition comprising the compound of Formula I:

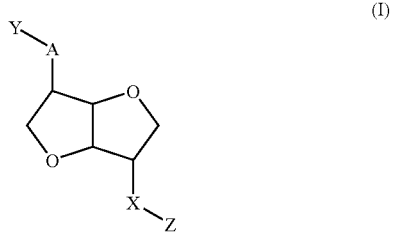

(I)

or the salt, solvate, N-oxide, ester, and/or prodrug thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$, —S(O)$_2$R$^1$, —OC(O)R$^1$, —N(R$^1$)C(O)R$^2$, —NR$^1$R$^2$, —C(O)NR$^1$R$^2$, —C(O)OR$^1$, —S(O)$^2$NR$^1$R$^2$, —COR$^1$, —N$^1$(R$^1$)S(O)$_2$R$^2$, —SR$^1$, —C(R$^1$R$^2$R$^6$), —C(S)—R$^1$, —C(=NR$^2$)—R$^1$, —N(R$^1$)—C(=N—OR$^2$)R$^6$, —N(R$^1$)C(S)NR$^2$R$^6$, —C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$, —C(=NR$^1$)O—NR$^2$R$^6$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^1$)(R$^2$), or —P(O)R$^1$R R$^2$;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —N(R$^3$)—C(=N—OR$^4$)—, —C(=N—OR$^3$)—, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —N(R$^3$)—C(O)—C(O)—NR$^4$—, —C(O)—C(O)—NR$^4$—, —P(O)(OR$^3$)—, or —P(O)R$^3$—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl; and R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

In another aspect the present invention provides a composition comprising the compound of Formula Ia, Ib, or Ib'.

In one embodiment, the composition comprises an ingestible composition. As used herein, the terms "ingestible" and "comestible" are used interexchangeably and denote a composition that can be taken by mouth. Such an ingestible composition may be taken for any purpose, such as digestion, medical treatment, chewing, cleaning, and etc. In another embodiment, the composition comprises food or beverage. In one embodiment, the present invention provides a beverage product comprising the compound of Formula I, or the salt, solvate, and/or ester thereof. In another embodiment, the present invention provides a food product comprising the compound of Formula I or the salt, solvate, and/or ester thereof.

In one embodiment, the composition is a pharmaceutical composition and the compound of Formula I is an inactive ingredient. In another embodiment, the composition is a pharmaceutical composition and the compound of Formula I is an active ingredient. In yet another embodiment, the composition is a pharmaceutical composition and further comprises a pharmaceutically acceptable vehicle. Alternately, any of the pharmaceutical compositions disclosed herein comprises a compound of Formula Ia, Ib or Ib' or the salt, solvate, N-oxide, ester and/or prodrug thereof.

In one aspect, the present invention provides a method for modulating the savory taste of a composition comprising combining the composition with at least one compound of Formula (I):

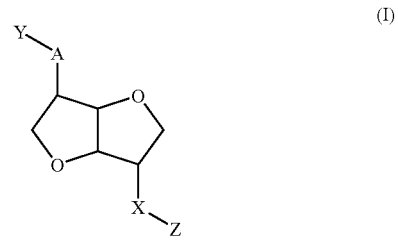

or the salt, solvate, N-oxide, ester, and/or prodrug thereof, wherein:

A is aryl, heteroaryl, or a covalent bond;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$, —S(O)$_2$R$^1$, —OC(O)R$^1$, —N(R$^1$)C(O)R$^2$, —NR$^1$R$^2$, —C(O)NR$^1$R$^2$, C(O)OR$^1$, —S(O)$_2$NR$^1$R$^2$, —COR$^1$, —N(R$^1$)S(O)$_2$R$^2$, —SR$^1$, —C(R$^1$R$^2$R$^6$), —C(S)—R$^1$, —C(=NR$^2$)—R$^1$, —N(R$^1$)—C(=N—OR$^2$)R$^6$, —N(R$^1$)C(S)NR$^2$R$^6$, —C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$, —C(=NR$^1$)O—NR$^2$R$^6$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^1$)(R$^2$), or —P(O)R$^1$R$^2$;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —N(R$^3$)—C(=N—OR$^4$)—, —C(=N—OR$^3$)—, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —N(R$^3$)—C(O)—C(O)—NR$^4$—, —C(O)—C(O)—NR$^4$—, —P(O)(OR$^3$)—, or —P(O)R$^3$—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl; and R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

In another aspect, the present invention provides a method for modulating the savory taste of a composition comprising combining the composition with at least one compound of Formula (Ia), (Ib), or (Ib').

Using the Compounds of Formula (I) to Prepare Compositions

The compounds of Formula (I) and its various compound sub-genuses and species, as described above are intended to be savory flavorant compounds or flavor modifiers for comestible products. As is apparent from the teachings and Examples herein, many compounds of Formula (I) are agonists of an hT1R1/hT1R3 "savory" receptor, at least at concentrations of about 100 µM or less. Accordingly many of the compounds of Formula (I) have a significant savory flavor independent of the presence or absence of MSG, and therefore can have utility as independent savory flavorants or flavor enhancers.

Nevertheless, it is preferable to use as little of such artificial flavorants as possible, so as to minimize both cost and undesirable health side effects of administration of the compounds of Formula (I) at high concentration levels. Accordingly, it is desirable to test the compounds of Formula (I) for their effectiveness as taste receptor agonists at lower concentration levels, so as to identify the best and most effective compounds of Formula (I). As was disclosed in WO 03/001876, and U.S. Patent Publication US 2003/0232407 A1, hereby incorporated herein by reference and as described hereinbelow, laboratory procedures now exist for measuring the agonist activities of compounds for an hT1R1/hT1R3 "savory" receptor. Such measurement methods typically measure an "$EC_{50}$", i.e. the concentration at which the compound causes 50% activation of the relevant receptor.

Preferably, the compounds of Formula (I) that are savory flavor modifiers have an $EC_{50}$ for the hT1R1/hT1R3 receptor of less than about 10 µM. More preferably, such compounds have an $EC_{50}$ for the hT1R1/hT1R3 receptor of less than about 5 µM, 3 µM, 2 µM, 1 µM, or 0.5 µM.

In some embodiments, the compounds of Formula (I) are savory flavor modulators or enhancers of the agonist activity of monosodium glutamate for an hT1R1/hT1R3 receptor. Hereinbelow is described an assay procedure for so-called $EC_{50}$ ratios, i.e. for dissolving a compound of Formula (I) in water containing MSG, and measuring the degree to which the compound lowers the amount of MSG required to activate 50% of the available hT1R1/hT1R3 receptors. Preferably, the compounds of Formula (I), when dissolved in an aqueous solution comprising about 1 µM of the compound will decrease the observed $EC_{50}$ of monosodium glutamate for an hT1R1/hT1R3 receptor expressed in an HEK293-Gα15 cell line by at least 50%, i.e. the compound will have an $EC_{50}$ ratio of at least 2.0, or preferably 3.0, 5.0, or 7.0.

The above identified assays are useful in identifying the most potent of the compounds of Formula (I) for savory taste modifier or enhancer properties, and the results of such assays are believed to correlate well with actual savory taste perception in animals and humans, but ultimately the results of the assays can be confirmed, at least for the most potent of the compounds of Formula (I), by human taste testing. Such human taste testing experiments can be well quantified and controlled by tasting the candidate compounds in aqueous solutions, as compared to control aqueous solution, or alternatively by tasting the compounds of the inventions in actual food compositions.

Accordingly, in order to identify the more potent of the savory taste modifiers or agents, a water solution comprising a savory flavor modifying amount of any particular compound of Formula (I) or one of its subgenuses should have a savory taste as judged by the majority of a panel of at least eight human taste testers.

Correspondingly, in order to identify the more potent of the savory taste enhancers, a water solution, comprising a savory flavor modifying amount of a compound of Formula (I) and 12 mM monosodium glutamate, would have an increased savory taste as compared to a control water solution comprising 12 mM monosodium glutamate, as determined by the majority of a panel of at least eight human taste testers. Preferably, in order to identify the more potent of the savory taste enhancers, a water solution comprising a savory flavor modifying amount (preferably about 30, 10, 5, or 2 ppm) of the compound of Formula (I) and 12 mM monosodium glutamate will have an increased savory taste as compared to a control water solution comprising 12 mM monosodium glutamate and 100 µM inosine monophosphate, as determined by the majority of a panel of at least eight human taste testers.

Using the Compounds of Formula (I) to Prepare Comestible Compositions

Flavors, flavor modifiers, flavoring agents, flavor enhancers, savory ("umami") flavoring agents and/or flavor enhancers, prepared from the compounds of Formula I and its various subgenera and species compounds herein, and their comestibly acceptable salts, and compositions thereof, have application in foods, beverages and other comestible compositions wherein savory compounds, especially MSG, IMP, or GMP are conventionally utilized. These compositions include compositions for human and animal consumption. This includes food or drinks (liquids) for consumption by agricultural animals, pets and zoo animals.

As used herein, the terms "ingestible composition" and "comestible composition" are used exchangeably and refer to any composition that can be taken by mouth. The ingestible or comestible composition may be taken by the mouth for any purpose including digestion, chewing, cleaning, etc. The ingestible composition includes both "food/beverage" and "non-edible products". For example, the ingestible composition includes food/beverage compositions or products and medicinal compositions or products. "Food" herein means any edible product intended for consumption by humans or animals, including solids, semi-solids, or liquids (e.g., beverages). The term "food" and the term "food and beverage" are herein used interchangeably.

Those of ordinary skill in the art of preparing and selling comestible compositions (i.e. edible foods or beverages, or precursors or flavor modifiers thereof) are well aware of a large variety of classes, subclasses and species of the comestible compositions, and utilize well-known and recognized terms of art to refer to those comestible compositions while endeavoring to prepare and sell various of those comestible compositions. Such a list of terms of art is enumerated below, and it is specifically contemplated hereby that the various subgenuses and species of the compounds of Formula (I) could be used to modify or enhance the savory flavors of the following list comestible compositions, either singly or in all reasonable combinations or mixtures thereof: one or more confectioneries, chocolate confectionery, tablets, countlines, bagged selflines/softlines, boxed assortments, standard boxed assortments, twist wrapped miniatures, seasonal chocolate, chocolate with toys, alfajores, other-chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarised gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, breakfast cereals, rte cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurised milk, full fat fresh/pasteurised milk, semi skimmed fresh/pasteurised milk, long-life/uht milk, fill fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavoured fromage frais and quark, savoury fromage frais and quark, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and Seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, seasonings and seasoning blends, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

Preferably, the compounds of Formula (I) can be used to modify or enhance the savory flavor of one or more of the following sub-genuses of comestible compositions: confectioneries, bakery products, ice creams, dairy products, savory snacks, snack bars, meal replacement products, ready meals, soups, pastas, noodles, canned foods, frozen foods, dried foods, chilled foods, oils and fats, baby foods, or spreads, or a mixture thereof.

In general an ingestible composition will be produced that contains a sufficient amount of at least one compound within the scope of Formula (I) or its various subgenuses described hereinabove to produce a composition having the desired flavor or taste characteristics such as "savory" taste characteristics.

Typically at least a savory flavor modulating amount, of one or more of the compounds of Formula (I) will be added to the comestible product, so that the savory flavor modified comestible product has an increased savory taste as compared to the comestible product prepared without the compound of Formula (I), as judged by human beings or animals in general, or in the case of formulations testing, as judged by a majority of a panel of at least eight human taste testers, via procedures described elsewhere herein.

The concentration of savory flavoring agent needed to modulate or improve the flavor of the comestible product or composition will of course vary dependent on many variables, including the specific type of ingestible composition, what savory compounds are already present and the concentrations thereof, the amount of MSG already present, and the enhancer effect of the particular compound on such savory compounds. As noted, a significant application of the compounds of Formula (I) is for modulating (inducing, enhancing or inhibiting) the savory tastes or other taste properties of other natural or synthetic savory tastants, especially MSG. A broad range of concentrations of the compounds of Formula (I) can be employed to provide such savory taste enhancement, i.e. from about 0.001 ppm to 100 ppm, or narrower alternative ranges from about 0.1 ppm to about 10 ppm, from about 0.01 ppm to about 30 ppm, from about 0.05 ppm to about 15 ppm, from about 0.1 ppm to about 5 ppm, or from about 0.1 ppm to about 3 ppm.

A variety of classes, subclasses and species of foods are known. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh, instant, and combined coffee; tea, such as black, green, white, oolong, and flavored tea; and other hot drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal include products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

According to the present invention, "non-edible products" include supplements, nutraceuticals, functional food products (e.g., any fresh or processed food claimed to have a health-promoting and/or disease-preventing properties beyond the basic nutritional function of supplying nutrients), pharmaceutical and over the counter products, oral care products such as dentifrices and mouthwashes, cosmetic products such as sweetened lip balms and other personal care products that use sucralose and or other sweeteners.

The term "edible ingredient" herein means any edible component or mixture of components of food or food products, for example the edible ingredients which would typically be found in a recipe for human or animal foods. Edible ingredients include natural and synthetic food components.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners and dental floss.

In one embodiment of the present invention, the present compounds, i.e., compounds of Formula (I) including any subgenus and specific embodiments thereof, can be formulated to make a high-protein composition. By "high-protein composition", it is meant a composition wherein the percentage of proteins or amino acids is higher than that in natural food or beverage. Examples of the high-protein composition includes, but are not limited to, protein shakes, protein powder, protein-enhanced drinks, and other high protein diet. Examples of the proteins suitable for the high-protein composition include, but are not limited to, vegetable or gluten based proteins, such as wheat, soy, rice, and corn; dairy based proteins such as whey, milk, and caseins; animal based proteins such as poultry, beef, and gelatin; and other protein hydrolysates.

In another embodiment, the present invention provides a flavoring composition comprising a compound of Formula (I) and a carrier. The term "carrier" refers to a diluent, adjuvant, excipient or vehicle with which the present compound is formulated. Typically, the flavoring composition has a flavor that is stronger or more concentrated than the flavor in a composition directly taken by the mouth. Such a flavoring composition can be added to another composition as a flavor source or to increase the flavor of another composition. That is, the flavoring composition can be used as a seasoning ingredient in another composition. The concentration of the present compound in the flavoring composition is typically higher than that in a ready-to-serve composition. The flavoring composition can be a liquid, semi-liquid, gel, foam, semi-solid, or solid. The solid form may be tablet, powder, granule, cube, capsule, and the like. In one specific embodiment, the flavoring composition also contains MSG or other umami tastants.

Other examples of foods and beverages wherein compounds according to the invention may be incorporated included by way of example carbonated and non-carbonated beverages, e.g., sodas, fruit or vegetable juices, alcoholic and non-alcoholic beverages, confectionary products, e.g., cakes, cookies, pies, candies, chewing gums, gelatins, ice creams, sorbets, puddings, jams, jellies, salad dressings, and other condiments, cereal, and other breakfast foods, canned fruits and fruit sauces and the like.

Additionally, the subject compounds can be used in flavor preparations to be added to foods and beverages. In preferred instances the composition will comprise another flavor or taste modifier such as a savory tastant.

Accordingly, in some embodiments, the inventions relate to methods for modulating the savory taste of a comestible product comprising: a) providing at least one comestible product, or a precursor thereof, and b) combining the comestible product or precursor thereof with at least a savory flavor modulating amount of at least one compound of Formula (I) or any of its subgenuses, or a comestibly acceptable salt thereof, so as to form a modified comestible product.

The invention also relates to the modified comestible products produced by such processes, and similar processes for producing comestible products well known to those of ordinary skill in the art, especially if such compositions comprise MSG, and the compound is employed as a savory taste enhancer for the MSG also present in the composition.

The compounds of Formula (I) and its various subgenuses can be combined with or applied to the comestible or medicinal products or precursor thereof in any of innumerable ways known to cooks the world over, or producers of comestible or medicinal products. For example, the compounds of Formula (I) could be dissolved in or dispersed in or one one of many known comestibly acceptable liquids, solids, or other carriers, such as water at neutral, acidic, or basic pH, fruit or vegetable juices, vinegar, marinades, beer, wine, natural water/fat emulsions such as milk or condensed milk, edible oils and shortenings, fatty acids, certain low molecular weight oligomers of propylene glycol, glyceryl esters of fatty acids, and dispersions or emulsions of such hydrophobic substances in aqueous media, salts such as sodium chloride, vegetable flours, solvents such as ethanol, solid edible diluents such as vegetable powders or flours, and the like, and then combined with precursors of the comestible or medicinal products, or applied directly to the comestible or medicinal products.

Example Procedures for Making the Compounds of Formula (I)

Scheme 1: Preparation of (3S,3aR,6S,6aR)-3,6-diazidohexahydrofuro[3,2-b]furan.

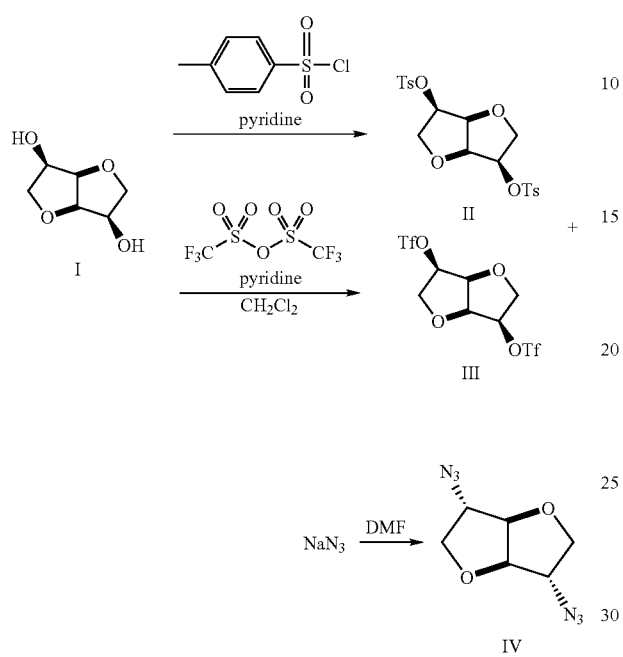

As shown in Scheme 1, (3R,3αR,6R,6αR)-hexahydrofuro[3,2-b]furan-3,6-diol (1) can be converted to the bisazide (IV) through formation of the bistosylate (II) or bistriflate (III). Displacement with sodium azide provides the bisazide (IV) with the desired stereochemistry.

Scheme 2:
Conversion of (3S,3aR,6S,6aR)-3,6-diazidohexahydrofuro[3,2-b]furan to amide-substituted final compounds.

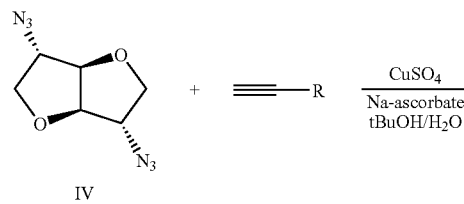

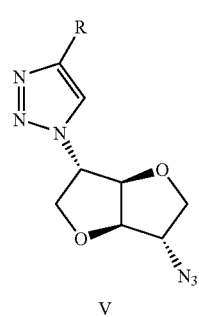

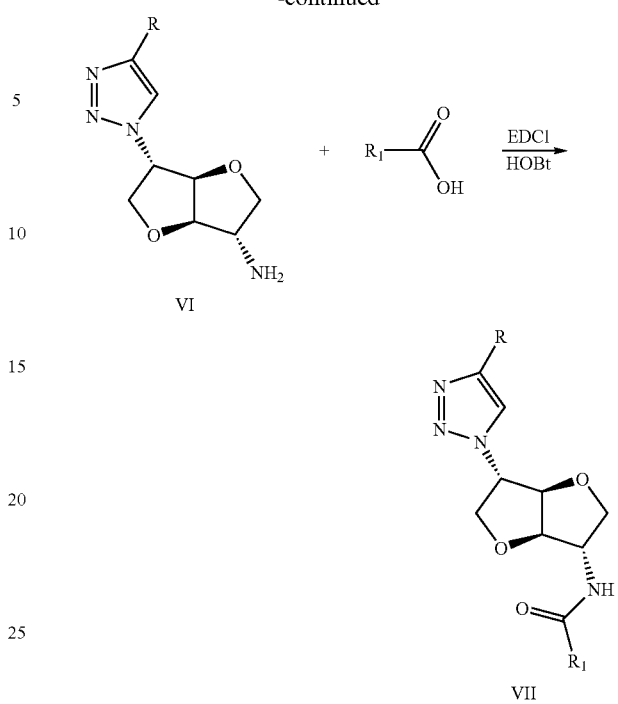

The bisazide (IV) can be converted into the mono-substituted triazole (V) using traditional "click" chemistry in the presence of copper (II) sulfate and sodium ascorbate. Catalytic hydrogenation, followed by amide coupling provides the desired product (VII) (Nören-Müller, A.; Reis-Corrêa, I. Jr.; Prinz, H.; Rosenbaum, C.; Saxena, K.; Schwalbe, H. J.; Vestweber, D.; Cagna, G.; Schunk, S.; Schwarz, O.; Schiewe, H.; Waldmann, H. *Proc. Nat. Acad. Sci.* 2006, 103, 10606-10611).

Scheme 3: Alternative method for synthesis triazole analogs

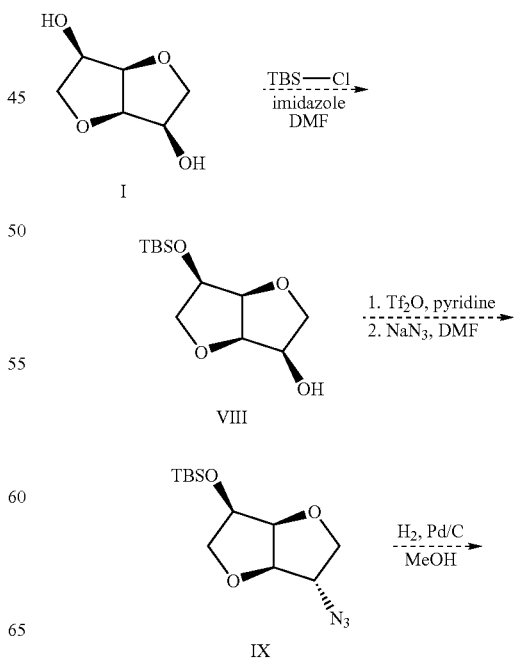

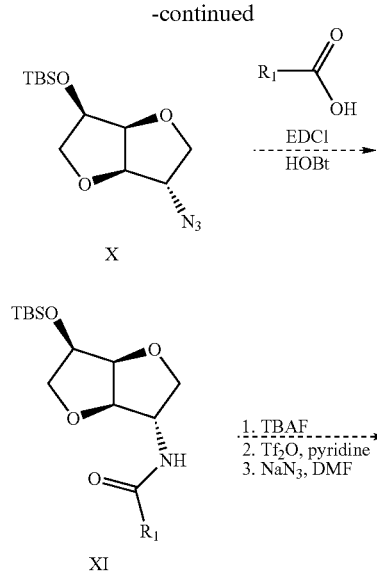

formation, and subsequent formation of the azide XII through the triflate intermediate provides a handle for making a variety of substituted triazoles VII (Vogler, M.; Koert, U.; Dorsch, D.; Gleitz, J.; Raddatz, P. *Synlett* 2003, 1683-1687).

Scheme 4: Preparation of urea, thiourea and sulfonamide-containing compounds.

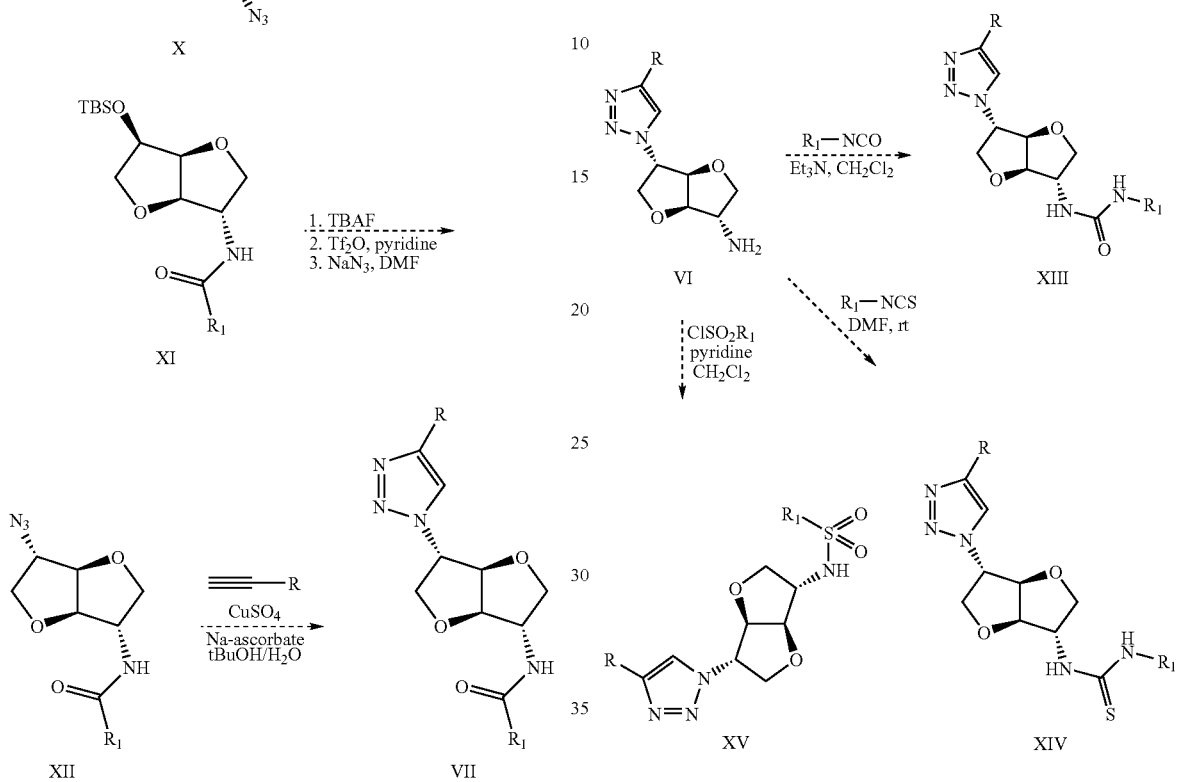

Monoprotection of one of the alcohols of I leads to mono-t-butyldimethylsilyl protected VIII. Formation of the triflate, followed by displacement with NaN$_3$ results in intermediate IX, which can be hydrogenated to yield the free amine. Amide From amine VI, urea analogs XIII can be prepared by reaction with an isocyanate, and analogously, thioureas XIV may be prepared by reaction with an isothiocyanate. The sulfonamide analogs XV are prepared by reaction of amine VI with R$_1$-substituted sulfonyl chlorides.

Scheme 5: Synthesis of oxalamide and carbamate analogs.

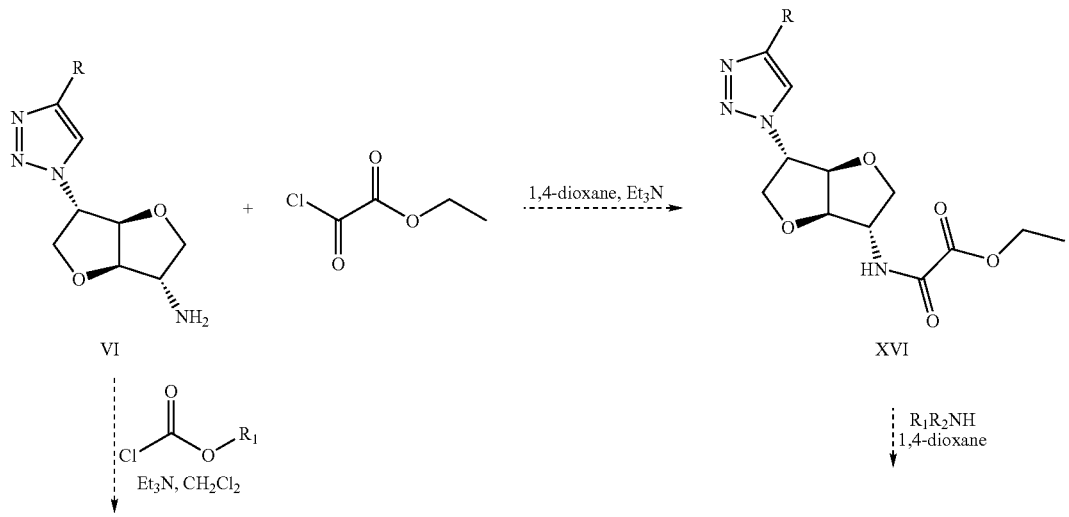

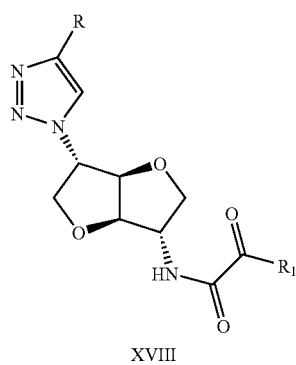

XVIII

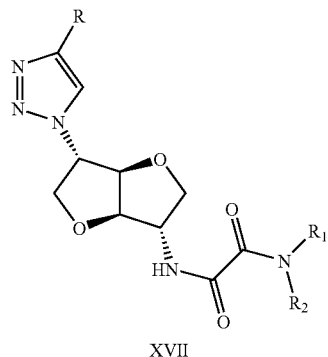

XVII

Amine VI can be reacted with ethyl 2-chloro-2-oxoacetate in the presence of Et$_3$N to provide the ethyl oxoacetate XVI, which can then go on to react with a primary or secondary amine to yield the desired oxalamides XVII. In addition, amine VI can be converted to the carbamate by reaction with R$_1$-substituted chloroformate in Et$_3$N and CH$_2$Cl$_2$ to provide the desired carbamates XVIII.

Scheme 6: Preparation of mono-and disubstituted amine analogs.

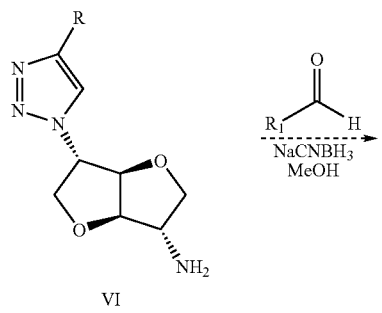

VI

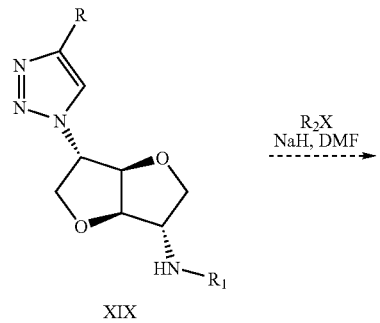

XIX

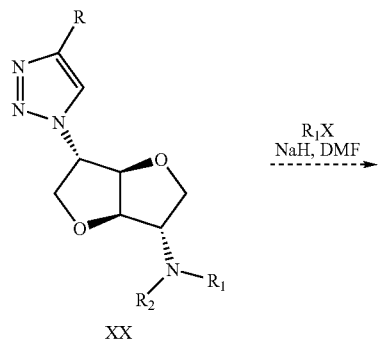

XX

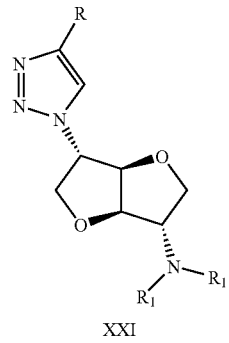

XXI

Preparation of differentially substituted diamine analogs XX can be synthesized by reaction of amine VI with an aldehyde in the presence of NaCNBH$_3$. A second amine substitution can then be accomplished by reaction with an alkyl halide in the presence of a base such as NaH. N,N-disubstituted analogs can be accomplished through reaction of amine VI with two equivalents of a halide in the presence of NaH to provide N,N-disubstituted amine XXI.

Scheme 7: Preparation of mono-amine building block.

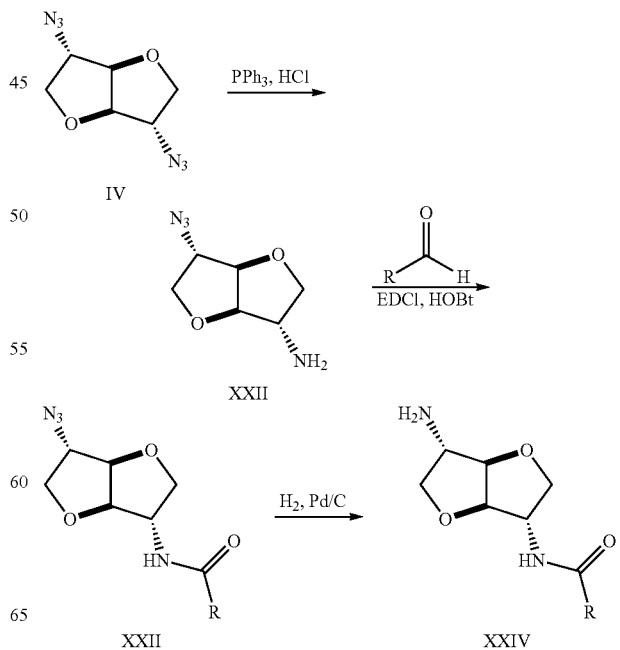

Preparation of the mono-amide amine building block XXIV can be accomplished through mono-azide reduction with triphenylphosphine and HCl (Lee, J. W.; Jun, S. I.; Kim, K. *Tetrahedron Lett.* 2001, 42, 2709-2711.), followed by amide coupling with a carboxylic acid in the presence of HOBt and EDCI. Hydrogenation of resultant azide XXIII provides amine XXIV.

Reaction of amine XXIV with a carboxylic acid in the presence of HOBt and EDCI provides unsymmetrical bisamide XXV. In addition, reaction of the amine XXIV with a sulfonyl chloride and pyridine results in formation of sulfonamide-containing compounds XXVI.

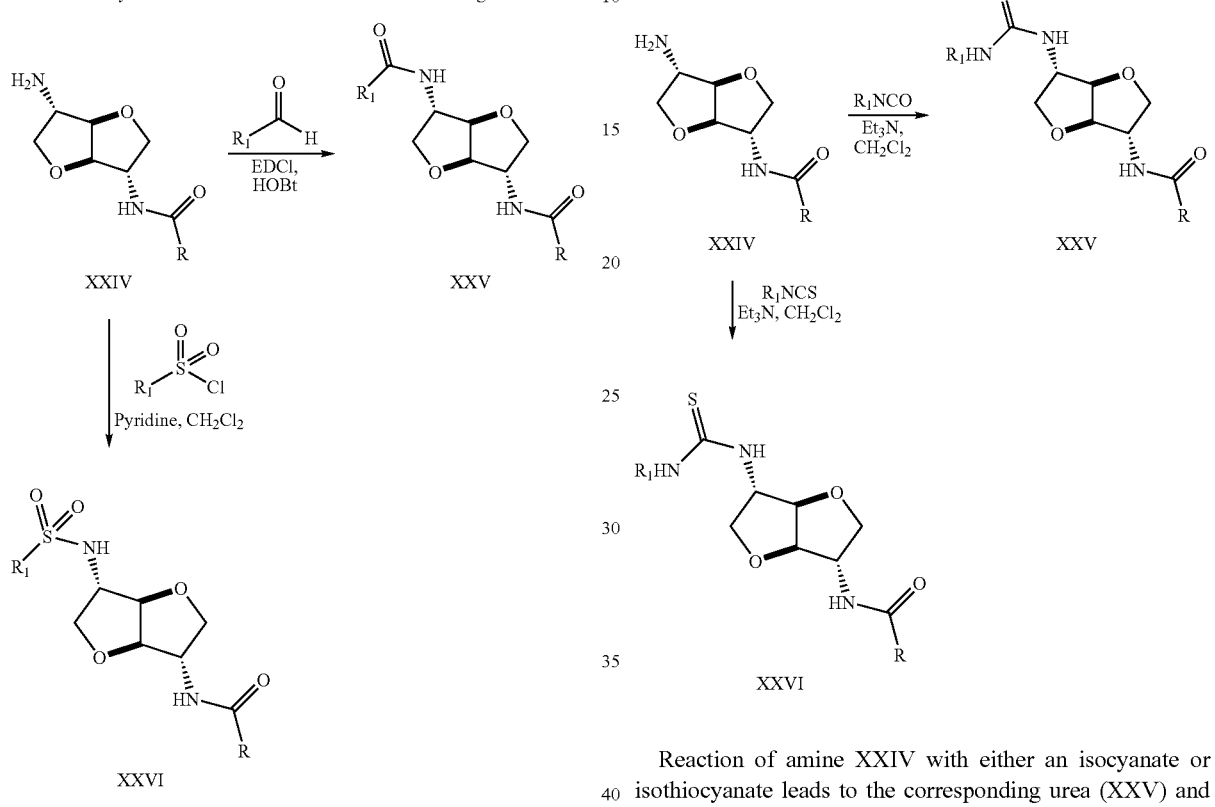

Reaction of amine XXIV with either an isocyanate or isothiocyanate leads to the corresponding urea (XXV) and thiourea (XXVI) derivatives.

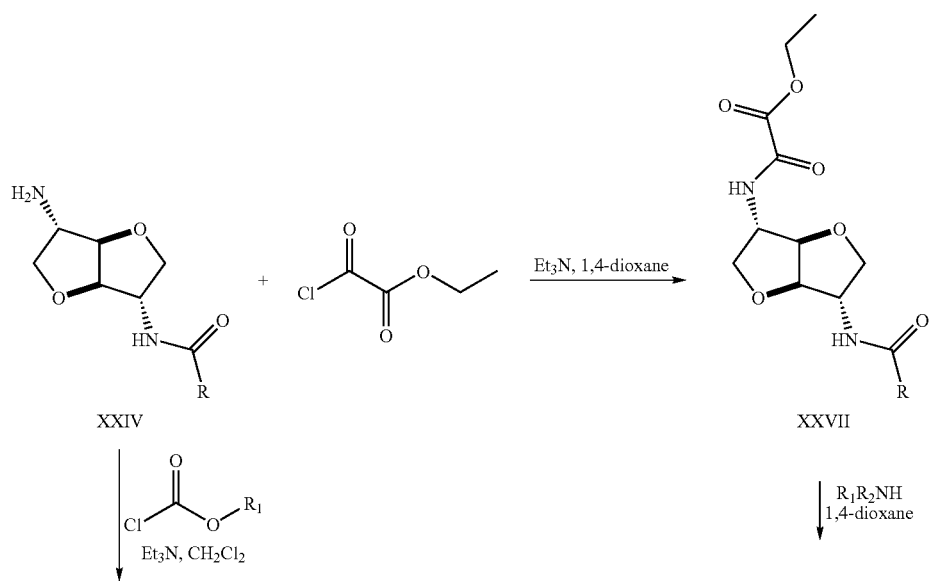

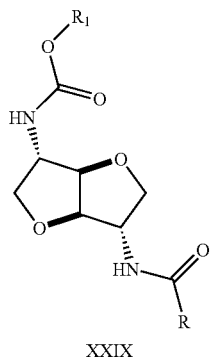

XXIX

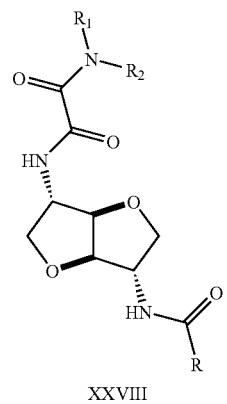

XXVIII

Oxalamide-containing isosorbide derivative XXVII can be accessed through reaction of amine XXIV with ethyl 2-chloro-2-oxoacetate in the presence of triethylamine, followed by substitution of the ester functionality with an amine substituent. In addition, amine XXVII can be reacted with a chloroformate of choice to provide carbamate XXIX.

Scheme 11. Synthesis of substituted amino isosorbide derivatives.

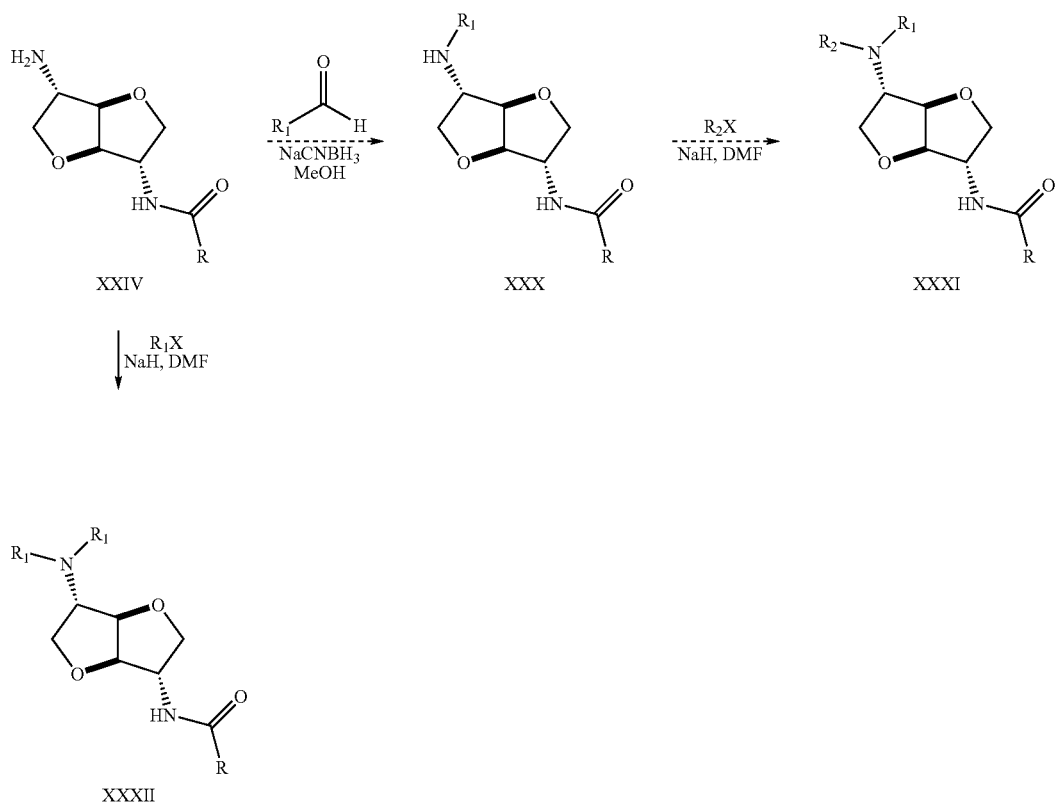

Reductive amination of a chosen aldehyde with amine XXIV in the presence of sodium cyanoborohydride can provide monosubstituted amine XXX. Further reaction of the monsubstituted amine with an equivalent of R2X and base would provide differentially substituted amine XXXI. In addition, N,N-disubstituted analogs can be synthesized through reaction of amine XXIV with two equivalents of a halide in the presence of NaH to provide N,N-disubstituted derivatives XXII.

Scheme 12. Alternative methods for accessing symmetrically and unsymmetrically substituted isosorbide derivatives.

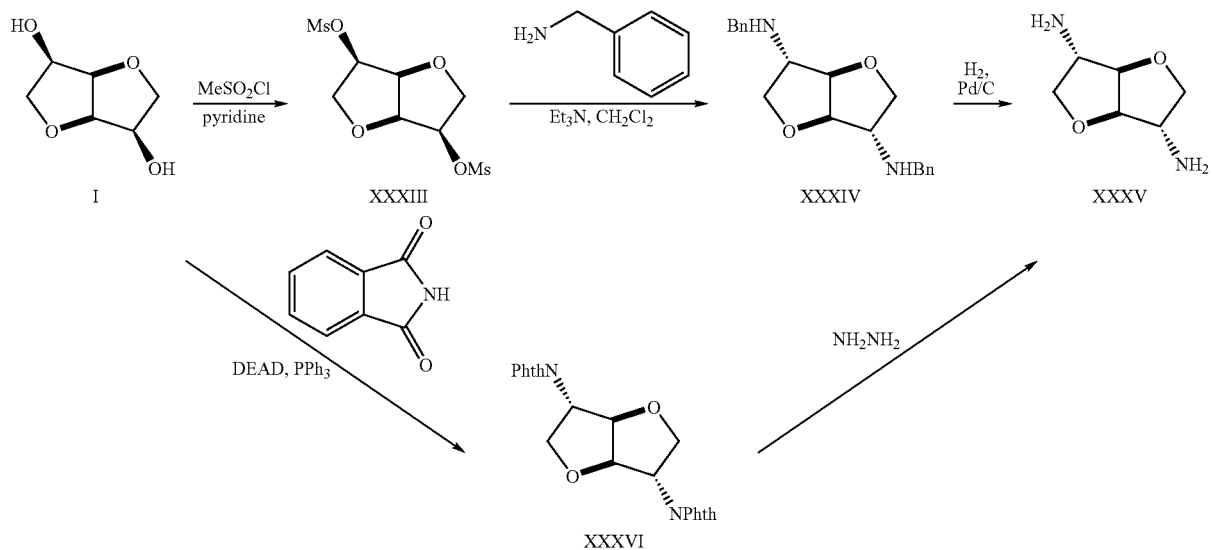

A further method for synthesis of the isosorbide analogs without the use of an azide group, can be carried out by mesylate protection of diol I. Displacement of the bismesylate with benzylamine, followed by catalytic hydrogenolysis provides diamine XXXV. Alternatively Mitsunobu reaction of diol I with phthalimide, triphenylphosphine and diethylazodicarboxylate provides bisphthalimide derivative XXXVI. Removal of the phthalimide protecting groups with hydrazine yields diamine XXXV.

Scheme 13. Reaction of diamine to form amides and sulfonamides.

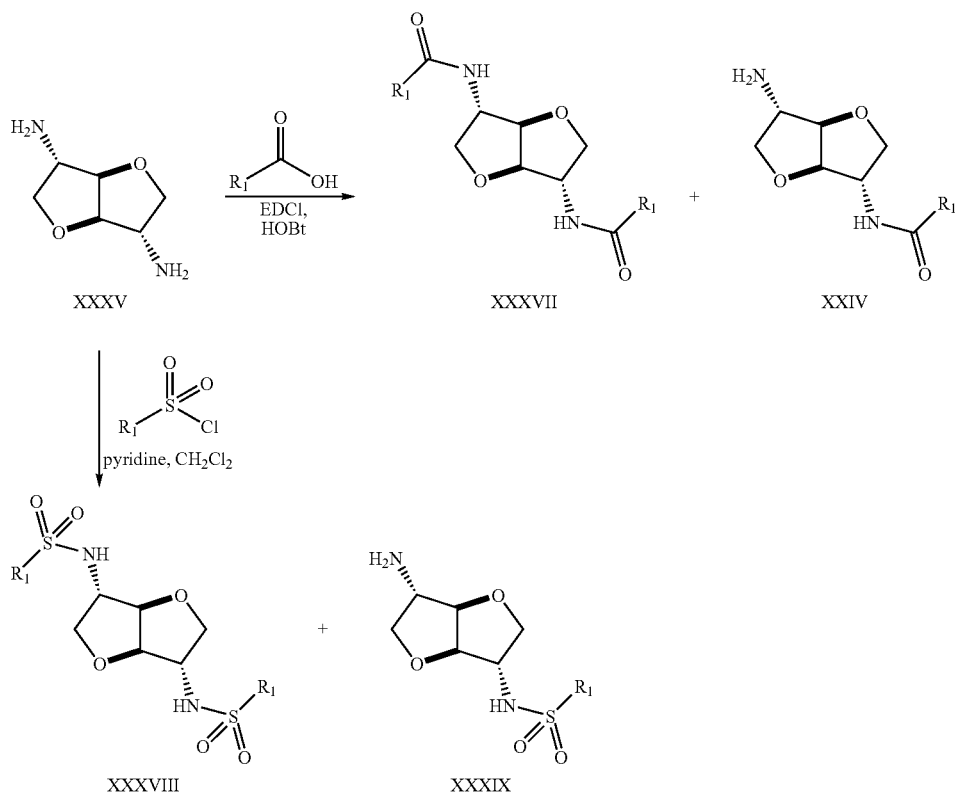

Diamine XXXV can be reacted with a carboxylic acid in the presence of HOBt and EDCI to provide both the bisamide XXXVII and the monoamide XXIV. The monoamide can be further elaborated using chemistry discussed in Schemes 8-11.

Scheme 14. Reaction of diamine to form ureas and thioureas.

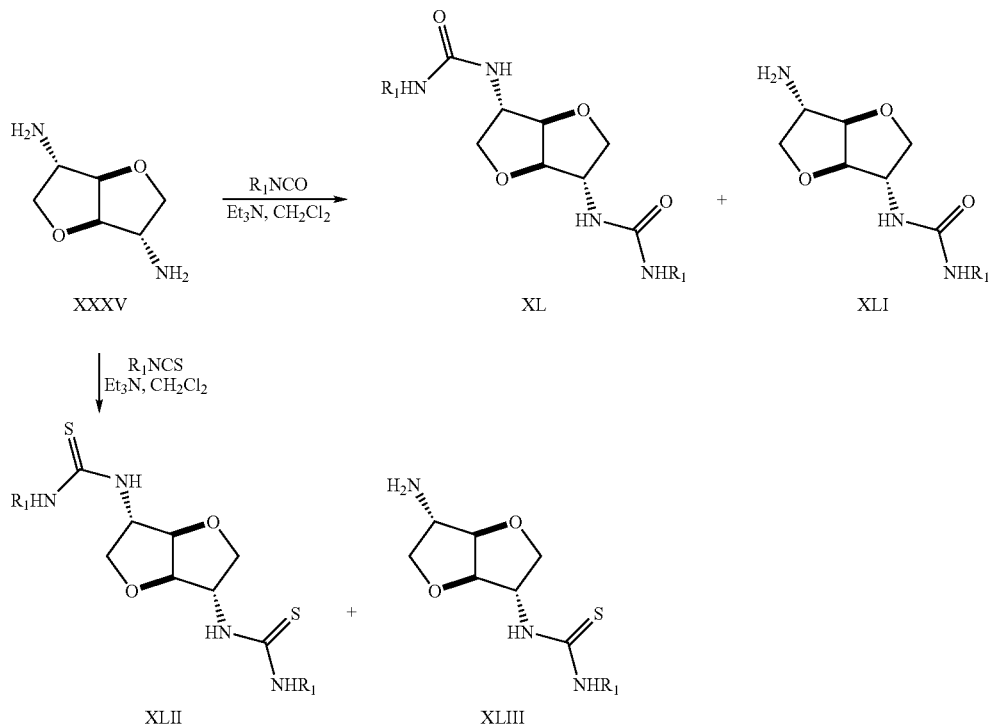

Symmetrically substituted urea XL can be accomplished through reaction of diamine XXXV with an isocyanate in the presence of triethylamine. In addition, the monourea may be synthesized in this way. Similarly, the symmetrically disubstituted and monosubstituted thio ureas XLII and XLIII respectively can be synthesized by reaction of diamine XXXV with an isothiocyanate. The monosubstituted urea and thiourea can then be elaborated through functionalization of the amine using chemistry described in Schemes 8-11.

Scheme 15. Synthesis of mono and disubstituted oxalamides and carbamates.

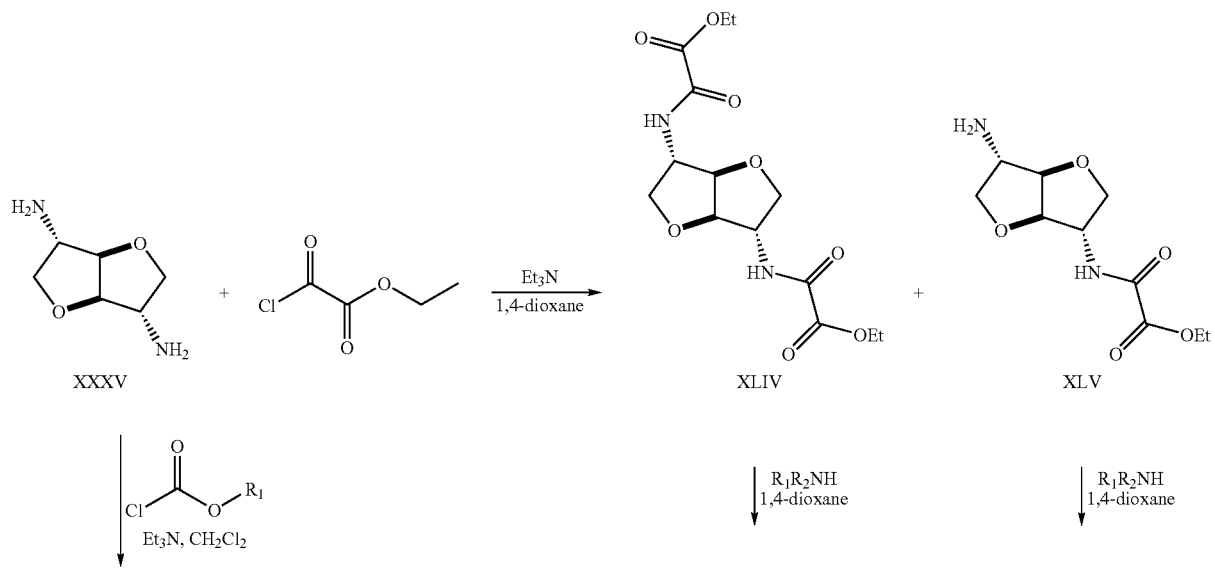

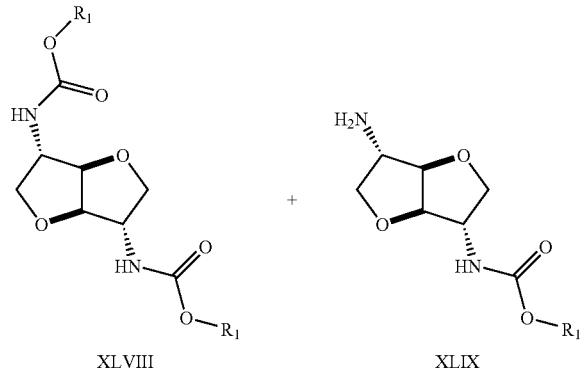
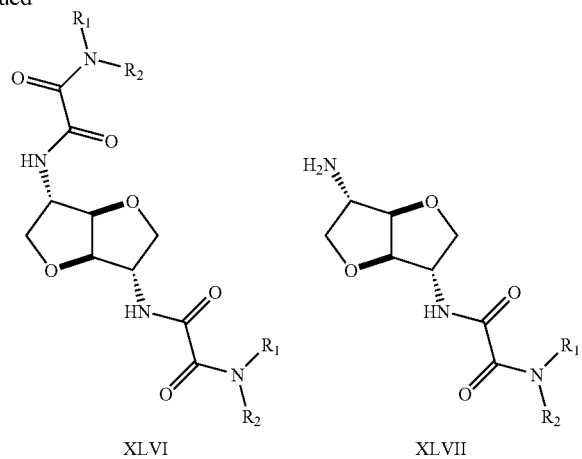

Reaction of diamine XXXV with ethyl 2-chloro-2-oxoacetate can provide symmetrically disubstituted ester XLIV as well as mono-ester XLV. Further reaction of both XLIV and XLV can result in formation of oxalamides XLVI and XLVII. In addition, reaction of diamine XXXV with a chloroformate in the presence of triethylamine can yield symmetrically disubstituted carbamates XLVIII and monocarbamate XLIX.

diamine XLXII or it can be reacted with a halide in the presence of NaH to provide substituted amine XLXIV. Additionally, differentially substituted diamine XLXII can be reacted with a halide in the presence of NaH to provide substituted amine XLXV. To provide a diamine with equivalent substitution, amine XXXV can be reacted with a halide in the presence of NaH to provide compound XLXVI.

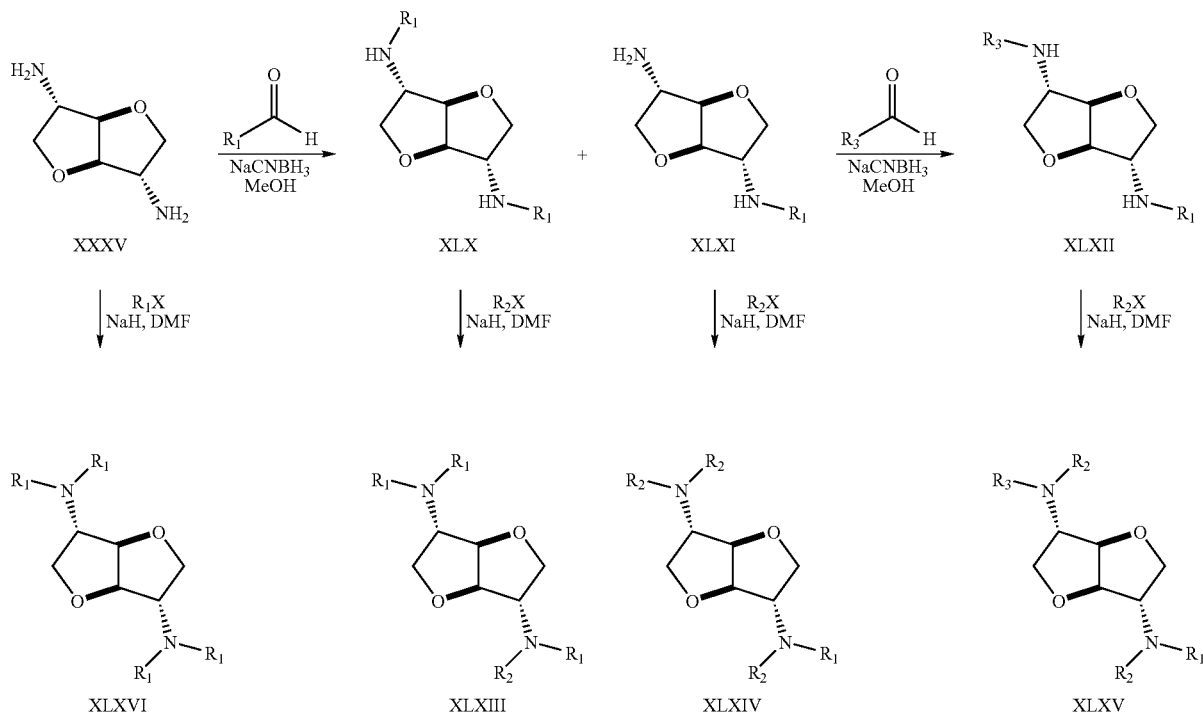

Reductive amination of an aldehyde of choice with diamine XXXV can provide both disubstituted and monosubstituted amines XLX and XLXI. Further reaction of structure XLX with a halide in the presence of NaH will provide symmetrical, differentially substituted amino compound XLXIII. Unsymmetrical amine XLXI can then be treated with either an aldehyde to provide differentially substituted Measuring the Biological Activity of the Compounds of the Invention In Vitro hT1R1/hT1R3 Activation Assay:

An HEK293 cell line derivative (See e.g., Chandrashekar, et al., Cell (2000) 100: 703-711) which stably expresses Gα15 and hT1R1/hT1R3 under an inducible promoter (see WO 03/001876 A2) was used to identify compounds with umami tasting properties.

Compounds of the present invention were initially selected based on their activity on the hT1R1/hT1R3-HEK293-Gα15 cell line. Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated clone I-17) were seeded into 384-well plates (at approximately 48,000 cells per well) in a medium containing Dulbecco's modified Eagle's medium (DMEM) supplemented with GlutaMAX (Invitrogen, Carlsbad, Calif.), 10% dialyzed fetal bovine serum (Invitrogen, Carlsbad, Calif.), 100 Units/ml Penicillin G, 100 µg/ml Streptomycin (Invitrogen, Carlsbad, Calif.) and 60 pM mifepristone (to induce expression of hT1R1/hT1R3, (see WO 03/001876 A2). I-17 cells were grown for 48 hours at 37° C. I-17 cells were then loaded with the calcium dye Fluo-3AM (Molecular Probes, Eugene, Oreg.), 4 µM in a phosphate buffered saline (D-PBS) (Invitrogen, Carlsbad, Calif.), for 1.5 hours at room temperature. After replacement with 25 µl D-PBS, stimulation was performed in the FLIPR instrument and at room temperature by the addition of 25 µl D-PBS supplemented with different stimuli at concentrations corresponding to twice the desired final level. Receptor activity was quantified by determining the maximal fluorescence increases (using a 480 nm excitation and 535 nm emission) after normalization to basal fluorescence intensity measured before stimulation.

For dose-responses analysis, stimuli were presented in duplicates at 10 different concentrations ranging from 1.5 nM to 30 µM. Activities were normalized to the response obtained with 60 mM monosodium glutamate, a concentration that elicits maximum receptor response. $EC_{50}$s (concentration of compound that causes 50% activation of receptor) were determined using a non-linear regression algorithm, where the Hill slope, bottom asymptotes and top asymptotes were allow to vary. Identical results were obtained when analyzing the dose-response data using commercially available software for non-linear regression analysis such as GraphPad PRISM (San Diego, Calif.). All compounds listed in all of the Examples herein have been tested and each have an $EC_{50}$ of 30 µM or less.

In order to determine the dependency of hT1R1/hT1R3 for the cell response to different stimuli, selected compounds were subjected to a similar analysis on I-17 cells that had not been induced for receptor expression with mifepristone (designated as un-induced I-17 cells). The un-induced I-17 cells do not show any functional response in the FLIPR assay to monosodium glutamate or other umami-tasting substances. Compounds were presented to un-induced umami cells at 10 µM-or three times the maximum stimulation used in the dose-response analysis. Compounds covered in this document do not show any functional response when using un-induced umami cells in the FLIPR assay.

Time-Intensity Testing Protocol
Overview: Panelists Evaluate Various Solutions for Umami Intensity Over Time.
General procedure: Samples presented to panelists include various concentrations of MSG and compounds of interest. Samples may contain 0.1% ethanol to assist in dissolving compounds into solution. Samples are three-digit blind coded and served in 20 ml volumes. Samples are presented to panelists in randomized, counterbalanced order. All data is collected using the Compusense five software program. Umami intensity is rated on a scale from 0 to 100 (0=no umami intensity; 100=strong umami intensity). Panelists sip a sample and begin rating umami intensity. Panelists move the mouse on the horizontal scale to correspond to the umami intensity they perceive. Panelists continue rating the intensity for 70 seconds, and then expectorate the sample. The software program records an intensity score for each panelist for each 1 second period during the sample evaluation.

After tasting each sample, panelists sip and swish water in the mouth for a few seconds and expectorate. They may repeat this several times. Panelists wait 30 minutes before tasting the next sample.

Data analysis: Time-intensity curves are created for each of the samples and various parameters of the test are compared statistically.

To create the graphical representation of the sample: For each of the 70 seconds of the evaluation, panelists individual scores are averaged and presented graphically. For example, each panelist's intensity score at time=0 seconds is averaged and plotted. The same calculation is made for each of the 70 seconds to create the time-intensity curve.

To evaluate the Time to Maximum Intensity parameter: A time-intensity curve is created for each panelist. Each panelist's graph shows their individual point of maximum umami intensity, and the specific time to maximum is recorded. The specific time scores for each panelist are averaged. Next, the average scores for the various samples are compared using ANOVA, and multiple comparisons are performed using Tukey's Honestly Significant Difference test at alpha=0.05.

Example 1 Comparison to MSG:

FIG. 1 displays a graphical representation of the average umami intensity ratings over a 70 second period for three samples:

All samples were made in Low Sodium Buffer (LSB) at pH 7.1.

Sample 1: 12 mM Monosodium Glutamate (MSG)
Sample 2: 16 mM Monosodium Glutamate (MSG)
Sample 3: 15 ppm (41.62 uM) N-((3S,3αR,6S,6αR)-6-(4-(cyclohexylmethyl)-1H-1,2,3-triazol-1-yl)hexahydrofuro[3,2-b]furan-3-yl)cyclopropanecarboxamide (Example 1)

Sample 3 quickly increase in umami intensity and has an average time to maximum intensity of 14.9 seconds (see table 1). It reached an average maximum intensity of 57 (see Table 2) and then gradually decreased in umami intensity over time.

Sample 2 has an average time to maximum intensity of 17 seconds (see Table 1) which was two seconds longer than Sample 3. Sample 2 also has an average maximum umami intensity of 53.8 (see Table 2) which was slightly less than Sample 3.

Tables 1 and 2 display multiple comparisons calculated using Tukey's HSD test for the average time to maximum intensity and the average intensity at maximum. Sample 2 and Sample 3 were not significantly different for both average time to maximum intensity (Table 1) and average intensity at maximum (Table 2) (p>0.1). Sample 3 was rated significantly more savory than Sample 1 (Table 2) (p<0.05).

TABLE 1

Average Time-to-Max, n = 33 (17 Panelists × 1 rep × day 1 and 16 panelists × 1 rep × day 2). Tukey's Value = 6.796 (α = 0.05), 6.014 (α = 0.10).

| Treatment | Average | SD | St Er | Tukey (5%) | Tukey (10%) |
|---|---|---|---|---|---|
| Sample 3 | 14.9 | 9.8 | 1.7 | a | a |
| Sample 1 | 15.9 | 13.1 | 2.3 | a | a |
| Sample 2 | 17.7 | 15.1 | 2.6 | ab | ab |

TABLE 2

Average Intensity-at-Max, n = 33 (17 Panelists × 1 rep × day 1 and 16 panelists × 1 rep × day 2). Tukey's Value = 11.085 (α = 0.05), 9.810 (α = 0.10).

| Treatment | Average | SD | St Er | Tukey (5%) | Tukey (10%) |
|---|---|---|---|---|---|
| Sample 1 | 45.3 | 19.3 | 3.4 | a | a |
| Sample 2 | 53.8 | 19.6 | 3.4 | ab | ab |
| Sample 3 | 57 | 21.4 | 3.7 | bc | bc |

Figure 2:
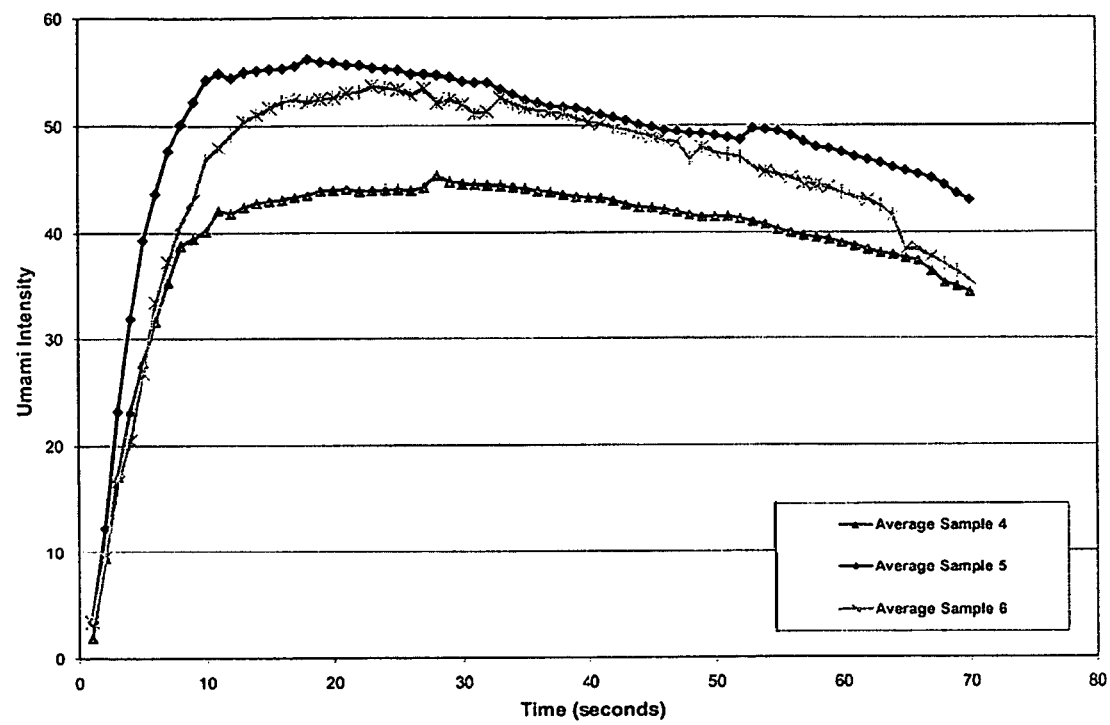
FIG. 2 is a graph showing the average umami intensity ratings over a 70 seconds period for three samples.

Example 29 Comparison to MSG:

FIG. 2 displays a graphical representation of the average umami intensity ratings over a 70 second period for three samples:

All samples were made in Low Sodium Buffer (LSB) at pH 7.1.

Sample 4: 12 mM Monosodium Glutamate (MSG)

Sample 5: 16 mM Monosodium Glutamate (MSG)

Sample 6: 2.5 ppm (6.86 uM) N-((3S,3αR,6S,6αR)-6-(4-cyclohexylbutanamido)-hexahydrofuro[3,2-b]furan-3-yl)cyclopropanecarboxamide (Example 29)

Sample 6 quickly increases in umami intensity and has an average time to maximum intensity of 18.3 seconds (see Table 3). It reached an average maximum intensity of 57.9 (see Table 4) and then gradually decreased in umami intensity over time.

Sample 5 has an average time to maximum intensity of 16.3 seconds (see Table 3) which was two seconds shorter than Sample 6. Sample 5 also has an average maximum umami intensity of 62.9 (see Table 4) which was slightly more than Sample 6.

Tables 3 and 4 display multiple comparisons calculated using Tukey's HSD test for the average time to maximum intensity and the average intensity at maximum. Sample 4, Sample 5 and Sample 6 were not significantly different for average time to maximum intensity (Table 3). Sample 4 and Sample 5 showed significantly different average intensity at max (Table 4), while Sample 6 was not significantly different from either Sample 4 or Sample 5 (Table 4) (p>0.1).

TABLE 3

Average Time-to-Max, n = 36 (18 Panelists × 2 rep). Tukey's Value = 6.712 (α = 0.05).

| Treatment | Average | SD | St Er | Tukey (5%) |
|---|---|---|---|---|
| Sample 5 | 16.3 | 13.0 | 2.2 | a |
| Sample 6 | 18.3 | 9.0 | 1.5 | a |
| Sample 4 | 18.8 | 14.3 | 2.4 | a |

TABLE 4

Average Intensity-at-Max, n = 36 (18 Panelists × 2 rep). Tukey's Value = 12.020 (α = 0.05)

| Treatment | Average | SD | St Er | Tukey (5%) |
|---|---|---|---|---|
| Sample 4 | 49.8 | 23.0 | 3.8 | a |
| Sample 6 | 57.9 | 25.8 | 4.3 | ab |
| Sample 5 | 62.9 | 21.6 | 3.6 | b |

EXAMPLES

The following examples are given to illustrate a variety of exemplary embodiments of the invention and are not intended to be limiting in any manner.

Example 1

N-((3S,3αR,6S,6αR)-6-(4(cyclohexylmethyl)-1H-1,2,3-triazol-1-yl)-hexahydrofuro[13,2-b]furan-3-yl)cyclopropanecarboxamide

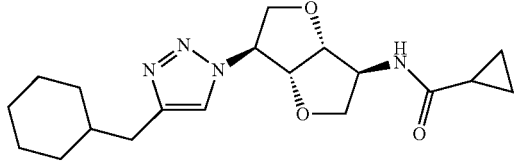 [SMILES: O=C(N[C@H]1CO[C@H]2[C@@H]1OC[C@@H]2n1cc(CC2CCCCC2)nn1)C1CC1]

A solution of (3S, 3αR, 6S, 6αR)-6-(4-(cyclohexylmethyl)-1H-1,2,3-triazol-1-yl)-hexahydrofuro[3,2-b]furan-3-amine (example 1a) (1.46 g, 5.0 mmol), cyclopropane carboxylic acid (418 uL, 5.0 mmol), EDCI (960 mg, 5.0 mmol) and HOBt (676 mg, 5.0 mmol) in a 4:1 mixture of $CH_2Cl_2$:DMF (50 mL) was stirred at rt overnight. Upon completion, the reaction mixture was filtered, and the filtrate was diluted with $CH_2Cl_2$ and washed with 0.5 N HCl, water, saturated $NaHCO_3$ and brine. The organic layer was dried over $MgSO_4$, filtered and concentrated to provide N-((3S,3αR,6S,6αR)-6-(4-(cyclohexylmethyl)-1H-1,2,3-triazol-1-yl)hexahydro-furo-[3,2-b]furan-3-yl)cyclopropanecarboxamide (880 mg, 53%) as an off-white solid, which was recrystallized from $CH_2Cl_2$/hexane. $^1H$ NMR (DMSO-$d_6$, 400 MHz): 0.64 (m, 4H), 0.90 (m, 2H), 1.13 (m, 3H), 1.52 (m, 2H), 1.63 (m, 4H), 2.47 (m, 2H), 3.71 (dd, 1H, J=9.2 Hz, 2.4 Hz), 3.95 (dd, 1H, J=9.6 Hz, 4.8 Hz), 4.02 (dd, 1H, J=10.0, 2.8 Hz), 4.16 (m, 2H), 4.59 (d, 1H, J=3.6 Hz), 4.81 (d, 1H, J=4.0 Hz), 5.16 (s, 1H), 7.87 (s, 1H), 8.39 (d, 1H, J=7.2 Hz). MS 361 (MH$^+$).

Example 1a (3S,3αR, 6S,6αR)-6-(4-(cyclohexylmethyl)-1H-1,2,3-triazol-1-yl)-hexahydrofuro[3,2-b]furan-3-amine To a solution of 1-((3S,3αR,6S,6αR)-6-azidohexahydrofuro[3,2-b]furan-3-yl)-4-(cyclohexylmethyl)-1H-1,2,3-triazole 2-amino-6-propoxybenzonitrile (example 1b) (5.26 g, 16.52 mmol) in MeOH (45 mL), was added a catalytic amount of 10% Pd/C. The reaction mixture was hydrogenated on a Parr shaker overnight at 40 psi. Upon completion, the reaction was filtered through celite and concentrated to provide (3S,3αR,6S,6αR)-6-(4-(cyclohexyl-methyl)-1H-1,2,3-triazol-1-yl)hexahydrofuro[3,2-b]furan-3-amine (4.35 g, quant.) as an off-white solid. $^1H$ NMR (DMSO-$d_6$, 400 MHz): 0.94 (m, 2H), 1.18 (m, 3H), 1.65 (m, 7H), 2.49 (s, 2H), 3.58 (dd, J=8.8, 1.6 Hz, 1H), 3.89 (dd, J=8.5, 4.2 Hz, 1H), 4.04 (dd, J=9.9, 2.4 Hz, 1H), 4.13 (dd, J=9.9, 5.2 Hz, 1H), 4.45 (d, J=3.8 Hz, 1H), 4.83 (d, J=4.2 Hz, 1H), 5.11 (m, 1H), 7.88 (s, 1H). MS 293 (MH$^+$).

Example 1b 1-((3S,3αR, 6,6αR)-6-azidohexahydrofuro[3,2-b]furan-3-yl)-4-(cyclohexylmethyl)-1H-1,2,3-triazole 2

(3S,3αR,6S,6αR)-3,6-diazidohexahydrofuro[3,2-b]furan (example 1c) (7.9 g, 28.04 mmol), prop-2-ynylcyclohexane (4.05 mL, 28.04 mmol), CuSO$_4$ (179 mg, 1.12 mmol) and sodium ascorbate (1.11 g, 5.61 mmol) were dissolved in a 5:1 mixture of H$_2$O:t-butanol (240 mL), and stirred at rt overnight. The precipitated product was collected by filtration, and taken up in MeOH. The insoluble impurity was removed by filtration, and the filtrate was concentrated in vacuo to provide 1-((3S,3αR,6S,6αR)-6-azidohexahydrofuro[3,2-b]furan-3-yl)-4-(cyclohexylmethyl)-1H-1,2,3-triazole (5.26 g, 53%) as a white solid. $^1$H NMR (DMSO-d$_6$, 400 MHz): 0.90 (m, 2H), 1.14 (m, 3H), 1.61 (m, 6H), 2.46 (s, 2H), 3.90 (dd, J=10.4, 1.5 Hz, 1H), 3.96 (dd, J=10.4, 4.1 Hz, 1H), 4.04 (dd, J=10.4, 3.1 Hz, 1H), 4.16 (dd, J=10.2, 5.6 Hz, 1H), 4.32 (m, 1H), 4.75 (d, J=4.4 Hz, 1H), 4.86 (d, J=4.4 Hz, 1H), 5.17 (m, 1H), 7.88 (s, 1H). MS 319 (MH$^+$).

Example 1c (3S,3αR,6S,6αR)-3,6-diazidohexahydrofuro[3,2-b]furan

To a solution of (3R,3αS,6R,6αS)-hexahydrofuro[3,2-b]furan-3,6-diyl bis(trifluoro-methanesulfonate) (example 1d) (7.86 g, 19.16 mmol) in DMF (200 mL), was added NaN$_3$ (3.86 g, 59.39 mmol). The reaction mixture was heated to 120° C. for 2 h, cooled to rt and concentrated in vacuo. The residue was diluted with CH$_2$Cl$_2$, and the solid salts were removed by filtration. The filtrate was washed with H$_2$O and brine, dried over MgSO$_4$, filtered and concentrated to provide (3S,3αR,6S,6αR)-3,6-diazidohexahydrofuro[3,2-b]furan (2.5 g, 67%) as a light brown oil. $^1$H NMR (CDCl$_3$ 400 MHz): 3.90 (dd, J=10.4, 4.2 Hz, 2H), 3.95 (dd, J=10.3, 1.5 Hz, 2H), 4.08 (m, 2H), 4.63 (s, 2H).

Example 1d (3R,3αS,6R,6αS)-hexahydrofuro[3,2-b]furan-3,6-diyl bis(trifluoromethanesulfonate)

To a solution of (3R,3αR,6R,6αR)-hexahydrofuro[3,2-b]furan-3,6-diol (3.0 g, 20 mmol) and pyridine (3.9 mL, 48 mmol) in CH$_2$Cl$_2$ (100 mL) at 0° C., was added triflic anhydride (7.9 mL, 48 mmol) dropwise. After complete addition, the reaction was slowly warmed to rt, and stirred under N$_2$ overnight. Upon completion, the reaction mixture was diluted with CH$_2$Cl$_2$, washed with 1N HCl, water, sat'd NaHCO$_3$, water and brine. The organic layer was dried over MgSO$_4$, filtered and concentrated to provide (3R,3αS,6R,6αS)-hexahydrofuro[3,2-b]furan-3,6-diyl bis(trifluoromethanesulfonate) (7.86 g, 96%) as a brown gel. $^1$H NMR (CDCl$_3$ 400 MHz): 4.17 (d, J=5.0 Hz, 4H), 4.78 (m, 2H), 5.23 (m, 2H), 4.63 (s, 2H).

Example 2

N-((3S,3αR,6S,6αR)-6-(4-(cyclohexylmethyl)-1H-1,2,3-triazol-1-yl)-hexahydrofuro[3,2-b]furan-3-yl)benzamide

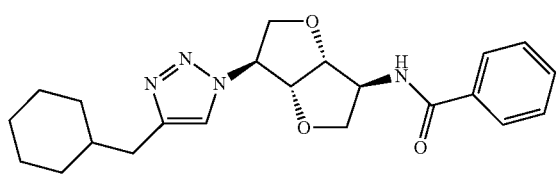 [SMILES: O=C(N[C@H]1CO[C@H]2[C@@H]1OC[C@@H]2n1cc(CC2CCCCC2)nn1)c1ccccc1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and benzoic acid to provide N-((3S,3αR,6S,6αR)-6-(4-(cyclohexylmethyl)-1H-1,2,3-triazol-1-yl)-hexahydrofuro[3,2-b]furan-3-yl)benzamide. MS 397 (MH$^+$).

Example 3

N-((3S,3αR,6S,6αR)-6-(4-(cyclohexylmethyl)-1H-1,2,3-triazol-1-yl)-hexahydrofuro[3,2-b]furan-3-yl)-2-cyclopentylacetamide

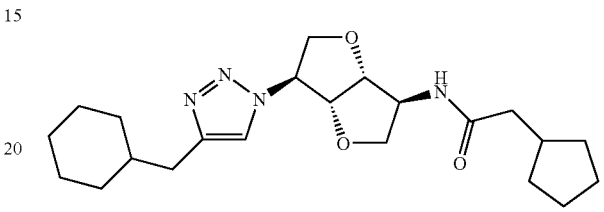

Prepared as in example 1 from (3S,3αR,6S,6αR)-6-(4-(cyclohexylmethyl)-1H-1,2,3triazol-1-yl)-hexahydrofuro[3,2-b]furan-3-amine (example 1a) and 2-cyclopentylacetic acid to provide N-((3S,3 αR,6S,6αR)-6-(4-(cyclohexylmethyl)-1H-1,2,3-triazol-1-yl)-hexahydrofuro-[3,2-b]furan-3-yl)-2-cyclopentylacetamide. MS 403 (MH$^+$).

Example 4

N-((3S,3αR,6S,6αR)-6-(4(cyclohexylmethyl)-1H-1,2,3-triazol-1-yl)-hexahydrofuro[3,2-b]furan-3-yl) propionamide

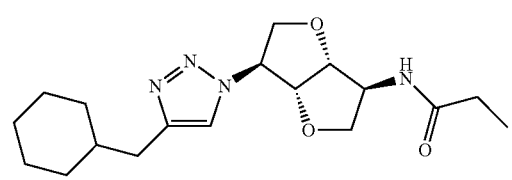 [SMILES: CCC(=O)N[C@H]1CO[C@H]2[C@@H]1OC[C@@H]2n1cc(CC2CCCCC2)nn1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and propionic acid to provide N-((3S,3αR,6S,6αR)-6-(4-(cyclohexylmethyl)-1H-1,2,3-triazol-1-yl)-hexahydrofuro[3,2-b]furan-3-yl) propionamide. MS 349 (MH$^+$).

Example 5

N-((3S,3αR,6S,6αR)-6-(4-(cyclohexylmethyl)-1H-1,2,3-triazol-1-yl)-hexahydrofuro[3,2-b]furan-3-yl) picolinamide

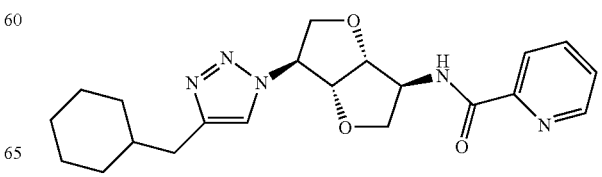

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and picolinic acid to provide N-((3S,3αR,6S,6αR)-6-(4-(cyclohexylmethyl)-1H-1,2,3-triazol-1-yl)-hexahydrofuro[3,2-b]furan-3-yl) picolinamide. MS 398 (MH⁺).

Example 6

N-((3S,3αR,6S,6αR)-6-(4-(cyclohexylmethyl)-1H-1,2,3-triazol-1-yl)-hexahydrofuro[3,2-b]furan-3-yl) nicotinamide

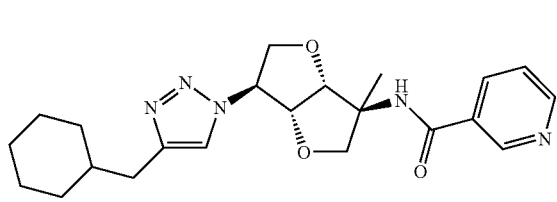 [SMILES: C[C@]1(NC(=O)c2cccnc2)CO[C@@H]2[C@@H](n3cc(CC4CCCCC4)nn3)CO[C@@H]21]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and nicotinic acid to provide N-((3S,3αR,6S,6αR)-6-(4-(cyclohexylmethyl)-1H-1,2,3-triazol-1-yl)-hexahydrofuro[3,2-b]furan-3-yl) nicotinamide. MS 398 (MH⁺).

Example 7

N-((3S,3αR,6S,6αR)-6-(4-(cyclohexylmethyl)-1H-1,2,3-triazol-1-yl)-hexahydrofuro[3,2-b]furan-3-yl) furan-2-carboxamide

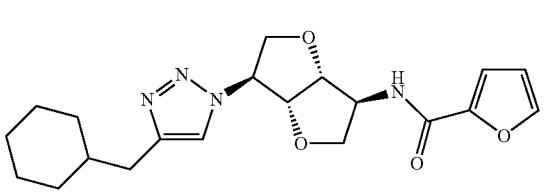 [SMILES: O=C(N[C@H]1CO[C@H]2[C@@H]1OC[C@@H]2n1cc(CC2CCCCC2)nn1)c1ccco1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and furan-2-carboxylic acid to provide N-((3S,3αR,6S,6αR)-6-(4-(cyclohexylmethyl)-1H-,2,3-triazol-1-yl)-hexahydrofuro-[3,2-b]furan-3-yl)furan-2-carboxamide. MS 387 (MH⁺).

Example 8

N-((3S,3αR,6S,6αR)-6(4-(cyclohexylmethyl)-1H-1,2,3-triazol-1-yl)-hexahydrofuro[3,2-b]furan-3-yl) furan-3-carboxamide

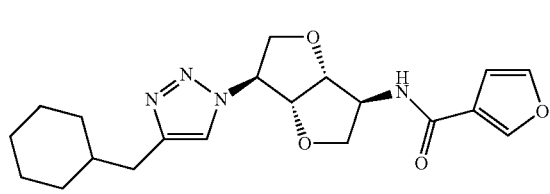 [SMILES: O=C(N[C@H]1CO[C@H]2[C@@H]1OC[C@@H]2n1cc(CC2CCCCC2)nn1)c1ccoc1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and furan-3-carboxylic acid to provide N-((3S,3 αR,6S,6αR)-6-(4-(cyclohexylmethyl)-1H-1,2,3-triazol-1-yl)-hexahydrofuro[3,2-b]furan-3-yl)furan-2-carboxamide. MS 387 (MH⁺).

Example 9

N-((3S,3αR,6S,6αR)-6-(4-(cyclohexylmethyl)-1H-1,2,3-triazol-1-yl)-hexahydrofuro[3,2-b]furan-3-yl) thiophene-2-carboxamide

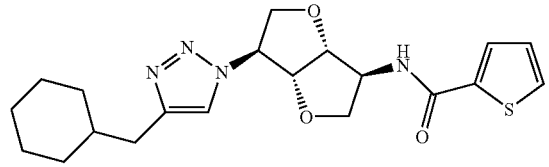 [SMILES: O=C(N[C@H]1CO[C@H]2[C@@H]1OC[C@@H]2n1cc(CC2CCCCC2)nn1)c1cccs1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and thiophene-2-carboxylic acid to provide N-((3S,3αR,6S,6αR)-6-(4-(cyclohexylmethyl)-1H-1,2,3-triazol-1-yl)-hexahydrofuro-[3,2-b]furan-3-yl)thiophene-2-carboxamide. MS 403 (MH⁺).

Example 10

N-((3S,3αR,6S,6αR)-6-(4-(cyclohexylmethyl)-1H-1,2,3-triazol-1-yl)-hexahydrofuro[3,2-b]furan-3-yl) thiophene-2-carboxamide

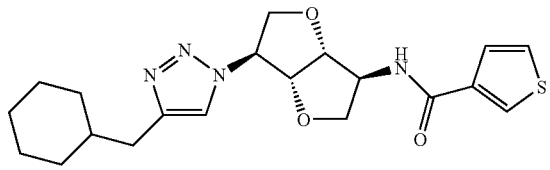

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and thiophene-3-carboxylic acid to provide N-((3S,3αR,6S,6αR)-6-(4-(cyclohexylmethyl)-1H-1,2,3-triazol-1-yl)-hexahydrofuro-[3,2-b]furan-3-yl)thiophene-2-carboxamide. MS 403 (MH⁺).

Example 11

N-((3S,3αR,6S,6αR)-6-(4-(cyclohexylmethyl)-1H-1,2,3-triazol-1-yl)-hexahydrofuro[3,2-b]furan-3-yl)-3-methylbenzamide

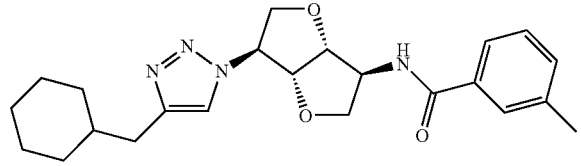 [SMILES: Cc1cccc(C(=O)N[C@H]2CO[C@H]3[C@@H]2OC[C@@H]3n2cc(CC3CCCCC3)nn2)c1]

Prepared as in example 1 from (3S,3αR,6S,6αR)-6-(4-(cyclohexylmethyl)-1H-1,2,3-triazol-1-yl)-hexahydrofuro

[3,2-b]furan-3-amine (example 1a) and 3-methylbenzoic acid to provide N-((3S,3αR,6S,6αR)-6-(4-(cyclohexylmethyl)-1H-1,2,3-triazol-1-yl)-hexahydrofuro[3,2-b]furan-3-yl)-3-methylbenzamide. MS 411 (MH+).

Example 12

N-((3S,3αR,6S,6αR)-6-(4-(cyclohexylmethyl)-1H-1,2,3-triazol-1-yl)-hexahydrofuro[3,2-b]furan-3-yl)-3-hydroxybenzamide

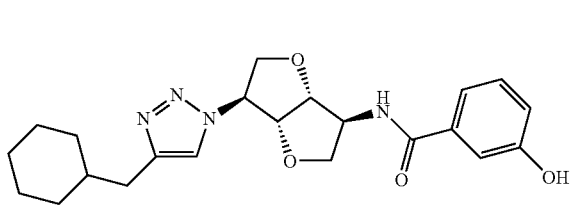 [SMILES: O=C(N[C@H]1CO[C@H]2[C@@H]1OC[C@@H]2n1cc(CC2CCCCC2)nn1)c1cccc(O)c1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 3-hydroxybenzoic acid to provide N-((3S,3αR,6S,6αR)-6-(4-(cyclohexylmethyl)-1H-1,2,3-triazol-1-yl)-hexahydrofuro[3,2-b]furan-3-yl)-3-hydroxybenzamide. MS 413 (MH+).

Example 13

3-cyano-N-((3S,3αR,6S,6αR)-6-(4-(cyclohexylmethyl)-1H-1,2,3-triazol-1-yl)-hexahydrofuro[3,2-b]furan-3-yl)benzamide

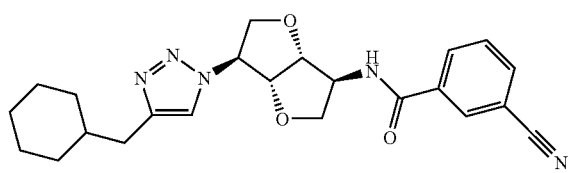 [SMILES: N#Cc1cccc(C(=O)N[C@H]2CO[C@H]3[C@@H]2OC[C@@H]3n2cc(CC3CCCCC3)nn2)c1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 3-cyanobenzoic acid to provide 3-cyano-N-((3S,3αR,6S,6αR)-6-(4-(cyclohexylmethyl)-1H-1,2,3-triazol-1-yl)-hexahydrofuro[3,2-b]furan-3-yl)benzamide. MS 422 (MH+).

Example 14 methyl 3-((3S,3αR,6S,6αR)-6-(4-(cyclohexylmethyl)-1H-1,2,3-triazol-1-yl)-hexahydrofuro[3,2-b]furan-3-ylcarbamoyl)benzoate

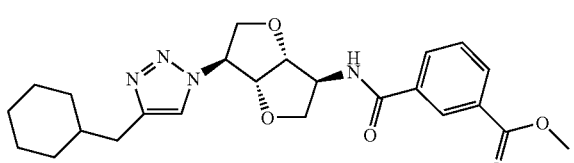

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 3-(methoxycarbonyl) benzoic acid to provide methyl 3-((3S,3αR,6S,6αR)-6-(4-(cyclohexylmethyl)-1H-1,2,3-triazol-1-yl)-hexahydrofuro[3,2-b]furan-3-ylcarbamoyl)benzoate. MS 455 (MH+).

Example 15

N-((3S,3αR,6S,6αR)-6-(4-(cyclohexylmethyl)-1H-1,2,3-triazol-1-yl)-hexahydrofuro[3,2-b]furan-3-yl)-3-methylfuran-2-carboxamide

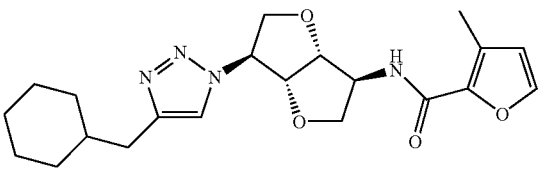 [SMILES: Cc1ccoc1C(=O)N[C@H]1CO[C@H]2[C@@H]1OC[C@@H]2n1cc(CC2CCCCC2)nn1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 3-methylfuran-2-carboxylic acid to provide N-((3S,3αR,6S,6αR)-6-(4-cyclohexylmethyl-1H-1,2,3-triazol-1-yl)-hexahydrofuro[3,2-b]furan-3-yl)-3-methylfuran-2-carboxamide. MS 401 (MH+).

Example 16

N-((3S,3αR,6S,6αR)-6(4-(cyclohexylmethyl)-1H-1,2,3-triazol-1-yl)-hexahydrofuro[3,2-b]furan-3-yl) isoxazole-5-carboxamide

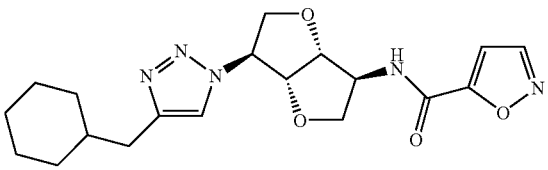 [SMILES: O=C(N[C@H]1CO[C@H]2[C@@H]1OC[C@@H]2n1cc(CC2CCCCC2)nn1)c1ccno1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and isoxazole-5-carboxylic acid to provide N-((3S,3 αR,6S,6αR)-6-(4-(cyclohexylmethyl)-1H-1,2,3-triazol-1-yl)-hexahydrofuro-[3,2-b]furan-3-yl)isoxazole-5-carboxamide. MS 388 (MH+).

Example 17

N-((3S,3αR,6S,6αR)-6-(4-(cyclohexylmethyl)-1H-1,2,3-triazol-1-yl)-hexahydrofuro[3,2-b]furan-3-yl)-1H-imidazole-5-carboxamide

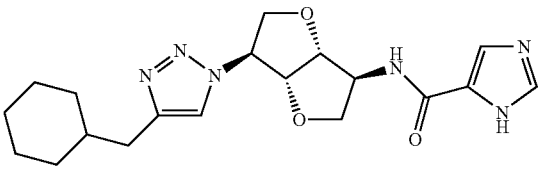 [SMILES: O=C(N[C@H]1CO[C@H]2[C@@H]1OC[C@@H]2n1cc(CC2CCCCC2)nn1)c1cnc[nH]1]

Prepared as in example 1 from (3S, 360 R,6S. 6αR)-6-(4-cyclohexylmethyl)-1H-1,2,3-triazol-1-yl)-hexahydrofuro[3,2-b]furan-3-amine (example 1a) and 1H-imidazole-5-carboxylic acid to provide N-((3S,3αR,6S,6αR)-6-4-

(cyclohexylmethyl)-1H-1,2,3-triazol-1-yl)-hexahydrofuro[3,2-b]furan-3-yl)-1H-imidazole-5-carboxamide. MS 387 (MH+).

Example 18

N-((3S,3αR,6S,6αR)-6-(4-(cyclohexylmethyl)-1H-1,2,3-triazol-1-yl)-hexahydrofuro[3,2-b]furan-3-yl)-1H-1,2,3-triazole-5-carboxamide

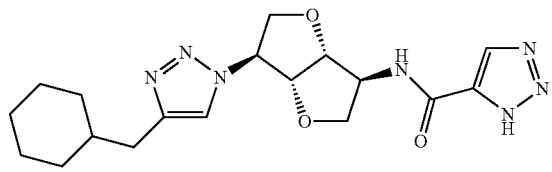 [SMILES: O=C(N[C@H]1CO[C@H]2[C@@H]1OC[C@@H]2n1cc(CC2CCCCC2)nn1)c1cnn[nH]1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 3H-[1,2,3]triazole-4-carboxylic acid to provide N-((3S,3αR,6S,6αR)-6-(4-(cyclohexylmethyl)-1H-1,2,3-triazol-1-yl)-hexahydrofuro[3,2-b]furan-3-yl)-1H-1,2,3-triazole-5-carboxamide. MS 388 (MH+).

Example 19

N-((3S,3αR,6S,6αR)-6-(4-(cyclohexylmethyl)-1H-1,2,3-triazol-1-yl)-hexahydrofuro[3,2-b]furan-3-yl)-1,3-dimethyl-1H-pyrazole-5-carboxamide

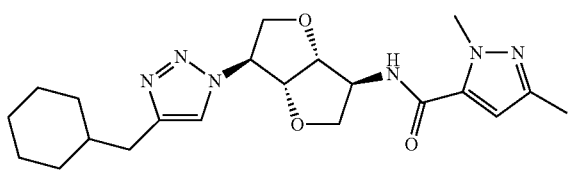 [SMILES: Cc1cc(C(=O)N[C@H]2CO[C@H]3[C@@H]2OC[C@@H]3n2cc(CC3CCCCC3)nn2)n(C)n1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 1,3-dimethyl-1H-pyrazole-5-carboxylic acid to provide N-((3S,3αR,6S,6αR)-6-(4-(cyclohexylmethyl)-1H-1,2,3-triazol-1-yl)-hexahydrofuro[3,2-b]furan-3-yl)-1,3-dimethyl-1H-pyrazole-5-carboxamide. MS 415 (MH+).

Example 20

N-((3S,3αR,6S,6αR)-6-(4-cyclohexylmethyl)-1H-1,2,3-triazol-1-yl)-hexahydrofuro[3,2-b]furan-3-yl)-1-methyl-1H-pyrrole-3-carboxamide

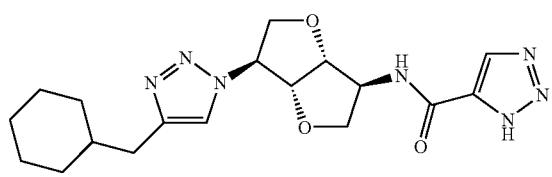 [SMILES: O=C(N[C@H]1CO[C@H]2[C@@H]1OC[C@@H]2n1cc(CC2CCCCC2)nn1)c1cnn[nH]1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 1-methyl-1H-pyrrole-3-carboxylic acid to provide N-((3S,3 αR,6S,6αR)-6-(4-(cyclohexylmethyl)-1H-1,2,3-triazol-1-yl)-hexahydrofuro[3,2-b]furan-3-yl)-1-methyl-1H-pyrrole-3-carboxamide. MS 400 (MH+).

Example 21

N-((3S,3αR,6S,6αR)-6-(4-(cyclohexylmethyl)-1H-1,2,3-triazol-1-yl)-hexahydrofuro[3,2-b]furan-3-yl)-1H-pyrazole-3-carboxamide

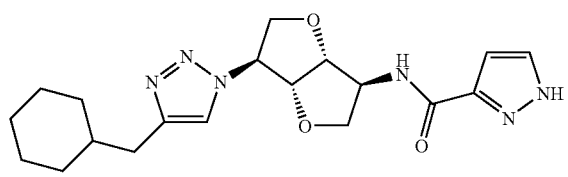 [SMILES: O=C(N[C@H]1CO[C@H]2[C@@H]1OC[C@@H]2n1cc(CC2CCCCC2)nn1)c1cc[nH]n1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 1H-pyrazole-3-carboxylic acid to provide N-((3S,3 αR,6S,6αR)-6-(4-(cyclohexylmethyl)-1H-1,2,3-triazol-1-yl)-hexahydrofuro[3,2-b]furan-3-yl)-1H-pyrazole-3-carboxamide. MS 387 (MH+).

Example 22

N-((3S,3αR,6S,6αR)-6-(4-(cyclohexylmethyl)-1H-1,2,3-triazol-1-yl)-hexahydrofuro[3,2-b]furan-3-yl)-1H-pyrazole-4-carboxamide

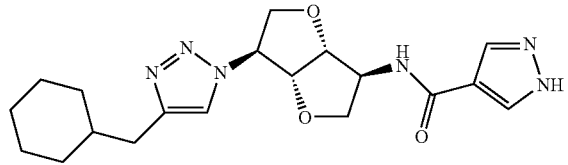 [SMILES: O=C(N[C@H]1CO[C@H]2[C@@H]1OC[C@@H]2n1cc(CC2CCCCC2)nn1)c1cn[nH]c1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 1H-pyrazole-4-carboxylic acid to provide N-((3S,3αR,6S,6αR)-6-(4-(cyclohexylmethyl)-1H-1,2,3-triazol-1-yl)-hexahydrofuro[3,2-b]furan-3-yl)-1H-pyrazole-4-carboxamide. MS 387 (MH+).

Example 23

N-((3S,3αR,6S,6αR)-6-(4-(cyclohexylmethyl)-1H-1,2,3-triazol-1-yl)-hexahydrofuro[3,2-b]furan-3-yl)-1-methyl-1H-imidazole-4-carboxamide

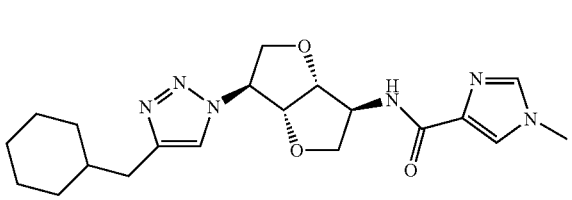 [SMILES: Cn1cnc(C(=O)N[C@H]2CO[C@H]3[C@@H]2OC[C@@H]3n2cc(CC3CCCCC3)nn2)c1]

Prepared as in example 1 from (3S,3αR,6S,6αR)-6-(4-(cyclohexylmethyl)-1H-1,2,3-triazol-1-yl)-hexahydrofuro

[3,2-b]furan-3-amine (example 1a) and 1-methyl-1H-imidazole-4-carboxylic acid to provide N-((3S,3αR,6S,6αR)-6-(4-(cyclohexylmethyl)-1H-1,2,3-triazol-1-yl)-hexahydrofuro[3,2-b]furan-3-yl)-1-methyl-1H-imidazole-4-carboxamide. MS 401 (MH$^+$).

Example 24

N-((3S,3αR,6S,6αR)-6-(4-(cyclohexylmethyl)-1H-1,2,3-triazol-1-yl)-hexahydrofuro[3,2-b]furan-3-yl)-1,5-dimethyl-1H-pyrazole-3-carboxamide

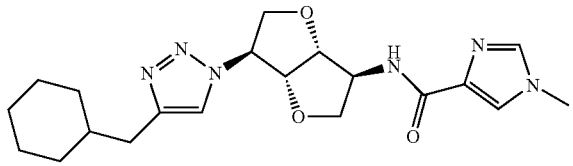 [SMILES: Cn1cnc(C(=O)N[C@H]2CO[C@H]3[C@@H]2OC[C@@H]3n2cc(CC3CCCCC3)nn2)c1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 1a) and 1,5-dimethyl-1H-pyrazole-3-carboxylic acid to provide N-((3S,3αR,6S,6αR)-6-(4-(cyclohexylmethyl)-1H-1,2,3-triazol-1-yl)-hexahydrofuro[3,2-b]furan-3-yl)-1,5-dimethyl-1H-pyrazole-3-carboxamide. MS 415 (MH$^+$).

Example 25

N-((3S,3αR,6S,6αR)-6-(4-isobutyl-1H-1,2,3-triazol-1-yl)-hexahydrofuro[3,2-b]furan-3-yl)cyclopropanecarboxamide

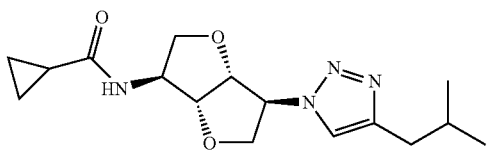 [SMILES: CC(C)Cc1cn([C@H]2CO[C@H]3[C@@H]2OC[C@@H]3NC(=O)C2CC2)nn1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 25a) and cyclopropanecarboxylic acid to provide N-((3S,3αR,6S,6αR)-6-(4-isobutyl-1H-1,2,3-triazol-1-yl)-hexahydrofuro[3,2-b]furan-3-yl)cyclopropanecarboxamide. MS 321 (MH$^+$).

Example 25a (3S,3αR,6S,6αR)-6-(4-isobutyl-1H-1,2,3-triazol-1-yl)-hexahydrofuro[3,2-b]furan-3-amine Prepared as in example 1a from 1-((3S,3αR,6S,6αR)-6-azido-hexahydrofuro[3,2-b]furan-3-yl)-4-isobutyl-1H-1,2,3-triazole (example 25b) to provide (3S,3αR,6S,6αR)-6-(4-isobutyl-1H-1,2,3-triazol-1-yl)-hexahydrofuro[3,2-b]furan-3-amine. MS 253 (MH$^+$).

Example 25b 1-((3S,3αR,6S,6αR)-6-azido-hexahydrofuro[3,2-b]furan-3-yl)-4-isobutyl-1H-1,2,3-triazole Prepared as in example 1b from (3S,3αR,6S,6αR)-3,6-diazido-hexahydrofuro[3,2-b]furan (example 1c) to provide 1-((3S,3αR,6S,6αR)-6-azido-hexahydrofuro[3,2-b]furan-3-yl)-4-isobutyl-1H-1,2,3-triazole.

Example 26

N-((3S,3αR,6S,6αR)-6-(4-(cyclopentylmethyl)-1H-1,2,3-triazol-1-yl)-hexahydrofuro[3,2-b]furan-3-yl)cyclopropanecarboxamide

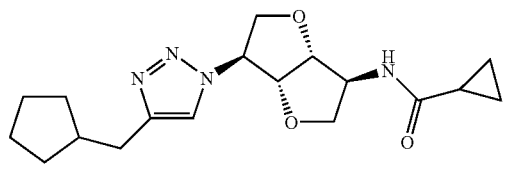 [SMILES: O=C(N[C@H]1CO[C@H]2[C@@H]1OC[C@@H]2n1cc(CC2CCCC2)nn1)C1CC1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 26a) and cyclopropanecarboxylic to provide N-((3S,3αR,6S,6αR)-6-(4-(cyclopentylmethyl)-1H-1,2,3-triazol-1-yl)-hexahydrofuro[3,2-b]furan-3-yl)cyclopropanecarboxamide. MS 347 (MH$^+$).

Example 26a (3S,3αR,6S,6αR)-6-(4-(cyclopentylmethyl)-1H-1,2,3-triazol-1-yl)-hexahydrofuro[3,2-b]furan-3-amine Prepared as in example 1a from 1-((3S,3αR,6S,6αR)-6-azido-hexahydrofuro[3,2-b]furan-3-yl)4-(cyclopentylmethyl)-1H-1,2,3-triazole (example 26b) to provide (3S,3αR,6S,6αR)-6-(4-(cyclopentylmethyl)-1H-1,2,3-triazol-1-yl)-hexahydrofuro[3,2-b]furan-3-amine. MS 253 (MH$^+$).

Example 26b 1-((3S,3αR,6S,6αR)-6-azido-hexahydrofuro[3,2-b]furan-3-yl)-4-(cyclopentylmethyl)-1H-1,2,3-triazole Prepared as in example 1b from (3S,3αR,6S,6αR)-3,6-diazido-hexahydrofuro[3,2-b]furan (example 1c) to provide 1-((3S,3αR,6S,6αR)-6-azido-hexahydrofuro[3,2-b]furan-3-yl)-4-(cyclopentylmethyl)-1H-1,2,3-triazole.

Example 27

N-((3S,3αR,6S,6αR)-6-(4-phenyl-1H-1,2,3-triazol-1-yl)-hexahydrofuro[3,2-b]furan-3-yl)cyclopropanecarboxamide

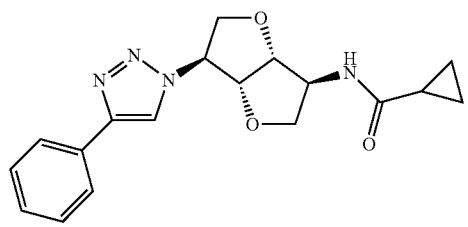 [SMILES: O=C(N[C@H]1CO[C@H]2[C@@H]1OC[C@@H]2n1cc(-c2ccccc2)nn1)C1CC1]

Prepared as in example 1 from (3S,3αR,6S,6αR)-6-(4-(cyclohexylmethyl)-1H-1,2,3-triazol-1-yl)-hexahydrofuro

[3,2-b]furan-3-amine (example 27a) and cyclopropanecarboxylic to provide N-((3S,3αR,6S,6αR)-6-(4-phenyl-1H-1,2,3-triazol-1-yl)-hexahydrofuro[3,2-b]furan-3-yl)cyclopropanecarboxamide. MS 341 (MH+).

Example 27a (3S,3αR,6S,6αR)-6-(4-phenyl-1H-1,2,3-triazol-1-yl)-hexahydrofuro-[3,2-b]furan-3-amine Prepared as in example 1a from 1-((3S,3αR,6S,6αR)-6-azido-hexahydrofuro[3,2-b]furan-3-yl)-4-phenyl-1H-1,2,3-triazole (example 27b) to provide (3S,3αR,6S,6αR)-6-(4-phenyl-1H-1,2,3-triazol-1-yl)-hexahydrofuro[3,2-b]furan-3-amine. MS 273 (MH+).

Example 27b 1-((3S,3αR,6S,6αR)-6-azido-hexahydrofuro[3,2-b]furan-3-yl)4-phenyl-1H-1,2,3-triazole Prepared as in example 1b from (3S,3αR,6S,6αR)-3,6-diazido-hexahydrofuro[3,2-b]furan (example 1c) to provide 1-((3S,3αR,6S,6αR)-6-azido-hexahydrofuro[3,2-b]furan-3-yl)-4-phenyl-1H-1,2,3-triazole.

Example 28

N-((3S,3αR,6S,6αR)-6-(4-benzyl-1H-1,2,3-triazol-1-yl)-hexahydrofuro[3,2-b]furan-3-yl)cyclopropanecarboxamide

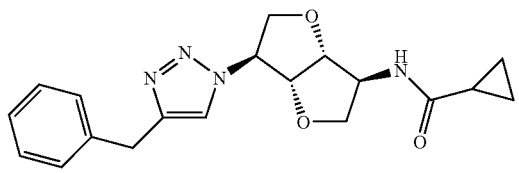 [SMILES: O=C(N[C@H]1CO[C@H]2[C@@H]1OC[C@@H]2n1cc(Cc2ccccc2)nn1)C1CC1]

Prepared as in example 1 from (3S,3αR,6S,6αR)-6-(4-(cyclohexylmethyl)-1H-1,2,3-triazol-1-yl)-hexahydrofuro[3,2-b]furan-3-amine (example 28a) and cyclopropanecarboxylic to provide N-((3S,3αR,6S,6αR)-6-(4-benzyl-1H-1,2,3-triazol-1-yl)-hexahydrofuro[3,2-b]furan-3-yl)cyclopropanecarboxamide. MS 355 (MH+).

Example 28a (3S,3αR,6S,6αR)-6-(4-benzyl-1H-1,2,3-triazol-1-yl)-hexahydrofuro[3,2-b]furan-3-amine Prepared as in example 1a from 1-((3S,3αR,6S,6αR)-6-azido-hexahydrofuro[3,2-b]furan-3-yl)-4-benzyl-1H-1,2,3-triazole (example 28b) to provide (3S,3αR,6S,6αR)-6-(4-benzyl-1H-1,2,3-triazol-1-yl)-hexahydrofuro[3,2-b]furan-3-amine. MS 287 (MH+).

Example 28b 1-((3S,3αR,6S,6αR)-6-azido-hexahydrofuro[3,2-b]furan-3-yl)-4-benzyl-1H-1,2,3-triazole Prepared as in example 1b from (3S,3αR,6S,6αR)-3,6-diazido-hexahydrofuro[3,2-b]furan (example 1c) to provide 1-((3S,3αR,6S,6αR)-6-azido-hexahydrofuro[3,2-b]furan-3-yl)-4-benzyl-1H-1,2,3-triazole.

Example 29

N-((3S,3αR,6S,6αR)-6-(4cyclohexylbutanamido)hexahydrofuro-[3,2-b]furan-3-yl)cyclopropanecarboxamide

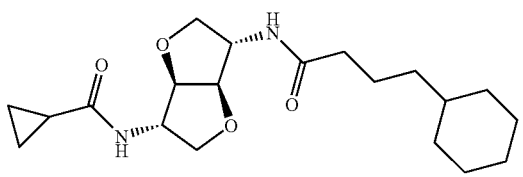 [SMILES: O=C(CCCC1CCCCC1)N[C@H]1CO[C@H]2[C@@H]1OC[C@@H]2NC(=O)C1CC1]

Prepared as in example 1 from 4-cyclohexylbutanoic acid and N-((3S,3αR,6S,6αR)-6-aminohexahydrofuro[3,2-b]furan-3-yl) (example 29a) to provide N-((3S,3αR,6S,6αR)-6-(4-cyclohexylbutanamido)hexahydrofuro[3,2-b]furan-3-yl)-cyclopropanecarboxamide (100 mg, 58.2%) as a white powder. $^1$H NMR (DMSO-d$_6$, 400 MHz): 0.66 (m,4H), 0.83 (m,2H),1.15 (m, 6H), 1.49 (m, 2H), 1.58 (m, 2H), 1.66 (m, 1H), 2.04 (t, 2H, J=7.2 Hz), 3.62 (ddd, 2H, J=15.2, 9.2, 2.0 Hz),3.84 (dd, 2H, J=9.2, 4.8 Hz), 4.11 (m, 2H), 4.38 (m, 2H), 8.07 (d, 1H, J=7.2 Hz), 8.37 (d, 1H, J=7.2 Hz). M+H=365, m.p=181.5-182.5° C.

Example 29a

N-((3S,3αR,6S,6αR)-6-aminohexahydrofuro[3,2-b]furan-3-yl)cyclo-propanecarboxamide Prepared as in example 1a from N-((3S,3αR,6S,6αR)-6-azidohexahydrofuro[3,2-b]furan-3-yl)cyclopropanecarboxamide (example 29b) to yield N-((3S,3αR,6S,6αR)-6-amino-hexahydrofuro[3,2-b]furan-3-yl)cyclopropanecarboxamide (1.06 g, quantitative) as pure product. M+H=213.

Example 29b

N-((3S,3αR,6S,6αR)-6-azidohexahydrofuro[3,2-b]furan-3-yl)cyclo-propanecarboxamide Prepared as in example 1 from cyclopropane carboxylic acid and (3S,3αR,6S,6αR)-6-azidohexahydrofuro[3,2-b]furan-3-amine (example 29c) to yield N-((3S,3αR,6S,6αR)-6-azidohexahydrofuro[3,2-b]furan-3-yl)cyclopropanecarboxamide (3.29 g, 69%). M+H=239

Example 29c (3S,3αR,6S,6αR)-6-azidohexahydrofuro[3,2-b]furan-3-amine

To a solution of (3S,3αR,6S,6αR)-3,6-diazidohexahydrofuro[3,2-b]furan (7.84 g, 40 mmol) (example 1c) in 50 mL EtOAc/Et$_2$O (1:1) and 40 mL 5% HCl solution in water, was added Ph$_3$P (10.5 g, 40 mmol) in small portions at 0° C. over 1 hour. The mixture was then stirred at room temperature overnight. The organic layer was discarded and the aqueous was washed 2× with methylene chloride. The aqueous was then carefully basified to pH 9 using a 1N NaOH solution. The solution was then extracted with methylene chloride 3× and dried over Na₂CO₃. The methylene chloride was evaporated to yield (4.1 g, 60.2%) of (3S,3αR,6S,6αR)-6-azidohexahydrofuro-[3,2-b]furan-3-amine as a yellowish liquid. M+H=171.

Example 30

N-((3S,3αR,6S,6αR)-6-(cyclopropanecaboxamido) hexahydrofuro-[3,2-b]furan-3-yl)-3-phenoxybenzamide

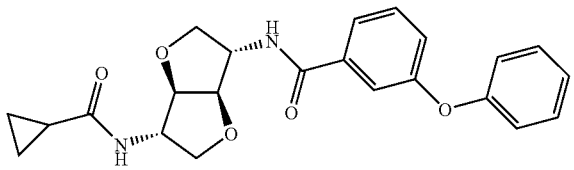 [SMILES: O=C(N[C@H]1CO[C@H]2[C@@H]1OC[C@@H]2NC(=O)C1CC1)c1cccc(Oc2ccccc2)c1]

Prepared as in example 1 from 3-phenoxybenzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-phenoxybenzamide (11 mg, 54.5%). M+H=409.

Example 31

N-((3S,3αR,6S,6αR)-6-(cyclopropanecaboxamido) hexahydrofuro-[3,2-b]furan-3-yl)-5,6,7,8-tetrahydronaphthalene-2-carboxamide

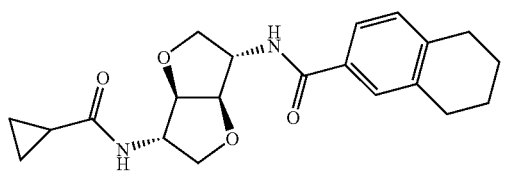 [SMILES: O=C(N[C@H]1CO[C@H]2[C@@H]1OC[C@@H]2NC(=O)C1CC1)c1ccc2c(c1)CCCC2]

Prepared as in example 1 from 5,6,7,8-tetrahydronaphthalene-2-carboxylic acid and N-((3S,3αR,6S,6αR)-6-aminohexahydrofuro[3,2-b]furan-3-yl) (example 29a) to yield N-((3S,3αR, 6S,6αR)-6-(cyclopropanecaboxamido)hexahydrofuro[3,2-b]furan-3-yl)-5,6,7,8-tetrahydronaphthalene-2-carboxamide (10 mg, 54.1%). M+H=371.

Example 32

N-((3S,3αR,6S,6αR)-6-(cyclopropanecarboxamido) hexahydrofuro-[3,2-b]furan-3-yl)-2-(thiophen-2-ylmethyl)benzamide

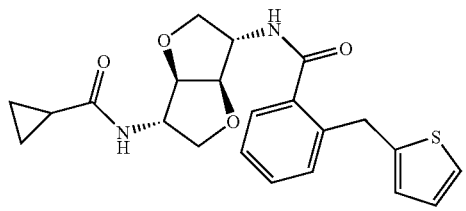 [SMILES: O=C(N[C@H]1CO[C@H]2[C@@H]1OC[C@@H]2NC(=O)C1CC1)c1ccccc1Cc1cccs1]

Prepared as in example 1 from 2-(thiophen-2-ylmethyl) benzoic acid and N-((3S,3αR,6S,6αR)-6-aminohexahydrofuro[3,2-b]furan-3-yl) (example 29a) to yield N-((3S, 3αR, 6S,6αR)-6-(cyclopropanecarboxamido)hexahydrofuro[3,2-b]furan-3-yl)-2-(thiophen-2-ylmethyl)benzamide (2.8 mg, 27%). M+H=413.

Example 33

5-tert-butyl-N-((3S,3αR,6S,6αR)-6-(cyclopropanecarboxamido)hexahydrofuro[3,2-b]furan-3-yl)-2-methylfuran-3-carboxamide

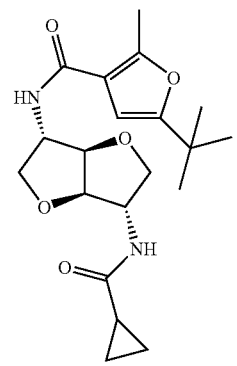 [SMILES: Cc1oc(C(C)(C)C)cc1C(=O)N[C@H]1CO[C@H]2[C@@H]1OC[C@@H]2NC(=O)C1CC1]

Prepared as in example 1 from 5-tert-butyl-2-methylfuran-3-carboxylic acid and N-((3S,3αR,6S,6αR)-6-aminohexahydrofuro[3,2-b]furan-3-yl) (example 29a) to yield 5-tert-butyl-N-((3S,3αR,6S,6αR)-6-(cyclopropanecarboxamido) hexahydrofuro-[3,2-b]furan-3-yl)-2-methylfuran-3-carboxamide (3.6 mg, 38.8%). M+H=377.

Example 34

4-tert-butyl-N-((3S,3αR,6S,6αR)-6-(cyclopropanecarboxamido)hexahydrofuro[3,2-b]furan-3-yl)cyclohexanecarboxamide

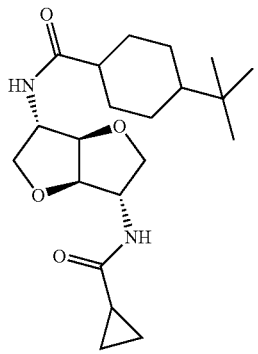 [SMILES: CC(C)(C)C1CCC(C(=O)N[C@H]2CO[C@H]3[C@@H]2OC[C@@H]3NC(=O)C2CC2)CC1]

Prepared as in example 1 from 4-tert-butylcyclohexanecarboxylic acid and N-((3S,3αR,6S,6αR)-6-aminohexahydrofuro[3,2-b]furan-3-yl) (example 29a) to yield 4-tert-butyl-N-((3S,3αR, 6S,6αR)-6-(cyclopropanecarboxamido) hexahydrofuro[3,2-b]furan-3-yl)cyclohexanecarboxamide (3.4 mg, 36.3%). M+H=379.

Example 35

N-((3S,3αR,6S,6αR)-6-(5-(4-fluorophenyl)pentanamido)hexahydro-furo[3,2-b]furan-3-yl)cyclopropanecarboxamide

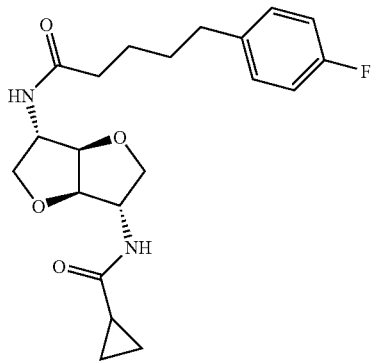 [SMILES: O=C(CCCCc1ccc(F)cc1)N[C@H]1CO[C@H]2[C@@H]1OC[C@@H]2NC(=O)C1CC1]

Prepared as in example 1 from 5-(4-fluorophenyl)pentanoic acid and N-((3S, 3αR, 6S, 6αR)-6-aminohexahydrofuro[3,2-b]furan-3-yl) (example 29a) to yield N-((3S, 3αR, 6S, 6αR)-6-(5-(4-fluorophenyl)pentanamido)hexahydrofuro[3,2-b]furan-3-yl)-cyclopropanecarboxamide (3.7 mg, 38%). M+H=391.

Example 36

N-((3S,3αR,6S,6αR)-6(cyclopropanecarboxamido)hexahydrofuro-[3,2-b]furan-3-yl)-1-(4-methoxyphenyl)cyclopentanecarboxamide

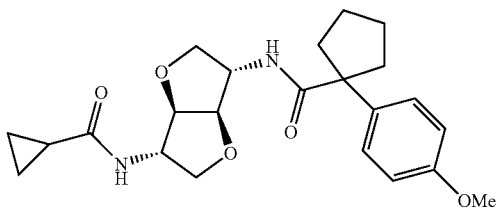 [SMILES: COc1ccc(C2(C(=O)N[C@H]3CO[C@H]4[C@@H]3OC[C@@H]4NC(=O)C3CC3)CCCC2)cc1]

Prepared as in example 1 from 1-(4-methoxyphenyl)cyclopentanecarboxylic acid and N-((3S,3αR,6S,6αR)-6-aminohexahydrofuro[3,2-b]furan-3-yl) (example 29a) to yield N-((3S, 3αR,6S,6αR)-6-(cyclopropanecarboxamido)hexahydrofuro[3,2-b]furan-3-yl)-1-(4-methoxyphenyl)cyclopentanecarboxamide (3.7 mg, 36%). M+H=415.

Example 37

N-((3S,3αR,6S,6αR)-6-(2-(2-(trimethylsilyl)ethylthio)acetamido)hexahydrofuro[3,2-b]furan-3-yl)cyclopropanecarboxamide

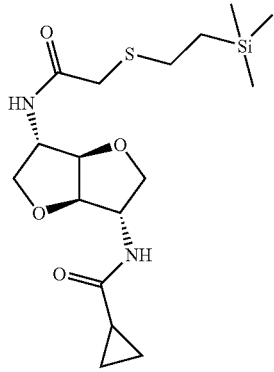 [SMILES: C[Si](C)(C)CCSCC(=O)N[C@H]1CO[C@H]2[C@@H]1OC[C@@H]2NC(=O)C1CC1]

Prepared as in example 1 from 2-(2-trimethylsilyl)ethylthio)acetic acid and N-((3S,3αR, 6S,6αR)-6-aminohexahydrofuro[3,2-b]furan-3-yl) (example 29a) to yield N-((3S, 3αR, 6S, 6αR)-6-(2-(2-(trimethylsilyl)ethylthio)acetamido)hexahydrofuro[3,2-b]furan-3-yl)cyclopropanecarboxamide (3.3 mg, 34.4%). M+H=387.

Example 38

N-((3S,3αR,6S,6αR)-6-(cyclopropanecarboxamido)hexahydrofuro-[3,2-b]furan-3-yl)4-phenylthiazole-2-carboxamide

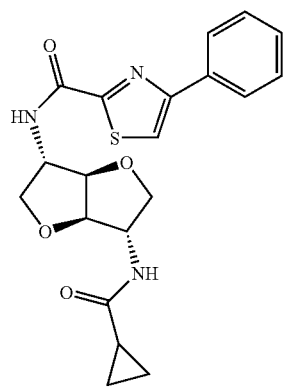 [SMILES: O=C(N[C@H]1CO[C@H]2[C@@H]1OC[C@@H]2NC(=O)C1CC1)c1nc(-c2ccccc2)cs1]

Prepared as in example 1 from 4-phenylthiazole-2-carboxylic acid and N-((3S,3αR,6S,6αR)-6-aminohexahydrofuro[3,2-b]furan-3-yl) (example 29a) to yield N-((3S,3αR, 6S,6αR)-6-(cyclopropanecarboxamido)hexahydrofuro[3,2-b]furan-3-yl)-4-phenylthiazole-2-carboxamide (4.0 mg, 40%). M+H=400.

Example 39

N-((3S,3αR,6S,6αR)-6-(cyclopropanecarboxamido)hexahydrofuro-[3,2-b]furan-3-yl)-1H-pyrrole-3-carboxamide

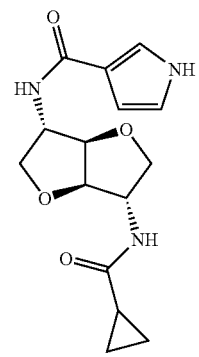 [SMILES: O=C(N[C@H]1CO[C@H]2[C@@H]1OC[C@@H]2NC(=O)C1CC1)c1cc[nH]c1]

Prepared as in example 1 from 1H-pyrrole-3-carboxylic acid and N-((3S,3αR,6S,6αR)-6-aminohexahydrofuro[3,2-b]furan-3-yl) (example 29a) to yield N-((3S,3αR,6S,6αR)-6-(cyclopropanecarboxamido)hexahydrofuro[3,2-b]furan-3-yl)-1H-pyrrole-3-carboxamide (3.0 mg, 39.5%). M+H=306.

Example 40

N-((3S,3αR,6S,6αR)-6-(2-(4-methylcyclohexyl)acetamido) hexahydro-furo-[3,2-b]furan-3-yl)cyclopropanecarboxamide

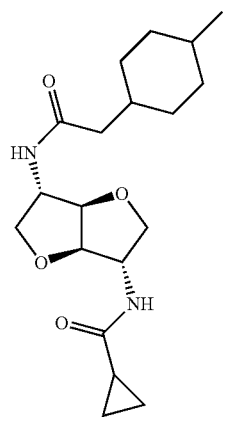 [SMILES: CC1CCC(CC(=O)N[C@H]2CO[C@H]3[C@@H]2OC[C@@H]3NC(=O)C2CC2)CC1]

Prepared as in example 1 from 2-(4-methylcyclohexyl)acetic acid and N-((3S,3αR,6S,6αR)-6-aminohexahydrofuro[3,2-b]furan-3-yl) (example 29a) to yield N-((3S, 3αR, 6S,6αR)-6-(2-(4-methylcyclohexyl)acetamido)hexahydrofuro[3,2-b]furan-3-yl)-cyclopropanecarboxamide (3.5 mg, 40%). M+H=351.

Example 41

N-((3S,3αR,6S,6αR)-6-(3-cyclopentylpropanamido)hexahydrofuro-[3,2-b]furan-3-yl)cyclopropanecarboxamide

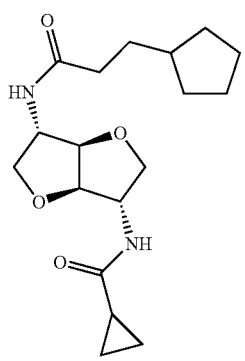 [SMILES: O=C(CCC1CCCC1)N[C@H]1CO[C@H]2[C@@H]1OC[C@@H]2NC(=O)C1CC1]

Prepared as in example 1 from 3-cyclopentylpropanoic acid and N-((3S,3αR,6S,6αR)-6-aminohexahydrofuro[3,2-b]furan-3-yl) (example 29a) to yield N-((3S,3αR,6S,6αR)-6-(3-cyclopentylpropanamido)hexahydrofuro[3,2-b]furan-3-yl)cyclopropanecarboxamide (4.3 mg, 51.2%). M+H=337.

Example 42

(1S,4S4-butyl-N-((3S,3αR,6S,6αR)-6-(cyclopropanecarboxamido)hexahydrofuro[3,2-b]furan-3-yl)cyclohexanecarboxamide

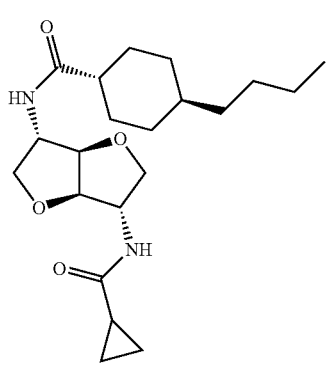 [SMILES: CCCC[C@H]1CC[C@H](C(=O)N[C@H]2CO[C@H]3[C@@H]2OC[C@@H]3NC(=O)C2CC2)CC1]

Prepared as in example 1 from (1s,4r)-4-butylcyclohexanecarboxylic acid and N-((3S,3αR,6S,6αR)-6-aminohexahydrofuro[3,2-b]furan-3-yl) (example 29a) to yield (1s,4S)-4-butyl-N-((3S,3αR, 6S, 6αR)-6-(cyclopropanecarboxamido)hexahydrofuro-[3,2-b]furan-3-yl)cyclohexanecarboxamide (3.8 mg, 40%). M+H=379.

Example 43

N-((3S,3αR,6S,6αR)-6-(cyclopropanecaboxamido)hexahydrofuro[3,2-b]furan-3-yl)-2-(m-tolyloxy)benzamide

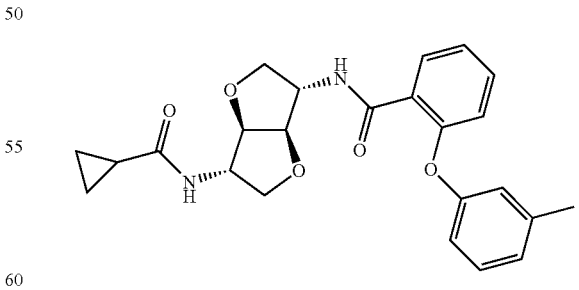

Prepared as in example 1 from 2-(m-tolyloxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-2-(m-tolyloxy)benzamide (11 mg, 74.1%). M+H=423.

Example 44

N-((3S,3αR,6S,6αR)-6-(cyclopropanecaboxamido)hexahydrofuro[3,2-b]furan-3-yl)-2-phenoxybenzamide

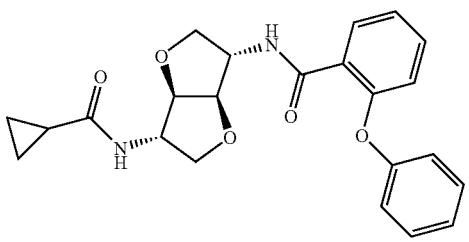 [SMILES: O=C(N[C@H]1CO[C@H]2[C@@H]1OC[C@@H]2NC(=O)C1CC1)c1ccccc1Oc1ccccc1]

Prepared as in example 1 from 2-phenoxybenzoic acid and N-((35,3αR,6S,6αR)-6-aminohexahydrofuro[3,2-b]furan-3-yl) (example 29a) to yield N-((3S, 3αR, 6S, 6αR)-6-(cyclopropanecaboxamido)hexahydrofuro[3,2-b]furan-3-yl)-2-phenoxybenzamide (10.7 mg, 75.5%). M+H=409.

Example 45

N-((3S,3αR,6S,6αR)-6-(cyclopropanecaboxamido)hexahydrofuro[3,2-b]furan-3-yl)-2-(phenylamino)benzamide

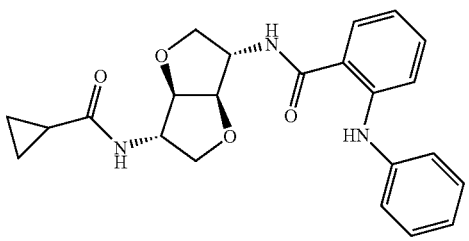 [SMILES: O=C(N[C@H]1CO[C@H]2[C@@H]1OC[C@@H]2NC(=O)C1CC1)c1ccccc1Nc1ccccc1]

Prepared as in example 1 from 2-(phenylamino)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-2-(phenylamino)benzamide (10.1 mg, 70.9%). $^1$H NMR (DMSO-$d_6$, 400 MHz): 0.66 (m, 4H), 1.57 (m, 1H), 3.66 (m, 1H,), 3.77 (dd, 2H, J=9.6, 2.8 Hz), 3.88 (dd, 2H, J=9.6, 4.8 Hz), 3.95 (dd, 2H, J=9.6, 5.6 Hz), 4.14 (m, 1H), 4.31 (m, 1H), 4.45 (d, 1H, J=3.6 Hz), 4.58 (d, 1H, J=4.0 Hz), 6.84 (m, 1H), 6.97 (m, 1H), 7.14 (m, 2H), 7.26-7.36 (m, 4H), 7.68 (dd, 2H, J=8.0, 5.2 Hz), 8.37 (d, 1H, J=7.2 Hz), 8.67 (d, 1H, J=6.8 Hz), 9.46 (s, 1H). M+H=408.

Example 46

2-benzyl-N-((3S,3αR,6S,6αR)-6-(cyclopropanecaboxamido)hexahydrofuro[3,2-b]furan-3-yl)benzamide

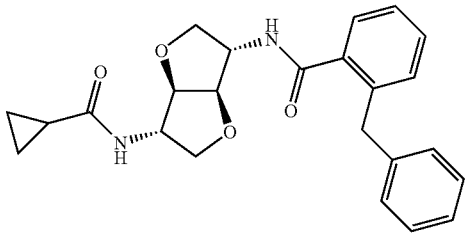 [SMILES: O=C(N[C@H]1CO[C@H]2[C@@H]1OC[C@@H]2NC(=O)C1CC1)c1ccccc1Cc1ccccc1]

Prepared as in example 1 from 2-benzylbenzoic acid and N-((3S,3αR,6S,6αR)-6-aminohexahydrofuro[3,2-b]furan-3-yl) (example 29a) to yield 2-benzyl-N-((3S,3αR,6S,6αR)-6-(cyclopropanecaboxamido)hexahydrofuro[3,2-b]furan-3-yl)benzamide (7 mg, 68.8%). M+H=407.

Example 47

N-((3S,3αR,6S,6αR)-6-(cyclopropanecaboxamido)hexahydrofuro[3,2-b]furan-3-yl)-2-(4-methoxyphenoxy)benzamide

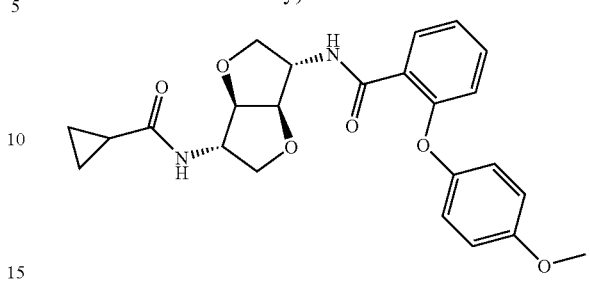

Prepared as in example 1 from 2-(4-methoxyphenoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-2-(4-methoxyphenoxy)benzamide (11.6 mg, 75.7%). $^1$H NMR (DMSO-$d_6$, 400 MHz): 0.65 (m, 4H), 1.56 (m, 1H), 3.64 (m, 1H,), 3.74 (s, 1H), 3.87 (m, 2H), 4.10 (m, 1H), 4.27 (m, 1H), 4.36 (d, 1H, J=8.0 Hz), 4.49 (d, 1H, J=4.0 Hz), 4.49 (d, 1H, J=4.0 Hz), 6.80 (dd, 2H, J=8.0, 0.8 Hz), 6.93-7.03 (m, 4H), 7.15 (m, 1H), 7.40 (m, 1H), 7.57 (dd, 2H, J=7.6, 1.6 Hz), 8.35 (d, 1H, J=7.2 Hz), 8.46 (d, 1H, J=6.8 Hz). M+H=439.

Example 48

N-((3S,3αR,6S,6αR)-6-(cyclopropanecaboxamido)hexahydrofuro[3,2-b]furan-3-yl)-2-(o-tolyloxy)benzamide

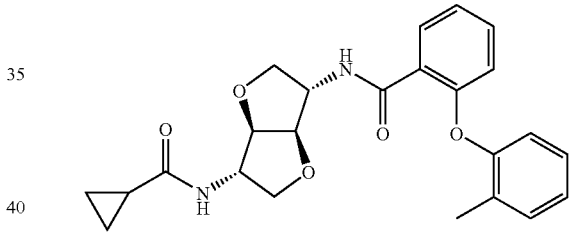

Prepared as in example 1 from 2-(o-tolyloxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-2-(o-tolyloxy)benzamide (8.8 mg, 83.2%). M+H=423.

Example 49

N-((3S,3αR,6S,6αR)-6-(cyclopropanecaboxamido)hexahydrofuro[3,2-b]furan-3-yl)-2-(3-methoxyphenoxy)benzamide

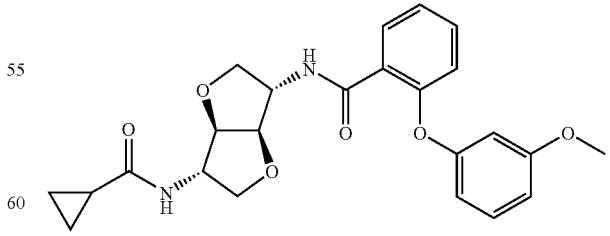

Prepared as in example 1 from 2-(3-methoxyphenoxy)benzoic acid and N-((3S,3αR,6S,6αR)-6-aminohexahydrofuro[3,2-b]furan-3-yl) (example 29a) to yield N-((3S, 3αR, 6S, 6αR)-6-(cyclopropanecaboxamido)hexahydrofuro[3,2-b]furan-3-yl)-2-(3-methoxyphenoxy)benzamide (10.6 mg, 69.3%). M+H=439.

Example 50

N-((3S,3αR,6S,6αR)-6-(cyclopropanecaboxamido)hexahydrofuro[3,2-b]furan-3-yl)-2-(3-fluorophenoxy)benzamide

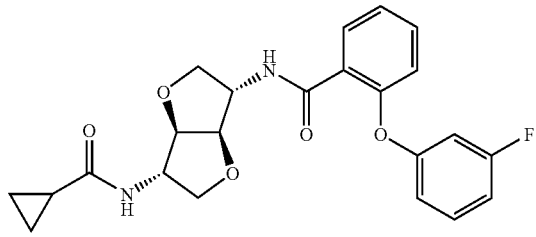 [SMILES: O=C(N[C@H]1CO[C@H]2[C@@H]1OC[C@@H]2NC(=O)C1CC1)c1ccccc1Oc1cccc(F)c1]

Prepared as in example 1 from 2-(3-fluorophenoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-2-(3-fluorophenoxy)benzamide (8.9 mg, 60%). M+H=427.

Example 51

N-((3S,3αR,6S,6αR)-6-(cyclopropanecaboxamido)hexahydrofuro[3,2-b]furan-3-yl)-2-(4-fluorophenoxy)benzamide

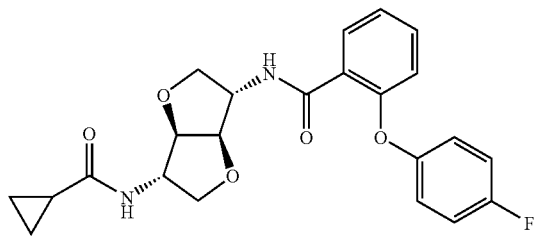 [SMILES: O=C(N[C@H]1CO[C@H]2[C@@H]1OC[C@@H]2NC(=O)C1CC1)c1ccccc1Oc1ccc(F)cc1]

Prepared as in example 1 from 2-(4-fluorophenoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-y)-2-(4-fluorophenoxy)benzamide (8 mg, 75.6%). M+H=427.

Example 52

N-((3S,3αR,6S,6αR)-6-(cyclopropanecaboxamido)hexahydrofuro[3,2-b]furan-3-yl)-2,3,4,5,6-pentamethylbenzamide

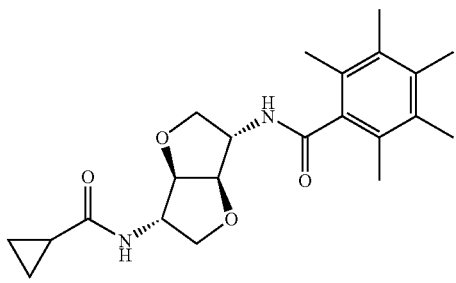 [SMILES: Cc1c(C)c(C)c(C(=O)N[C@H]2CO[C@H]3[C@@H]2OC[C@@H]3NC(=O)C2CC2)c(C)c1C]

Prepared as in example 1 from 2,3,4,5,6-pentamethylbenzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-2,3,4,5,6-pentamethylbenzamide (9.6 mg, 70.9%). M+H=387.

Example 53

N-((3S,3αR,6S,6αR)-6-(cyclopropanecaboxamido)hexahydrofuro[3,2-b]furan-3-yl)4-phenoxybenzamide

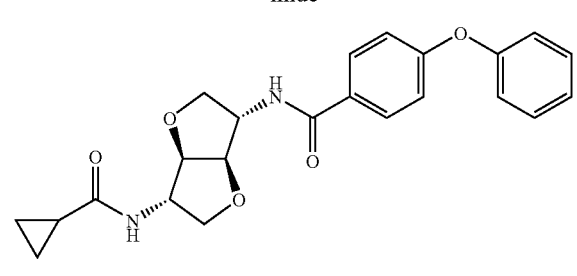

Prepared as in example 1 from 4-phenoxybenzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-4-phenoxybenzamide (8.1 mg, 56.6%). M+H=409.

Example 54

N-((3S,3αR,6S,6αR)-6-(cyclopropanecaboxamido)hexahydrofuro[3,2-b]furan-3-yl)4-pentybenzamide

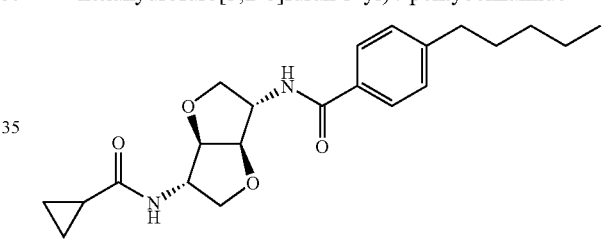

Prepared as in example 1 from 4-pentylbenzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-4-pentybenzamide (4.3 mg, 44.6%). M+H=387.

Example 55

3-chloro-N-((3S,3αR,6S,6αR)-6-(cyclopropanecaboxamido)hexahydrofuro[3,2-b]furan-3-yl)benzamide

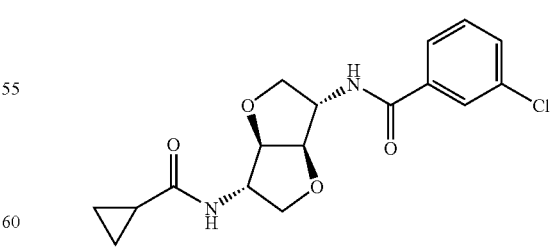

Prepared as in example 1 from 3-chlorobenzoic acid and N-((3S,3αR,6S,6αR)-6-aminohexahydrofuro[3,2-b]furan-3-yl) (example 29a) to yield 3-chloro-N-((3S,3αR,6S,6αR)-6-(cyclopropanecaboxamido)hexahydrofuro[3,2-b]furan-3-yl)benzamide (4.0 mg, 45.3%). M+H=351.

Example 56

N-((3S,3αR,6S,6αR)-6-(cyclopropanecaboxamido)hexahydrofuro[3,2-b]furan-3-yl)-4-(trifluoromethoxy)benzamide

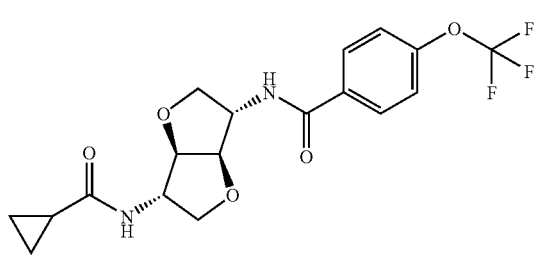 [SMILES: O=C(N[C@H]1CO[C@H]2[C@@H]1OC[C@@H]2NC(=O)C1CC1)c1ccc(OC(F)(F)F)cc1]

Prepared as in example 1 from 4-(trifluoromethoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-4-(trifluoromethoxy)benzamide (4.0 mg, 40%). M+H=401.

Example 57

N-((3S,3αR,6S,6αR)-6-(cyclopropanecaboxamido)hexahydrofuro[3,2-b]furan-3-yl)picolinamide

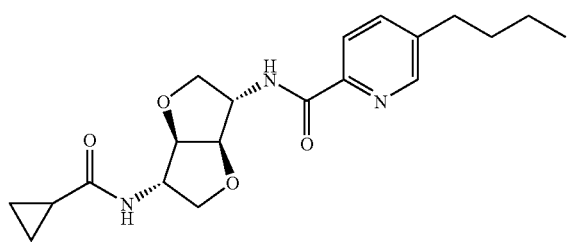 [SMILES: CCCCc1ccc(C(=O)N[C@H]2CO[C@H]3[C@@H]2OC[C@@H]3NC(=O)C2CC2)nc1]

Prepared as in example 1 from 5-butylpicolinic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)picolinamide (4.5 mg, 47.8%). M+H=374.

Example 58

N-((3S,3αR,6S,6αR)-6-(3,7-dimethyloct-6-enamido)hexahydrofuro[3,2-b]furan-3-yl)cyclopropanecarboxamide

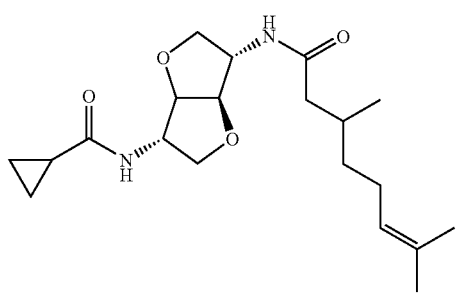

Prepared as in example 1 from 3,7-dimethyloct-6-enoic acid and N-((3S,3αR,6S,6αR)-6-aminohexahydrofuro[3,2-b]furan-3-yl) (example 29a) to yield N-((3S,3αR,6S,6αR)-6-(3,7-dimethyloct-6-enamido)hexahydrofuro[3,2-b]furan-3-yl)cyclopropanecarboxamide (3.6 mg, 39%). M+H=365.

Example 59

N-((3S,3αR,6S,6αR)-6-undec-10-ynamidohexahydrofuro[3,2-b]furan-3-yl)cyclopropanecarboxamide

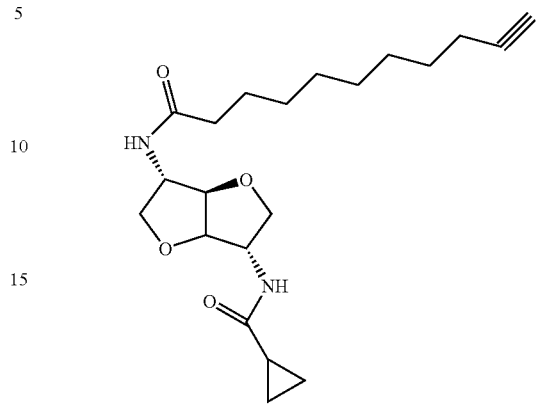

Prepared as in example 1 from undec-10-ynoic acid and N-((3S,3αR,6S,6αR)-6-aminohexahydrofuro[3,2-b]furan-3-yl) (example 29a) to yield N-((3S,3αR,6S,6αR)-6-undec-10-ynamidohexahydrofuro[3,2-b]furan-3-yl)cyclopropanecarboxamide (2.4 mg, 25.9%). M+H=377.

Example 60

N-((3S,3αR,6S,6αR)-6-(cyclopropanecarboxamido)hexahydrofuro[3,2-b]furan-3-yl)4-pentylcyclohexanecarboxamide

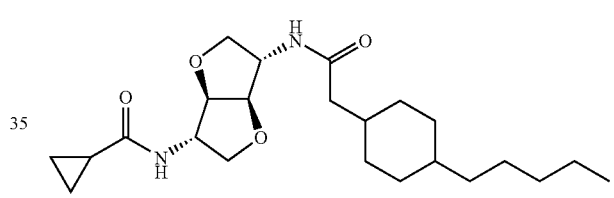

Prepared as in example 1 from 4-pentylcyclohexanecarboxylic acid and N-((3S,3αR,6S,6αR)-6-aminohexahydrofuro[3,2-b]furan-3-yl) (example 29a) to yield N-((3S,3αR,6S,6αR)-6-(cyclopropanecarboxamido)hexahydrofuro[3,2-b]furan-3-yl)-4-pentylcyclohexanecarboxamide (3.3 mg, 33.7%). M+H=393.

Example 61

N-((3S,3αR,6S,6αR)-6-(5-cyclohexylpentamido)hexahydrofuro[3,2-b]furan-3-yl)cyclopropanecarboxamide

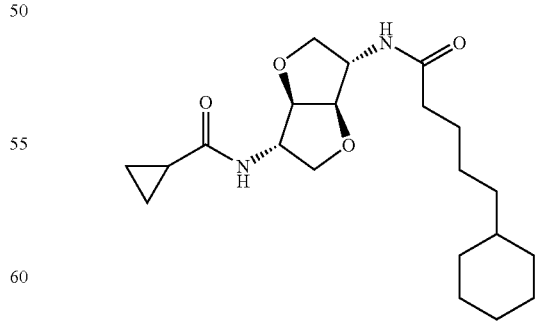

Prepared as in example 1 from 5-cyclohexylpentanoic acid and N-((3S,3αR,6S,6αR)-6-aminohexahydrofuro[3,2-b]furan-3-yl) (example 29a) to yield N-((3S,3αR,6S,6αR)-6-(5-cyclohexylpentamido)hexahydrofuro[3,2-b]furan-3-yl)cyclopropanecarboxamide (5.0 mg, 53.2%). M+H=379.

Example 62

N-((3S,3αR,6S,6αR)-6-(3-phenylpropiolamido)hexahydrofuro[3,2-b]furan-3-yl)cyclopropanecarboxamide

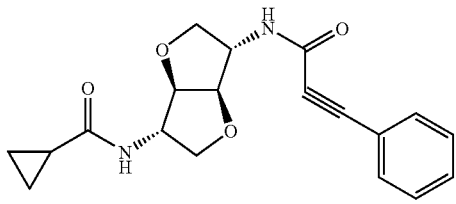 [SMILES: O=C(C#Cc1ccccc1)N[C@H]1CO[C@H]2[C@@H]1OC[C@@H]2NC(=O)C1CC1]

Prepared as in example 1 from 3-phenylpropiolic acid and N-((3S,3αR,6S,6αR)-6-aminohexahydrofuro[3,2-b]furan-3-yl) (example 29a) to yield N-((3S,3αR,6S,6αR)-6-(3-phenylpropiolamido)hexahydrofuro[3,2-b]furan-3-yl)cyclopropanecarboxamide (6.8 mg, 81%). M+H=341.

Example 63

N-((3S,3αR,6S,6αR)-6-(cyclopropanecarboxamido)hexahydrofuro[3,2-b]furan-3-yl)-3-methyl-1H-indene-2-carboxamide

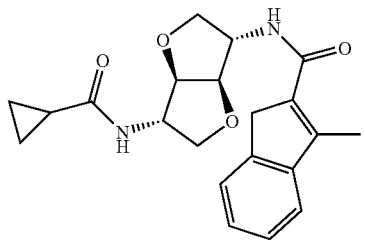 [SMILES: CC1=C(C(=O)N[C@H]2CO[C@H]3[C@@H]2OC[C@@H]3NC(=O)C2CC2)Cc2ccccc21]

Prepared as in example 1 from 3-methyl-1H-indene-2-carboxylic acid and N-((3S,3αR,6S,6αR)-6-aminohexahydrofuro[3,2-b]furan-3-yl) (example 29a) to yield N-((3S,3αR, 6S,6αR)-6-(cyclopropanecarboxamido)hexahydrofuro[3,2-b]furan-3-yl)-3-methyl-1H-indene-2-carboxamide (4.7 mg, 51.5%). M+H=369.

Example 64

N-((3S,3αR,6S,6αR)-6-(cyclopropanecarboxamido)hexahydrofuro[3,2-b]furan-3-yl)-5-methyl-1-phenyl-1H-pyrazole-4-carboxamide

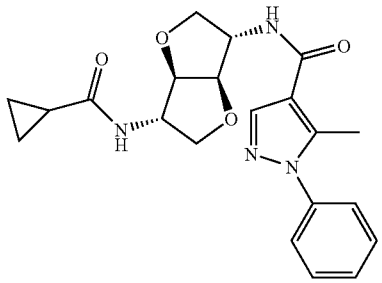 [SMILES: Cc1c(C(=O)N[C@H]2CO[C@H]3[C@@H]2OC[C@@H]3NC(=O)C2CC2)cnn1-c1ccccc1]

Prepared as in example 1 from 5-methyl-1-phenyl-1H-pyrazole-4-carboxylic acid and N-((3S,3αR,6S,6αR)-6-aminohexahydrofuro[3,2-b]furan-3-yl) (example 29a) to yield N-((3S,3αR,6S,6αR)-6-(cyclopropanecarboxamido)hexahydrofuro[3,2-b]furan-3-yl)-5-methyl-1-phenyl-1H-pyrazole-4-carboxamide (4.4 mg, 44.4%). M+H=397.

Example 65

N-((3S,3αR,6S,6αR)-6-((E)-4-phenylbut-3-enamido)hexahydrofuro[3,2-b]furan-3-yl)cyclopropanecarboxamide

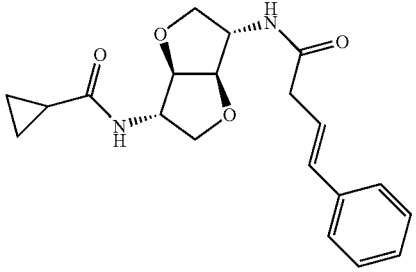 [SMILES: O=C(C/C=C/c1ccccc1)N[C@H]1CO[C@H]2[C@@H]1OC[C@@H]2NC(=O)C1CC1]

Prepared as in example 1 from (E)-4-phenylbut-3-enoic acid and N-((3S,3αR,6S,6αR)-6-aminohexahydrofuro[3,2-b]furan-3-yl) (example 29a) to yield N-((3S,3αR,6S,6αR)-6-((E)-4-phenylbut-3-enamido)hexahydrofuro[3,2-b]furan-3-yl)cyclopropanecarboxamide (4.0 mg, 44.5%). M+H=357.

Example 66

N-((3S,3αR,6S,6αR)-6-(cyclopropanecaboxamido)hexahydrofuro[3,2-b]furan-3-yl)-3-(o-tolyloxy)benzamide

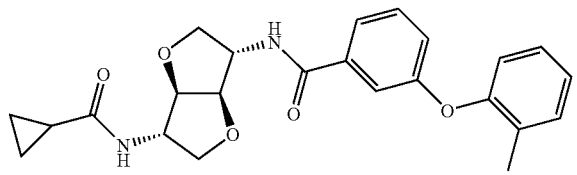 [SMILES: Cc1ccccc1Oc1cccc(C(=O)N[C@H]2CO[C@H]3[C@@H]2OC[C@@H]3NC(=O)C2CC2)c1]

Prepared as in example 1 from 3-(o-tolyloxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(o-tolyloxy)benzamide (7.0 mg, 47.1%). M+H=423.

Example 67

N-((3S,3αR,6S,6αR)-6-(cyclopropanecaboxamido)hexahydrofuro[3,2-b]furan-3-yl)-3-(m-tolyloxy)benzamide

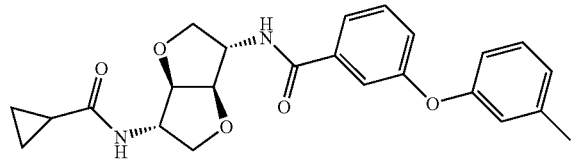 [SMILES: Cc1cccc(Oc2cccc(C(=O)N[C@H]3CO[C@H]4[C@@H]3OC[C@@H]4NC(=O)C3CC3)c2)c1]

Prepared as in example 1 from 3-(m-tolyloxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(m-tolyloxy)benzamide (6.6 mg, 44.4%). M+H=423.

Example 68

N-((3S,3αR,6S,6αR)-6-(cyclopropanecaboxamido)hexahydrofuro[13,2-b]furan-3-yl)-3-(p-tolyloxy)benzamide

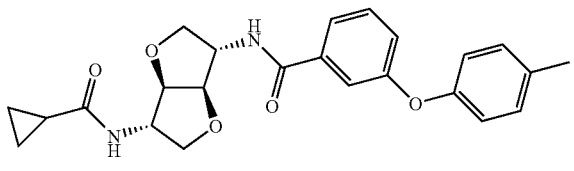 [SMILES: Cc1ccc(Oc2cccc(C(=O)N[C@H]3CO[C@H]4[C@@H]3OC[C@@H]4NC(=O)C3CC3)c2)cc1]

Prepared as in example 1 from 3-(p-tolyloxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(p-tolyloxy)benzamide (5.8 mg, 39.0%). M+H=423.

Example 69

N-((3S,3αR,6S,6αR)-6-(cyclopropanecaboxamido)hexahydrofuro[3,2-b]furan-3-yl)-3-(2-methoxyphenoxy)benzamide

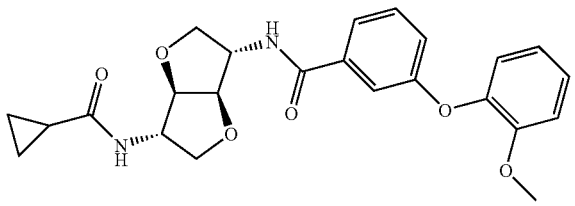 [SMILES: COc1ccccc1Oc1cccc(C(=O)N[C@H]2CO[C@H]3[C@@H]2OC[C@@H]3NC(=O)C2CC2)c1]

Prepared as in example 1 from 3-(2-methoxyphenoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(2-methoxyphenoxy)benzamide (6.0 mg, 39.4%). M+H=439.

Example 70

N-((3S,3αR,6S,6αR)-6-(cyclopropanecaboxamido)hexahydrofuro[3,2-b]furan-3-yl)-3-(3-methoxyphenoxy)benzamide

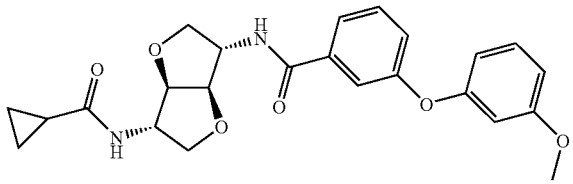 [SMILES: COc1cccc(Oc2cccc(C(=O)N[C@H]3CO[C@H]4[C@@H]3OC[C@@H]4NC(=O)C3CC3)c2)c1]

Prepared as in example 1 from 3-(3-methoxyphenoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(3-methoxyphenoxy)benzamide (6.1 mg, 40.0%). M+H=439.

Example 71

N-((3S,3αR,6S,6αR)-6-(cyclopropanecaboxamido)hexahydrofuro[3,2-b]furan-3-yl)-3-(4-methoxyphenoxy)benzamide

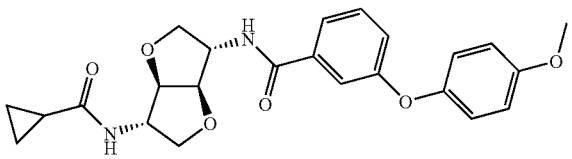 [SMILES: COc1ccc(Oc2cccc(C(=O)N[C@H]3CO[C@H]4[C@@H]3OC[C@@H]4NC(=O)C3CC3)c2)cc1]

Prepared as in example 1 from 3-(4-methoxyphenoxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(4-methoxyphenoxy)benzamide (6.8 mg, 44.6%). M+H=439.

Example 72

N-((3S,3αR,6S,6αR)-6-(cyclopropanecaboxamido)hexahydrofuro[3,2-b]furan-3-yl)-3-(pyridin-3-yloxy)benzamide

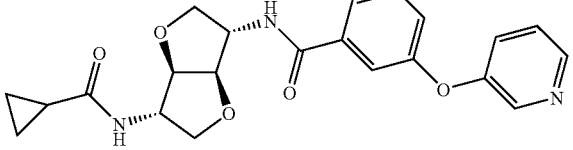

Prepared as in example 1 from 3-(pyridin-3-yloxy)benzoic acid and N-((3S,3αR,6S,6αR)-6-aminohexahydrofuro[3,2-b]furan-3-yl) (example 29a) to yield N-((3S,3αR,6S,6αR)-6-(cyclopropanecaboxamido)hexahydrofuro[3,2-b]furan-3-yl)-3-(pyridin-3-yloxy)benzamide (6.8 mg, 47.3%). M+H=410.

We claim:
1. A compound having structural formula (I)

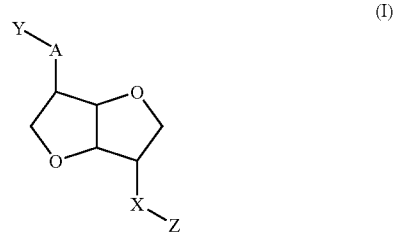

or the salt, solvate, ester, or N-oxide thereof, wherein:
A is aryl, or heteroaryl, selected from the group consisting of pyridinyl, pyrimidinyl, pyrazinyl, pyridazinyl, pyrrolyl, furanyl, thiofuranyl, oxazoloyl, isoxazoloyl, thiazolyl, and triazole;

Y is hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heterocyclyl, substituted heterocyclyl, heteroarylalkyl, substituted heteroarylalkyl, heterocyclylalkyl, substituted heterocyclylalkyl, carbocyclyl, substituted carbocyclyl, acyl, halo, —CN, —NO$_2$, —OR$^1$, —S(O)R$^1$, —S(O)$_2$R$^1$, —OC(O)R$^1$, —N(R$^1$)C(O)R$^2$, —NR$^1$R$^2$, —C(O)NR$^1$R$^2$, —C(O)OR$^1$, —S(O)$_2$NR$^1$R$^2$, —COR$^1$, —N(R$^1$)S(O)$_2$R$^2$, —SR$^1$, —C(R$^1$R$^2$R$^6$), —C(S)—R$^1$, —C(=NR$^2$)—R$^1$, —N(R$^1$)—C(=N—OR$^2$)R$^6$, —N(R$^1$)C(S)NR$^2$R$^6$, —C(=N—OR$^1$)R$^2$, —C(=NR$^1$)—NR$^2$R$^6$, —N(R$^1$)C(=NR$^2$)NR$^6$R$^7$, —N(R$^1$)C(S)R$^2$, —N(R$^1$)—C(O)—C(O)R$^2$, —C(S)—NR$^1$R$^2$, —N(R$^1$)C(=NR$^2$)OR$^6$, —C(=NR$^1$)O—NR$^2$R$^6$, —N(R$^1$)N(R$^2$)C(O)OR$^6$, —N(R$^1$)C(O)OR$^2$, —N(R$^1$)C(O)NR$^2$R$^6$, —N(R$^1$)—C(O)—C(O)—NR$^2$R$^6$, —C(O)—C(O)—NR$^1$R$^2$, —P(O)(OR$^1$)(OR$^2$), —P(O)(OR$^1$)(R$^2$), or —P(O)R$^1$R$^2$;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —C(=N—OR$^3$)—, —C(=NR$^3$)—NR$^4$—, —N(R$^3$)C(S)N(R$^4$)—R$^5$, —N(R$^3$)C(O)N(R$^4$)—R$^5$, —N(R$^3$)C(=NR$^4$)—, —N(R$^3$)C(S)—, —N(R$^3$)—C(O)—C(O)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)—C(=NR$^4$)—N(R$^5$)—, —N(R$^3$)N(R$^4$)C(O)O—, —N(R$^3$)C(O)O—, —N(R$^3$)C(O)N(R$^4$)—, —N(R$^3$)—C(O)—C(O)—NR$^4$—, —C(O)—C(O)—NR$^4$—, —P(O)(OR$^3$)—, or —P(O)R$^3$—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl; and R$^1$, R$^2$, R$^3$, R$^4$, R$^5$, R$^6$, and R$^7$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; and with the following proviso:
when A is triazole; then —X—Z is not —O-alkyl, —O-acyl, or sulfonamide.

2. The compound of claim 1, wherein Y is alkyl, substituted alkyl, aryl, substituted aryl, arylalkyl, substituted arylalkyl, carbocyclyl, or substituted carbocyclyl.

3. The compound of claim 1, wherein:
A is monocyclic five-membered heteroaryl selected from the group consisting of pyrrolyl, furanyl, thiofuranyl, oxazoloyl, isoxazolyl, thiazolyl, and triazole;
Y is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heterocyclyl, substituted heterocyclyl, carbocyclyl, substituted carbocyclyl, heteroarylalkyl, or substituted heteroarylalkyl;

X is —O—, —S—, —S(O)—, —S(O)$_2$—, —C(R$^3$R$^4$)—, —C(O)—, —C(S)—, —C(=NR$^3$)—, —C(O)O—, —N(R$^3$)—, —OC(O)—, —N(R$^3$)C(O)—, —C(O)N(R$^3$)—, —C(=N—OR$^3$)—, —C(=NR$^3$)—NR$^4$—, —N(R$^3$)C(=NR$^4$)—, —N(R$^3$)C(S)—, —C(S)—N(R$^3$)—, —N(R$^3$)S(O)$_2$—, —S(O)$_2$—N(R$^3$)—, —N(R$^3$)C(=NR$^4$)O—, —C(=NR$^4$)O—N(R$^3$)—, —N(R$^3$)C(=NR$^4$)—N(R$^5$)—, —N(R$^3$)N(R$^4$)C(O)O—, —N(R$^3$)C(O)O—, —N(R$^3$)C(O)N(R$^4$)—, —NR$^3$—C(O)—C(O)—NR$^4$—, —C(O)—C(O)—NR$^4$—, —P(O)(OR$^3$)—, or —P(O)(R$^3$)—;

Z is alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl; and R$^3$, R$^4$, and R$^5$ are each independently hydrogen, alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, carbocyclyl, or substituted carbocyclyl.

4. A compound having structural formula (Ia):

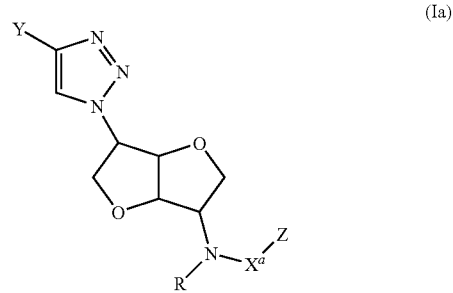

(Ia)

or the salt, solvate, ester, or N-oxide thereof, wherein
X$^a$ is —S(O)—, —S(O)$_2$—, —C(R$^3$R$^4$)—, —C(O)—, —C(O)O—, —C(O)N(R$^3$)—, —C(=N—OR$^3$)—, —C(=NR$^3$)—NR$^4$—, —C(=NR$^3$)—, —C(S)—N(R$^3$)—, —C(S)—, —NR$^3$—C(O)—C(O)—NR$^4$—, —C(O)—C(O)—NR$^4$—, or —S(O)$_2$—N(R$^3$)—;

Y is alkyl, substituted alkyl, aryl, substituted aryl, arylalkyl, substituted arylalkyl, carbocyclyl, or substituted carbocyclyl;

Z is alkyl, substituted alkyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, heteroarylalkyl, substituted heteroarylalkyl, heterocyclylalkyl, substituted heterocyclylalkyl, carbocyclyl, or substituted carbocyclyl; and R hydrogen, alkyl, or substituted alkyl.

5. A compound having a structural formula selected from the group consisting of

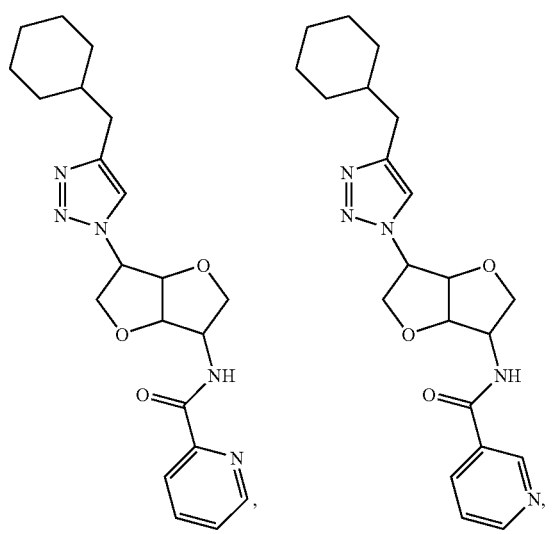
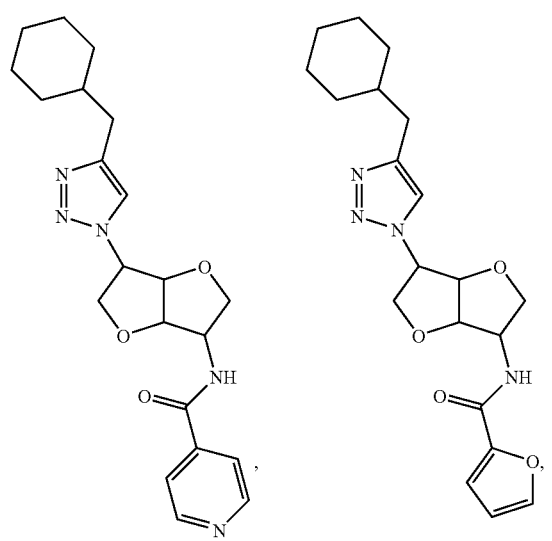
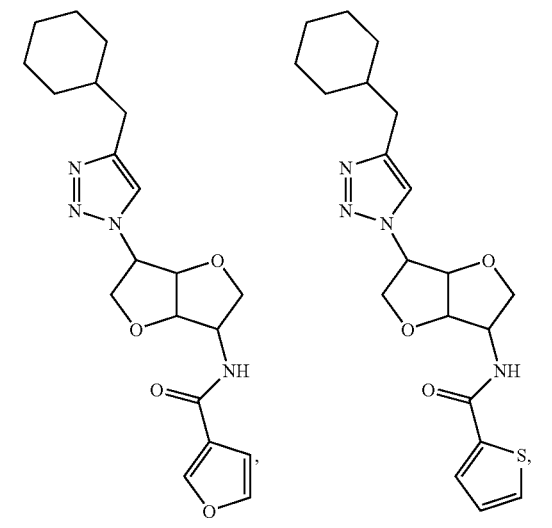
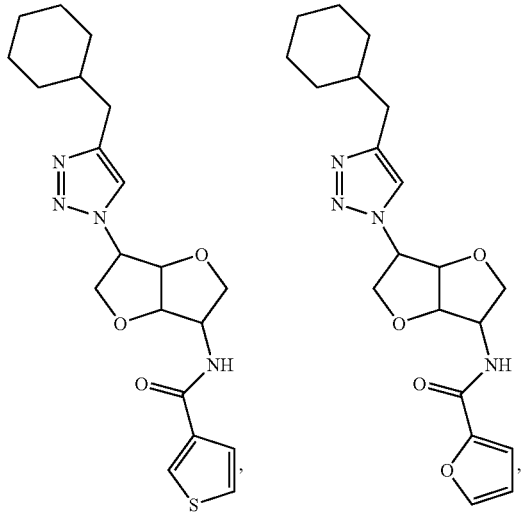
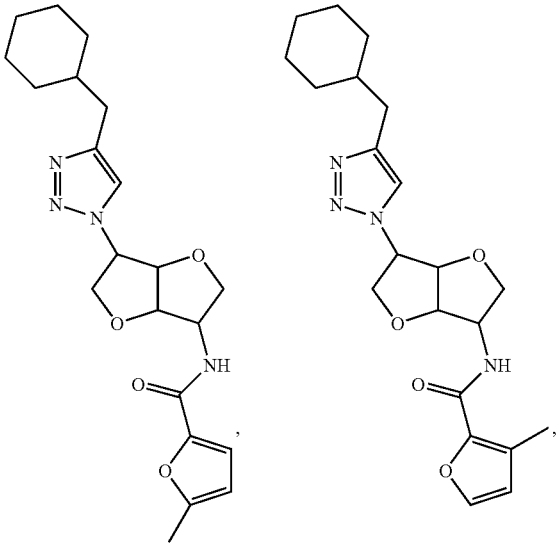
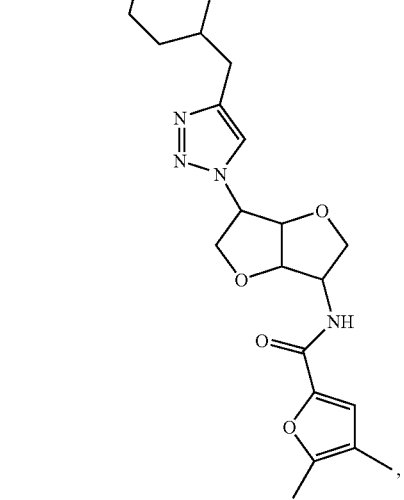

139
-continued
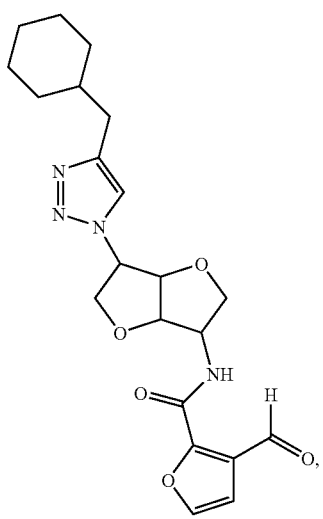
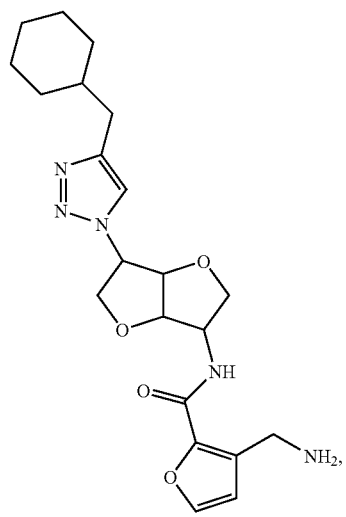
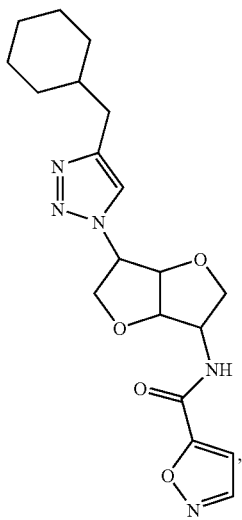
140
-continued
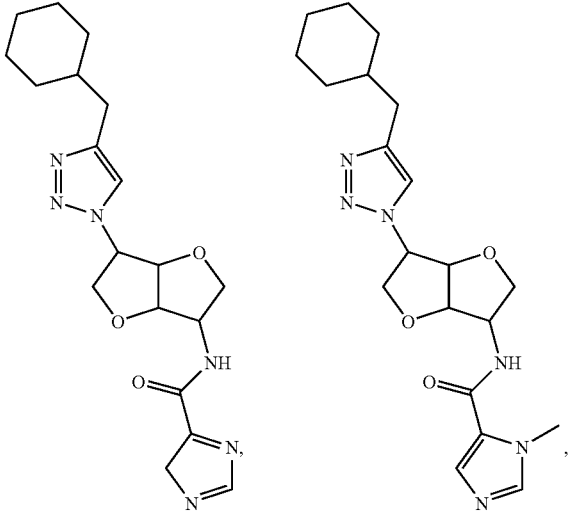
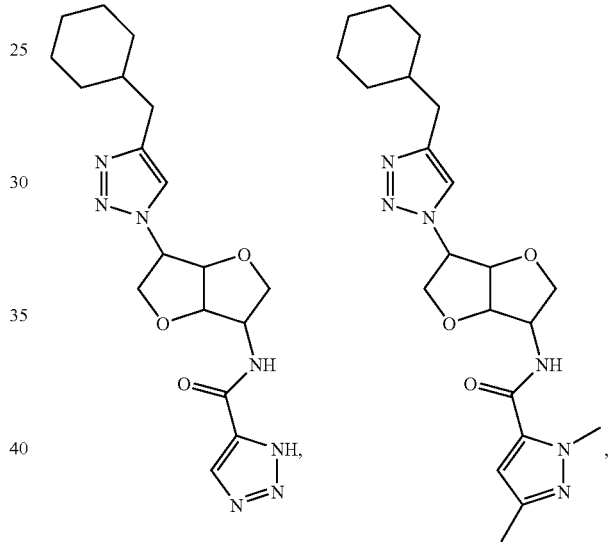
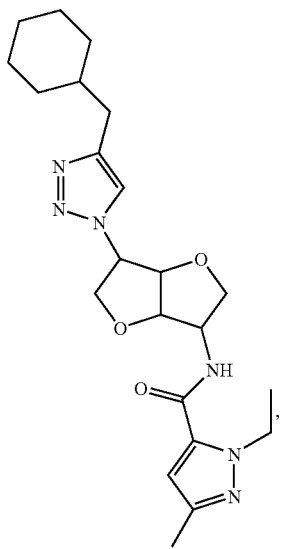

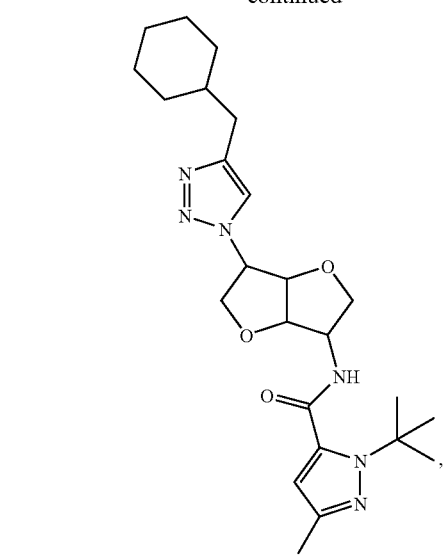
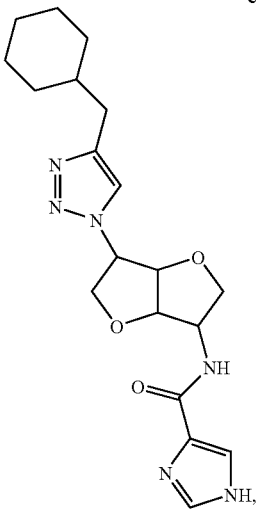
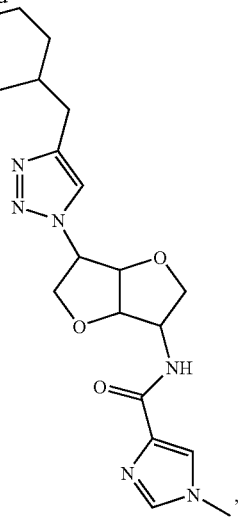
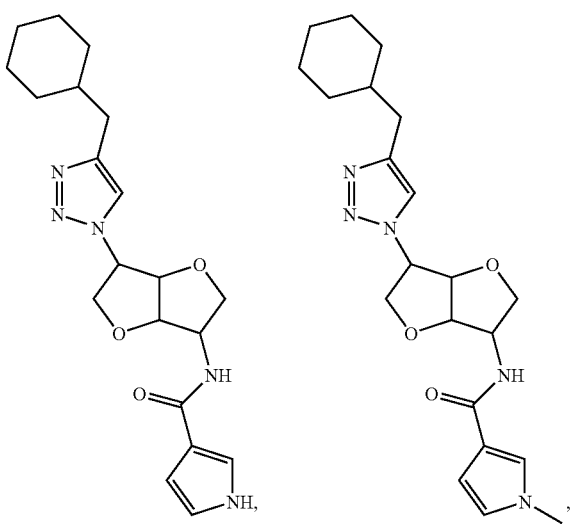
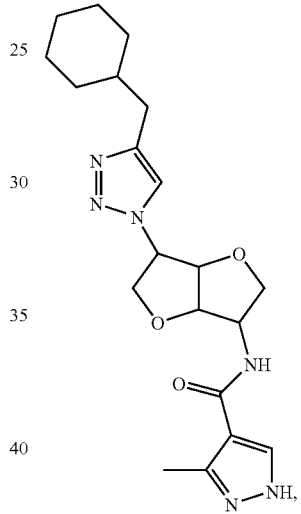
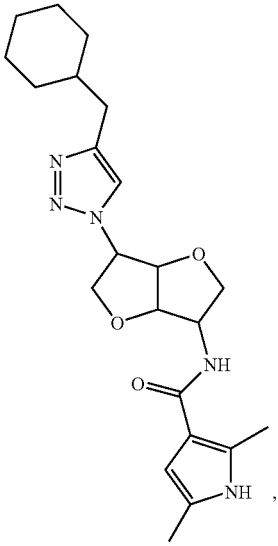
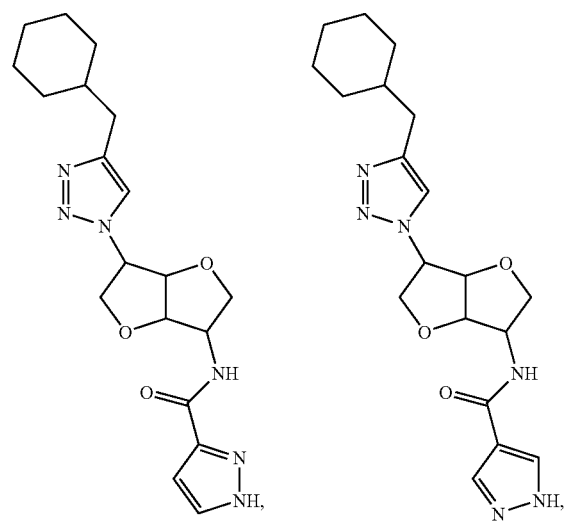
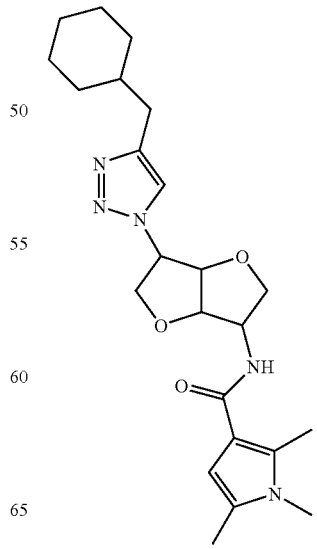
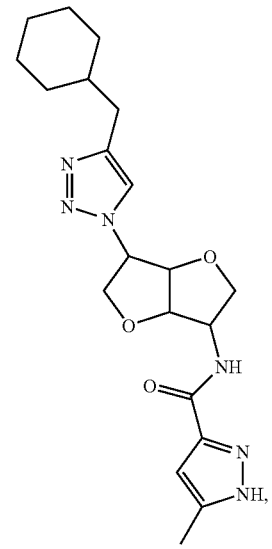

143
-continued
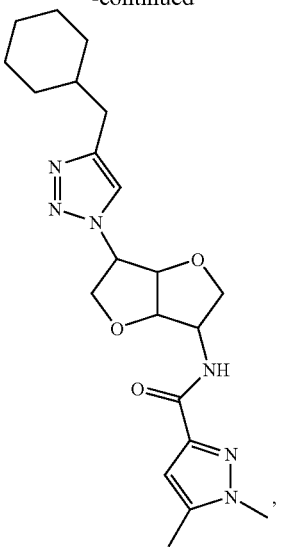
144
-continued
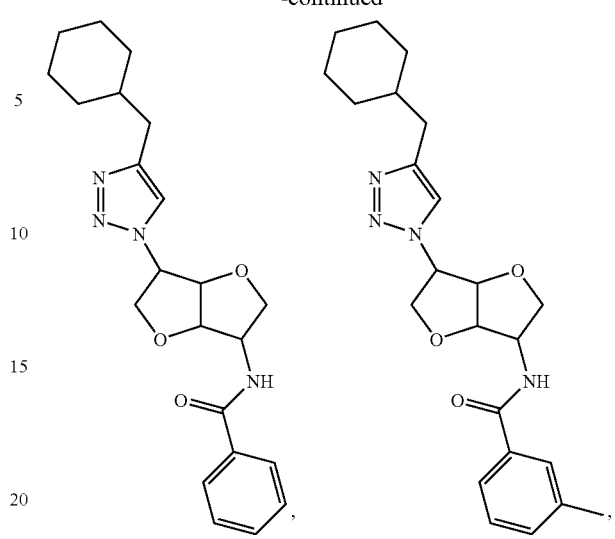
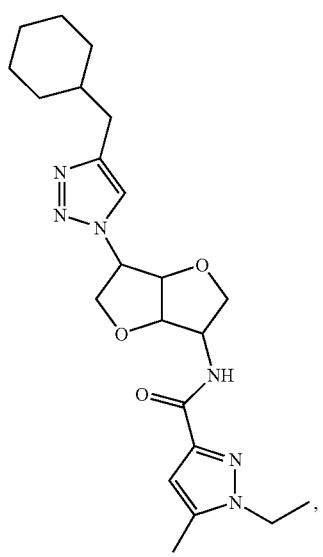
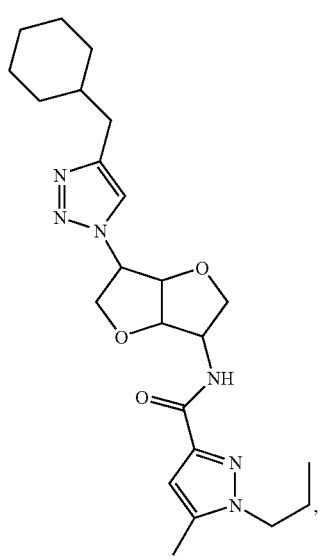
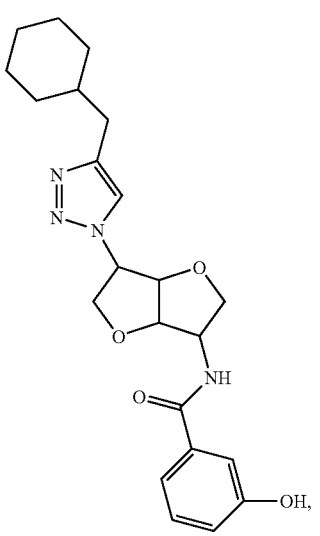

145
-continued
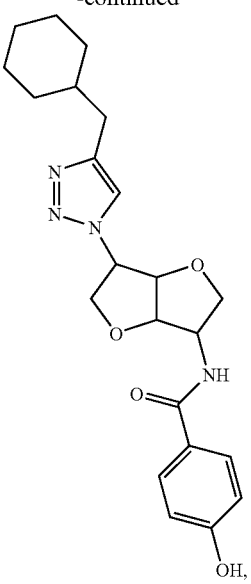
146
-continued
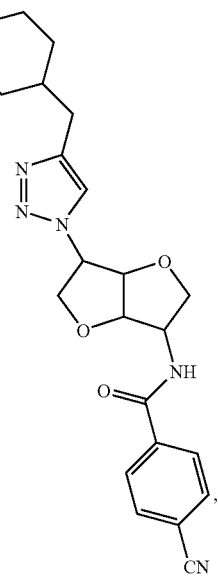
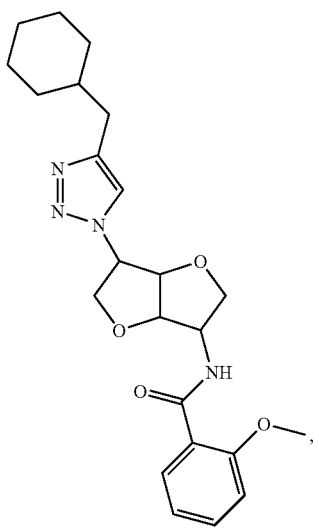
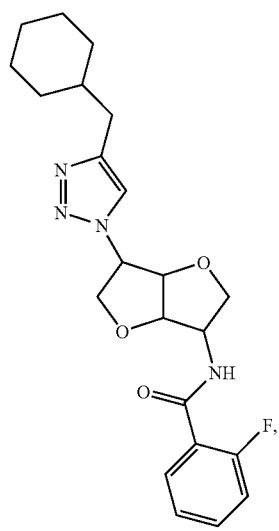
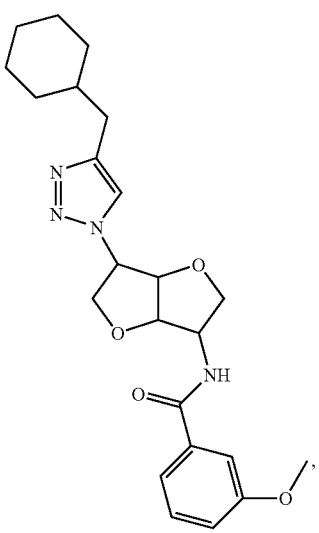
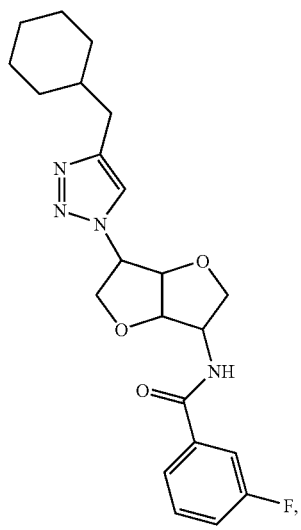

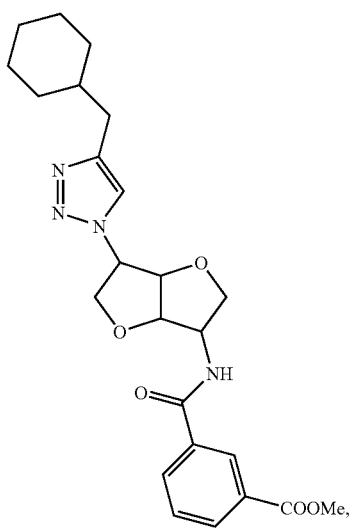
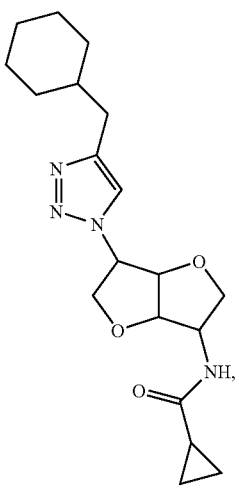
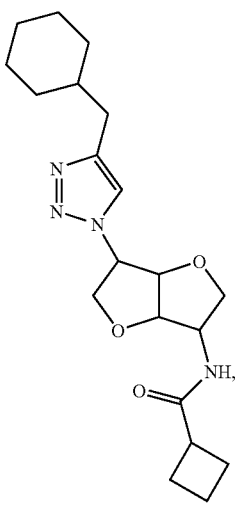
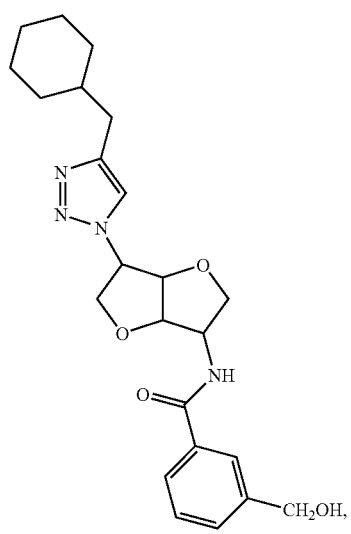
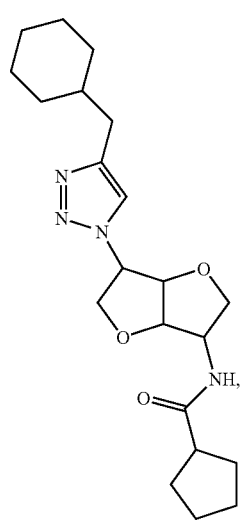
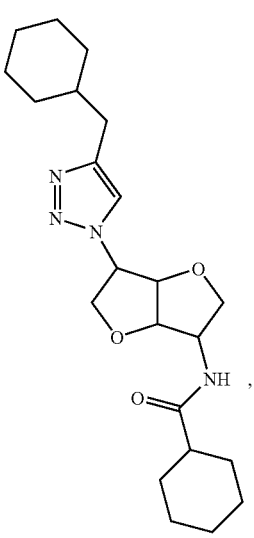
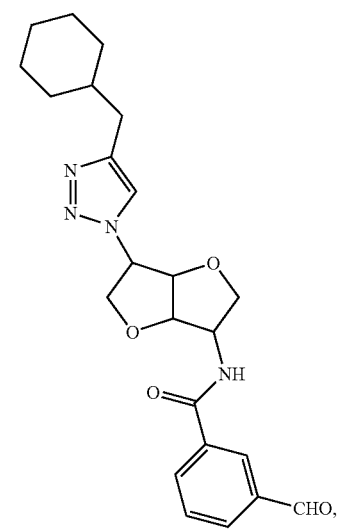
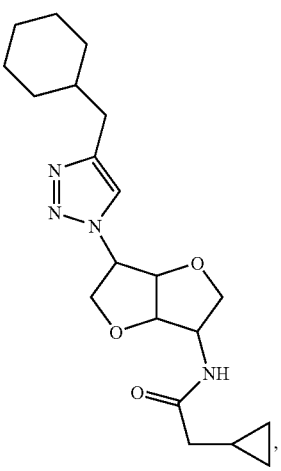

149
-continued
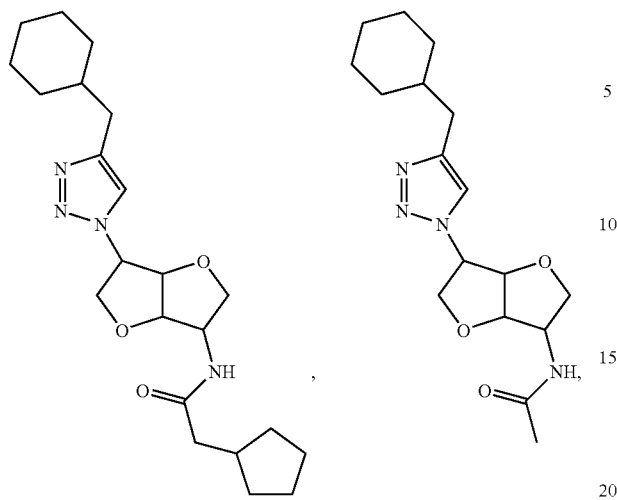
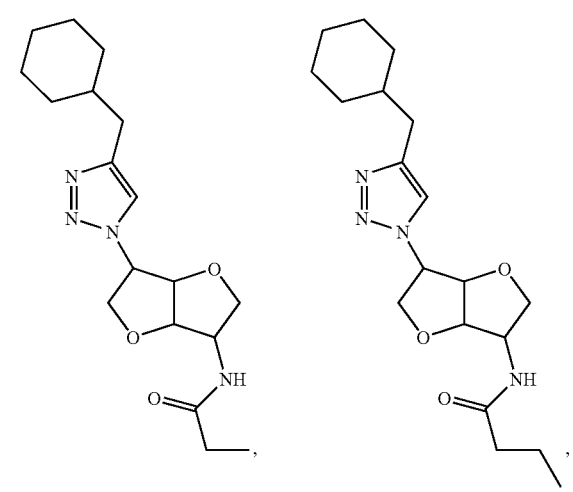
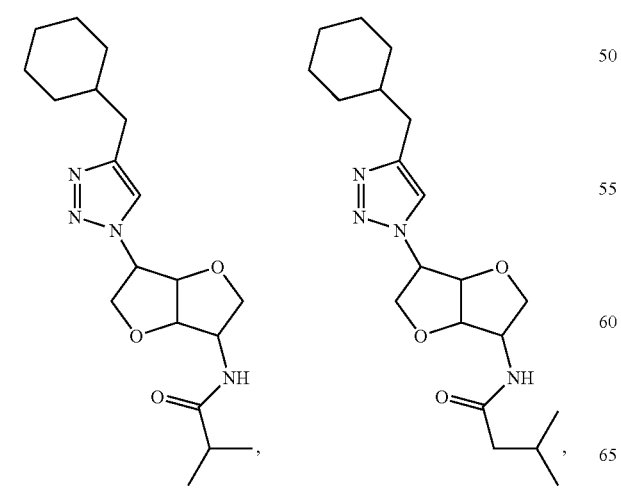
150
-continued
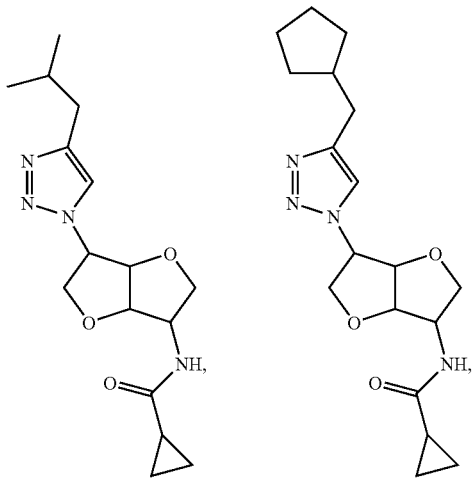
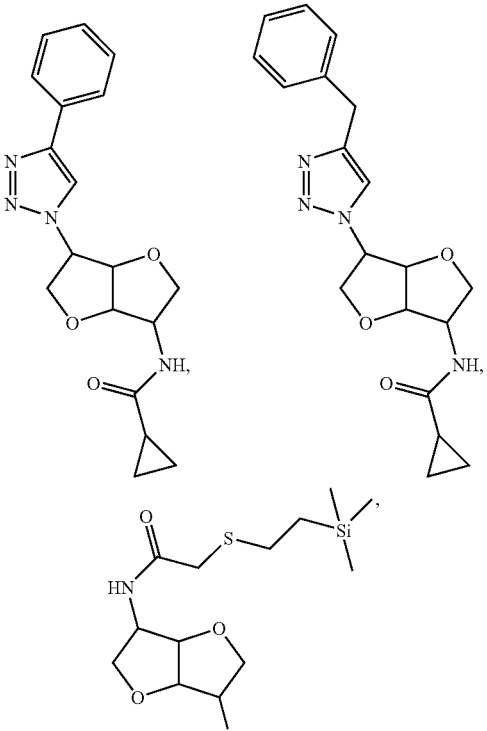
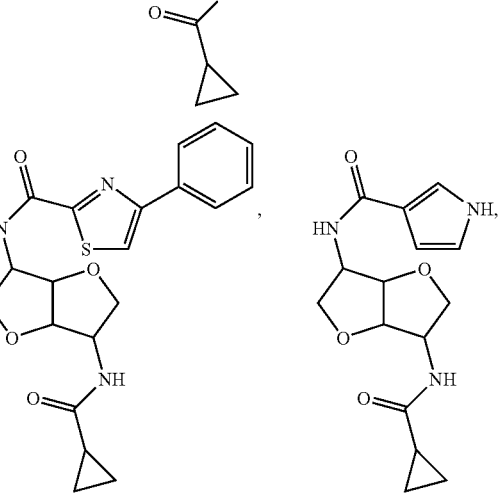

151
-continued
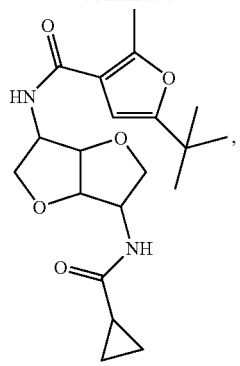
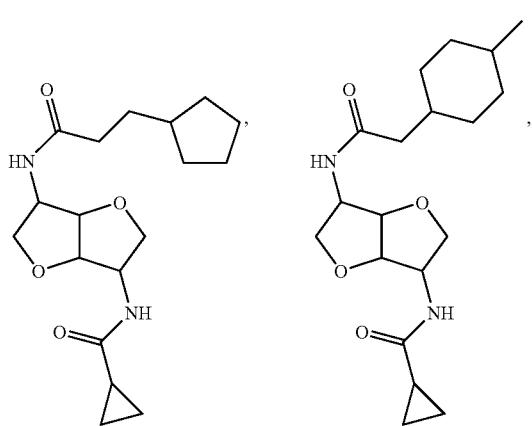
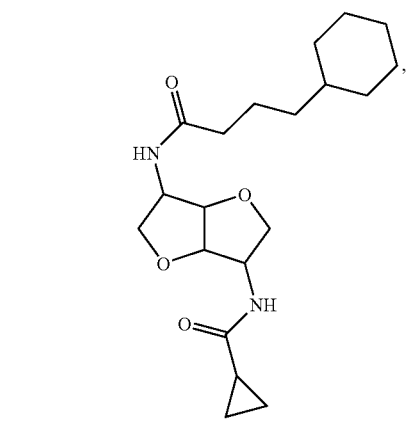
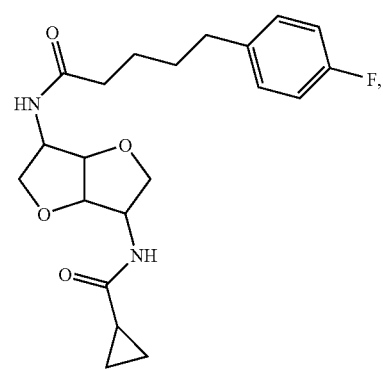
152
-continued
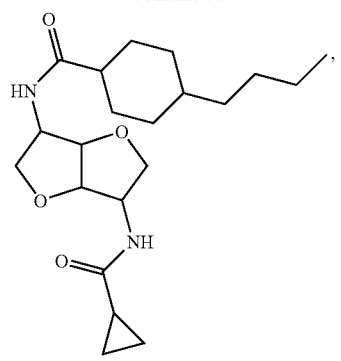
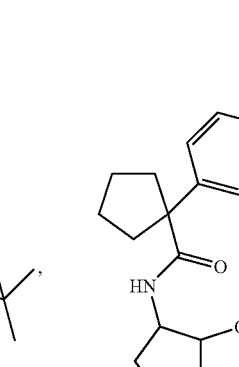
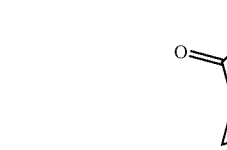
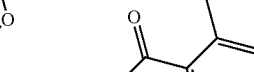
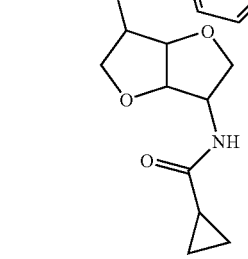

153
-continued
154
-continued
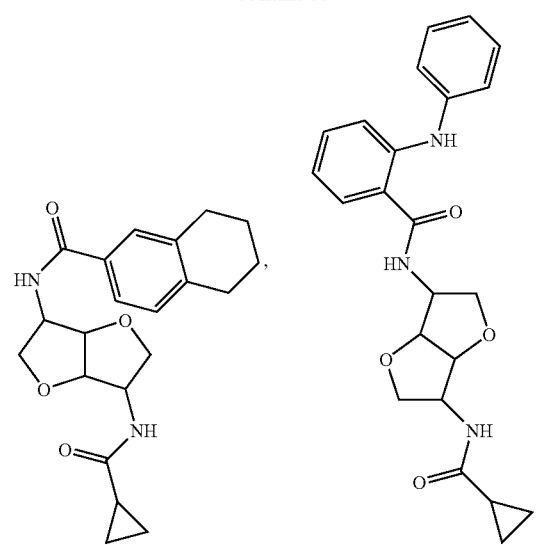
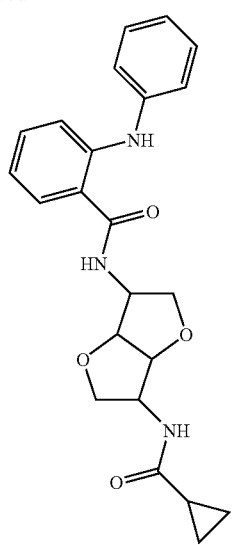
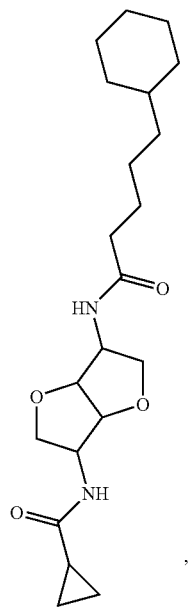
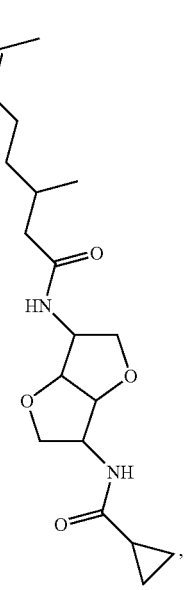
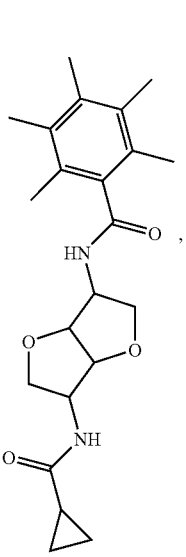
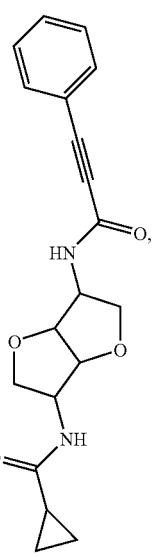
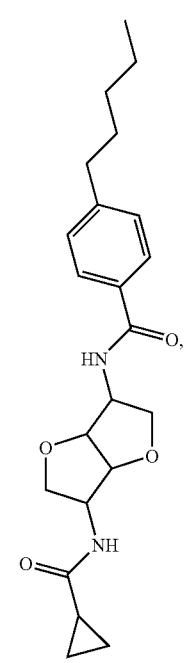
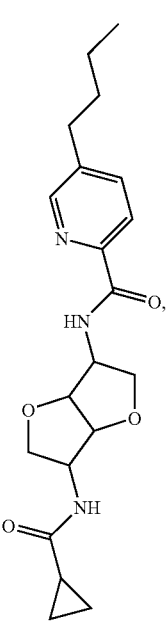
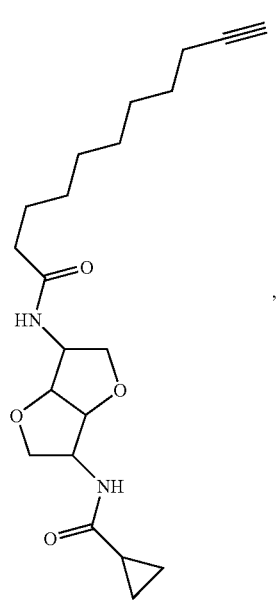

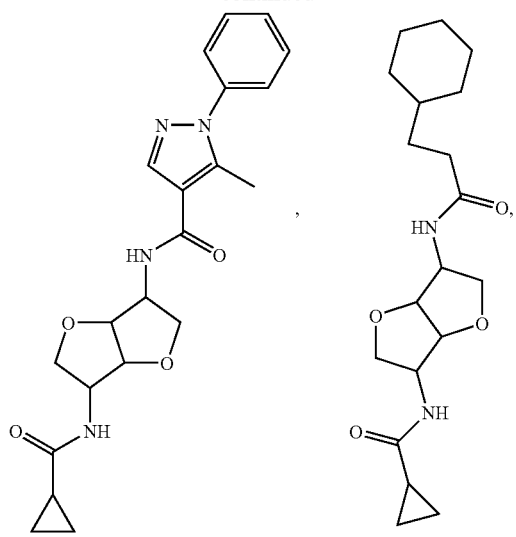 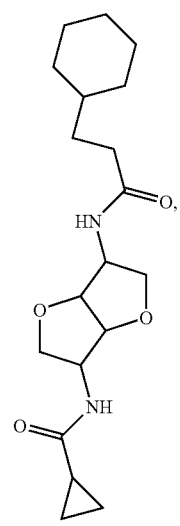 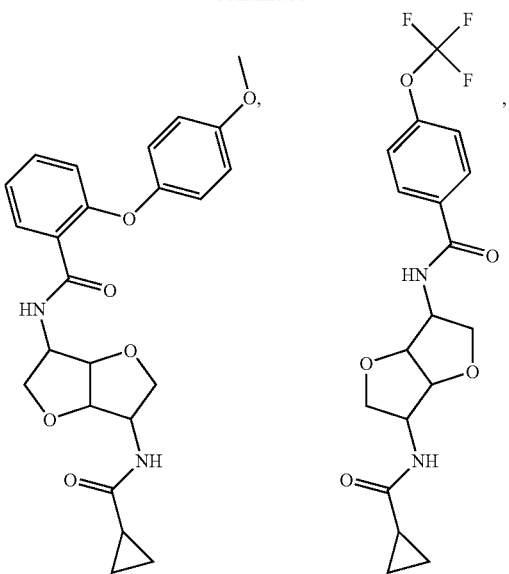 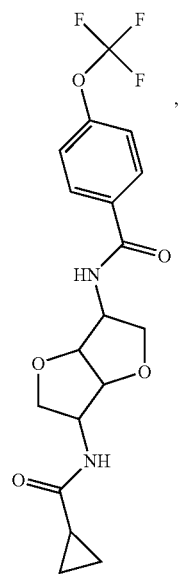
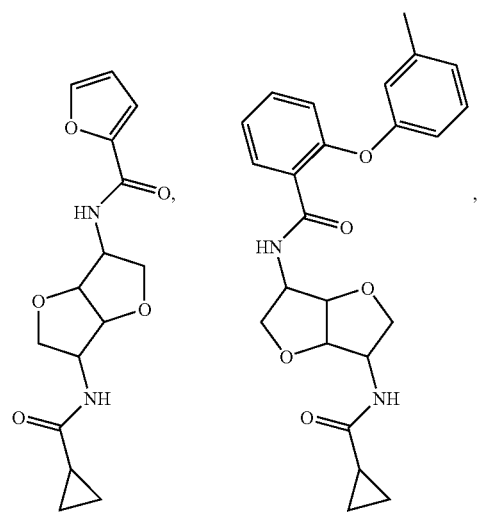 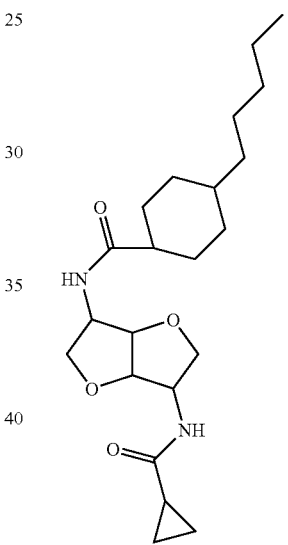 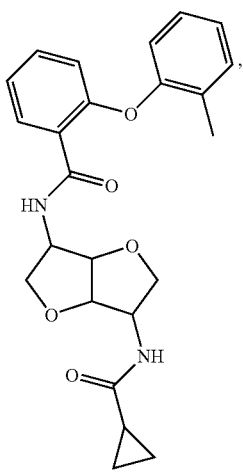
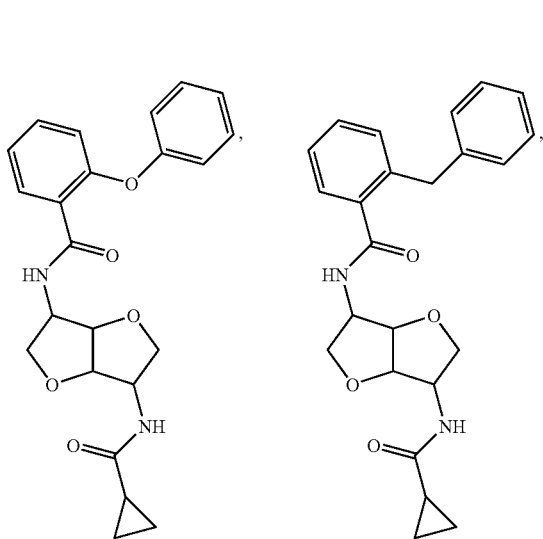 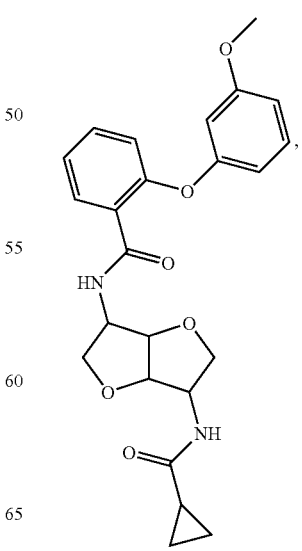 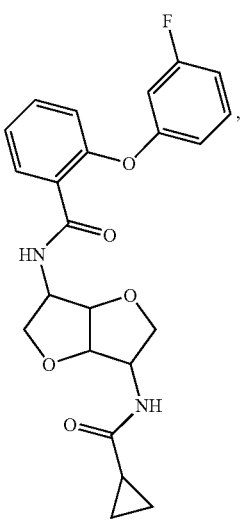

157
-continued
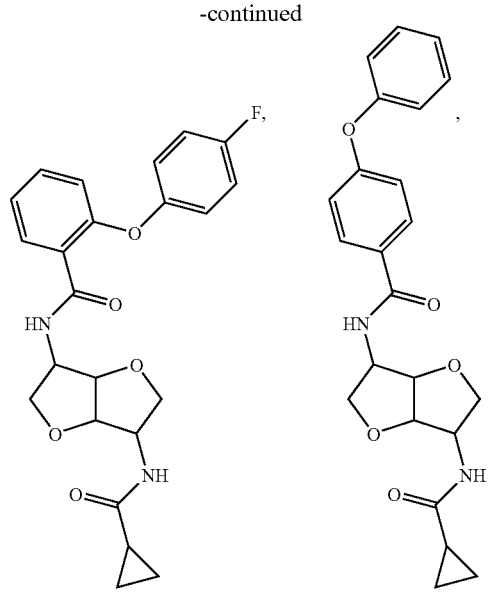
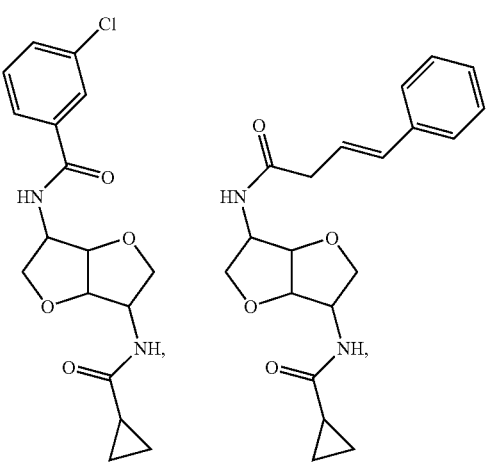
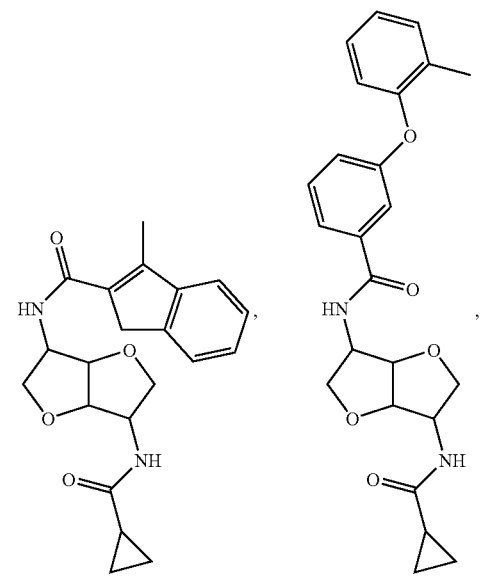
158
-continued
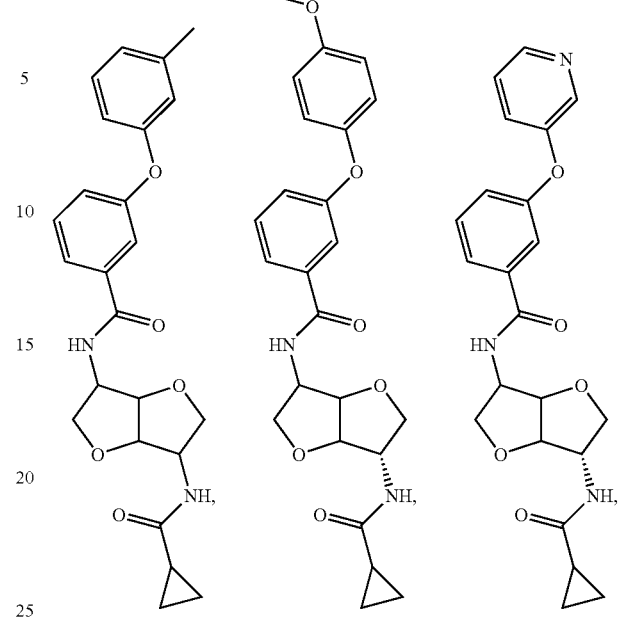
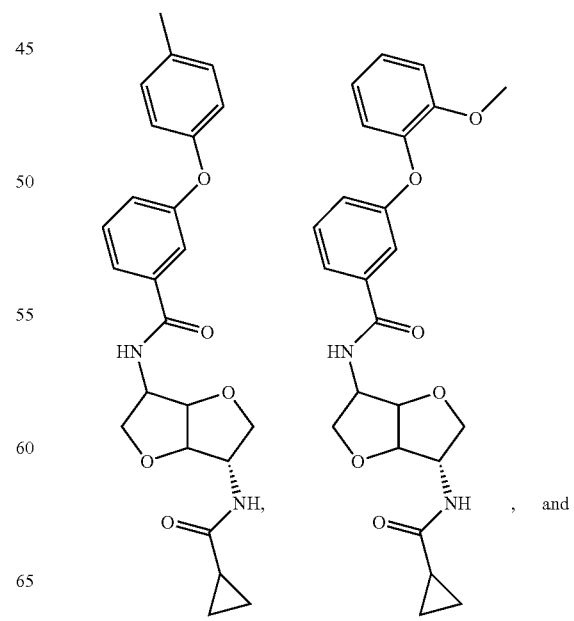

-continued

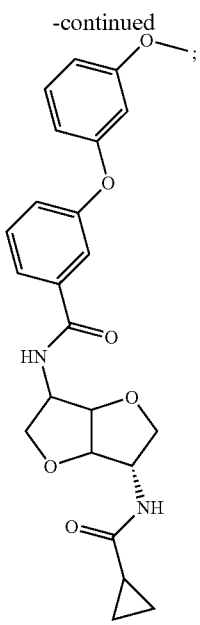

or the salt, solvate, ester, or N-oxide thereof.

6. A composition comprising a compound having structural formula (I) of claim 1, or the salt, solvate, ester, or N-oxide thereof; and a carrier.

7. The composition of claim 6, which comprises an ingestible composition.

8. A method for modulating the savory taste of a composition comprising combining the composition with at least one compound of formula (I) according to claim 1.

9. A food or beverage product comprising a compound of formula (I) according to claim 1.

10. A compound of the following structural formula (I):

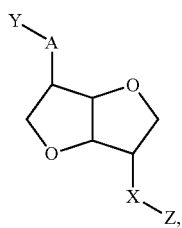

(I)

or a salt, solvate, ester, or N-oxide thereof, wherein
A is a covalent bond;
Y is -N(R$^1$)C(O)R$^2$, —NR$^1$R$^2$, —C(O)NR$^1$R$^2$, —N(R$^1$)S(O)$_2$R$^2$, —N(R$^1$)—C(=N—OR$^2$)R$^6$, —C(=N—OR$^1$)R$^2$, —C(=NR$^1$)—NR$^2$R$^6$, 13 N(R$^1$)C(=NR$^2$)R$^6$, 13 N(R$^1$)C(S)R$^2$, —N(R$^1$)—C(O)—C(O)R$^2$, —N(R$^1$)C(S)N(R$^2$)—R$^6$, —C(S)—NR$^1$R$^2$, —N(R$^1$)C(=NR$^2$)OR$^6$, —C(=NR$^1$)O—NR$^2$R$^6$, —N(R$^1$)—C(=NR$^2$)—N(R$^6$)R$^7$, —N(R$^1$)N(R$^2$)C(O)OR$^6$ —N(R$^1$)C(O)OR$^2$, —N(R$^1$)C(O)NR$^2$R$^6$, or —N(R$^1$)—C(O)—C(O)—NR$^2$R$^6$;

X is —N(R$^3$)C(O)—, —N(R$^3$)—, —N(R$^3$)S(O)$_2$—, —N(R$^3$)—C(=N—OR$^4$)—, —N(R$^3$)C(=NR$^4$)—, —N(R$^1$)—C(=NR$^2$)—N(R$^6$)—, —N(R$^3$)C(S)—, —N(R$^3$)C(S)N(R$^4$)—, —N(R$^3$)C(O)N(R$^4$)—, —N(R$^3$)C(=NR$^4$)O—, —N(R$^3$)—C(=NR$^4$)—N(R$^5$)—, —N(R$^3$)N(R$^4$)C(O)O—, or —N(R$^3$)C(O)O—;

Z is aryl, substituted aryl, heteroaryl, substituted heteroaryl, arylalkyl, substituted arylalkyl, heteroarylalkyl, substituted heteroarylalkyl, carbocyclyl, or substituted carbocyclyl; and R$^1$, R$^2$, R$^6$ and R$^7$ are each independently alkyl, substituted alkyl, alkenyl, substituted alkenyl, alkynyl, substituted alkylnyl, heteroalkyl, substituted heteroalkyl, aryl, substituted aryl, arylalkyl, substituted arylalkyl, arylalkenyl, substituted arylalkenyl, heteroaryl, substituted heteroaryl, heterocyclyl, substituted heterocyclyl, carbocyclyl, substituted carbocyclyl, heteroarylalkyl, or substituted heteroarylalkyl.

11. The compound of claim 10, wherein Z is carbocyclyl or substituted carbocyclyl.

12. A ingestible composition comprising a compound of formula (I) of claim 10, or the salt, solvate, ester, or N-oxide thereof.

13. The ingestible composition of claim 12, which is a food or beverage.

14. A method for modulating the savory taste of a composition comprising combining the composition with at least one compound of formula (I) according to claim 10.

* * * * *